Figure 1A:
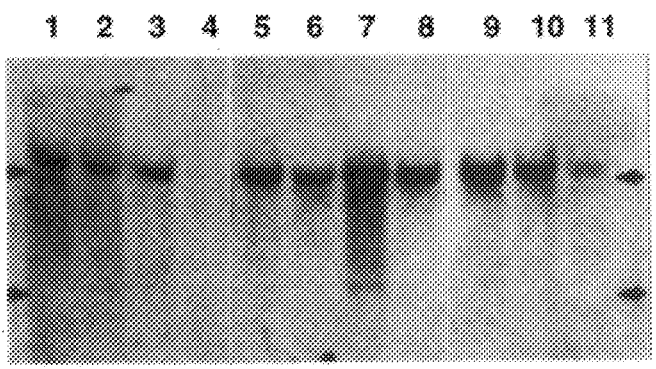

United States Patent [19]
Wilks et al.

[11] Patent Number: 5,852,184
[45] Date of Patent: Dec. 22, 1998

[54] PROTEIN TYROSINE KINASE

[75] Inventors: Andrew Frederick Wilks, Doneaster East; Ailsa Harpur, Mooroolbark, both of Australia

[73] Assignee: Ludwig Institute for Cancer Research, New York, N.Y.

[21] Appl. No.: 64,067

[22] PCT Filed: Nov. 26, 1991

[86] PCT No.: PCT/US91/08889

§ 371 Date: Jun. 30, 1993

§ 102(e) Date: Jun. 30, 1993

[87] PCT Pub. No.: WO92/10519

PCT Pub. Date: Jun. 25, 1992

[30] Foreign Application Priority Data

Nov. 28, 1990 [AU] Australia .......................... PK3594/90

[51] Int. Cl.⁶ .................................................. C15N 15/54
[52] U.S. Cl. .................... 536/23.2; 536/23.1; 435/320.1; 435/172.3; 435/194
[58] Field of Search ................................. 536/23.2, 23.1; 435/320.1, 194

[56] References Cited

U.S. PATENT DOCUMENTS 4,543,439 9/1985 Frackelton ............................ 435/70.21

OTHER PUBLICATIONS

Firmbach–Kraft et al Oncogene (1990) 5:1329–36.
Wilks Proc. Nat. Acad Sci, USA (1989) 86 1603–1607.
Bernards. Oncogene (1991) 6 1185–1187.
Harpur et al. Oncogene (1992) 7: 1347–1353.
Wilks et al Mol. Cell. Biol. (1991) 11: 2057–2065.
Hanks, "The Protein Kinase Family: Conserved Features and Deduced Phylogeny of the Catalytic Domains", vol. 241, pp. 42–52 (Jul. 1988).
Gaudette, "Effect of Genistein, A Tyrosine Kinase Inhibitor, On U46619—Induced Phosphoinositide Phosphorylation In Human Platelets", Biochem. Biophys. Res. Comm. vol. 170, No. 1, pp. 238–242 (Jul. 1990).
Koch, "SH2 and SH3 Domains: Elements That Control Interactions of Cytoplasmic Signaling Proteins", vol. 252, pp. 668–674 (May 1991.
Sadowski, "A Noncatalytic Domain Conserved among Cytoplasmic Protein–Tyrosine Kinases Modifies the Kinase Function and Transforming Activity of Fujinami Sarcoma Virus P130gag–fps", Mol. and Cell Biol. vol. 6, No. 12, pp. 4396–4408 (Dec. 1986).
Yarden, "Growth Factor Receptor Tyrosine Kinases", Ann. Rev. Biochem. vol. 57, pp. 443–478 (1988).

*Primary Examiner*—Robert A. Wax
*Attorney, Agent, or Firm*—Felfe & Lynch

[57] ABSTRACT

The present invention is directed to a novel protein tyrosine kinase comprising a polypeptide having multiple protein kinase catalytic domains and, more particularly, two kinase catalytic domains and to genetic sequences encoding same. Two such kinases are described and designated JAK1 and JAK2.

5 Claims, 34 Drawing Sheets

FIG. 2A

```
TGGCCGCCTA GCGAGCTGCC GGTCGACCCC AGCCAGCCGA AGCCAGCCGA GCGACGGGCG CTGCCTGGCC  60
CAGGGCACAC GGAAGTGCGC TTCTCTGAAG TAGCTTTGGA AAGTAGAGAA GAAAATCCAG 120
TTTGCTTCTT GGAGAACACT GGACAGCTGA ATAA ATG CAG TAT CTA AAT
169                                    Met Gln Tyr Leu Asn
                                               -10
```

```
ATA AAA GAG GAC TGC AAT GCC ATG GCT TTC TGT GCT AAA ATG AGG     214
Ile Lys Glu Asp Cys Asn Ala Met Ala Phe Cys Ala Lys Met Arg
 -5                        +1                       5

AGC TCC AAG AAG ACT GAG GTG AAC CTG GAG GCC CCT GAG CCA GGG     259
Ser Ser Lys Lys Thr Glu Val Asn Leu Glu Ala Pro Glu Pro Gly
        10                      15                  20

GTG GAA GTG ATC TTC TAT CTG TCG GAC AGG GAG CCC CTC CGG CTG     304
Val Glu Val Ile Phe Tyr Leu Ser Asp Arg Glu Pro Leu Arg Leu
        25                      30                  35

GGC AGT GGA GAG TAC ACA GCA GAG GAA CTG TGC ATC AGG GCT GCA     349
Gly Ser Gly Glu Tyr Thr Ala Glu Glu Leu Cys Ile Arg Ala Ala
        40                      45                  50
```

FIG. 2B

```
CAG GCA TGC CGT ATC TCT CCT CTT TGT CAC AAC CTC TTT GCC CTG    394
Gln Ala Cys Arg Ile Ser Pro Leu Cys His Asn Leu Phe Ala Leu
 55                  60                  65

TAT GAC GAG AAC ACC AAG CTC TGG TAT GCT CCA AAT CGC ACC ATC    439
Tyr Asp Glu Asn Thr Lys Leu Trp Tyr Ala Pro Asn Arg Thr Ile
         70                  75                  80

ACC GTT GAT GAC AAG ATG TCC CTC CGG CTC CAC TAC CGG ATG AGG    484
Thr Val Asp Asp Lys Met Ser Leu Arg Leu His Tyr Arg Met Arg
             85                  90                  95

TTC TAT TTC ACC AAT TGG CAT GGA ACC AAC GAC AAT GAG CAG TCA    529
Phe Tyr Phe Thr Asn Trp His Gly Thr Asn Asp Asn Glu Gln Ser
                100                 105                 110

GTG TGG CGT CAT TCT CCA AAG AAG CAG AAA AAT GGC TAC GAG AAA    574
Val Trp Arg His Ser Pro Lys Lys Gln Lys Asn Gly Tyr Glu Lys
            115                 120                 125

AAA ATT CCA GAT GCA ACC CCT CTC CTT GAT GCC AGC TCA CTG        619
Lys Ile Pro Asp Ala Thr Pro Leu Leu Asp Ala Ser Ser Leu
            130                 135                 140

GAG TAT CTG TTT GCT CAG GGA CAG TAT GAT TTG GTG AAA TGC CTG    664
Glu Tyr Leu Phe Ala Gln Gly Gln Tyr Asp Leu Val Lys Cys Leu
            145                 150                 155
```

FIG. 2C

```
GCT CCT ATT CGA GAC CCC AAG ACC GAG CAG GAT GGA CAT GAT ATT    709
Ala Pro Ile Arg Asp Pro Lys Thr Glu Gln Asp Gly His Asp Ile
        160                 165                 170

GAG AAC GAG TGT CTA GGG ATG GCT GTC CTG GCC ATC TCA CAC TAT    754
Glu Asn Glu Cys Leu Gly Met Ala Val Leu Ala Ile Ser His Tyr
            175                 180                 185

GCC ATG ATG AAG AAG ATG CAG TTG CCA GAA CTG CCC AAG GAC ATC    799
Ala Met Met Lys Lys Met Gln Leu Pro Glu Leu Pro Lys Asp Ile
        190                 195                 200

AGC TAC AAG CGA TAT ATT CCA GAA ACA TTG AAT AAG TCC ATC AGA    844
Ser Tyr Lys Arg Tyr Ile Pro Glu Thr Leu Asn Lys Ser Ile Arg
            205                 210                 215

CAG AGG AAC CTT CTC ACC AGG ATG CGG ATA AAT AAT GTT TTC AAG    889
Gln Arg Asn Leu Leu Thr Arg Met Arg Ile Asn Asn Val Phe Lys
        220                 225                 230

GAT TTC CTA AAG GAA TTT AAC AAG ACC ATT TGT GAC AGC AGC        934
Asp Phe Leu Lys Glu Phe Asn Lys Thr Ile Cys Asp Ser Ser
            235                 240                 245
```

FIG. 2D

```
GTG TCC ACG CAT GAC CTG AAG GTG AAA TAC TTG GCT ACC TTG GAA    979
Val Ser Thr His Asp Leu Lys Val Lys Tyr Leu Ala Thr Leu Glu
                            255                 260

ACT TTG ACA AAA CAT TAC GGT GCT GAA ATA TTT GAG ACT TCC ATG   1024
Thr Leu Thr Lys His Tyr Gly Ala Glu Ile Phe Glu Thr Ser Met
            265                 270                 275

TTA CTG ATT TCA TCA GAA AAT GAG ATG AAT TGG TTT CAT TCG AAT   1069
Leu Leu Ile Ser Ser Glu Asn Glu Met Asn Trp Phe His Ser Asn
        280                 285                 290

GAC GGT GGA AAC GTT CTC TAC TAC GAA TAC TAT GTG ACT GGG AAT   1114
Asp Gly Gly Asn Val Leu Tyr Tyr Glu Tyr Val Met Thr Gly Asn
    295                 300                 305

CTT GGA ATC CAG TGG AGG CAT AAA CCA AAT GTT TCT GTT GAA       1159
Leu Gly Ile Gln Trp Arg His Lys Pro Asn Val Ser Val Glu
310                 315                 320

AAG GAA AAA AAT AAA CTG AAG CGG AAA AAA CTG GAA AAT AAA GAC   1204
Lys Glu Lys Asn Lys Leu Lys Arg Lys Lys Leu Glu Asn Lys Asp
325                 330                 335

AAG AAG GAT GAG GAG AAA AAC AAG ATC CGG GAA TGG AAC AAT       1249
Lys Lys Asp Glu Glu Lys Asn Lys Ile Arg Glu Trp Asn Asn
340                 345                 350
```

FIG. 2E

```
TTT TCA TTC TTC CCT GAA ATC ACT CAC ATT GTA ATA AAG GAG TCT    1294
Phe Ser Phe Phe Pro Glu Ile Thr His Ile Val Ile Lys Glu Ser
355                 360                 365

GTC AGC ATT AAC AAG CAG GAC AAC AAG AAA ATG GAA CTG AAG        1339
Val Val Ser Ile Asn Lys Gln Asp Asn Lys Lys Met Glu Leu Lys
370                 375                 380

CTC TCT TCC CAC GAG GAG GCC TTG TCC TTT GTG TCC CTG GTA GAT    1384
Leu Ser Ser His Glu Glu Ala Leu Ser Phe Val Ser Leu Val Asp
385                 390                 395

GGC TAC TTC CGG CTC ACA GCA GAT GCC CAT TAC CTC TGC ACC        1429
Gly Tyr Phe Arg Leu Thr Ala Asp Ala His Tyr Leu Cys Thr
400                 405                 410

GAC GTG GCC CCC CCG TTG ATC GTC CAC AAC ATA CAG AAT GGC TGT    1474
Asp Val Ala Pro Pro Leu Ile Val His Asn Ile Gln Asn Gly Cys
415                 420                 425

CAT GGT CCA ATC TGT ACA GAA TAC GCC ATC AAT AAA TTG CGG CAA    1519
His Gly Pro Ile Cys Thr Glu Tyr Ala Ile Asn Lys Leu Arg Gln
430                 435                 440
```

FIG. 2F

```
GAA GGA AGC GAG GAG GGG ATG TAC GTG CTG AGG TGG AGC TGC ACC       1564
Glu Gly Ser Glu Glu Gly Met Tyr Val Leu Arg Trp Ser Cys Thr
445                 450                 455

GAC TTT GAC AAC ATC CTC ATG ACC GTC ACC TGC TTT GAG AAG TCT       1609
Asp Phe Asp Asn Ile Leu Met Thr Val Thr Cys Phe Glu Lys Ser
        460                 465                 470

GAG CAG GTG CAG GGT GCC CAG AAG CAG TTC AAG TTT CAG ATC           1654
Glu Gln Val Gln Gly Ala Gln Lys Gln Phe Lys Asn Phe Gln Ile
475                 480                 485

GAG GTG CAG AAG GGC CGC TAC AGT CTG CAC GGT TCG GAC CGC AGC       1699
Glu Val Gln Lys Gly Arg Tyr Ser Leu His Gly Ser Asp Arg Ser
490                 495                 500

TTC CCC AGC TTG GGA GAC CTC ATG AGC CAC CTC AAG AAG CAG ATC       1744
Phe Pro Ser Leu Gly Asp Leu Met Ser His Leu Lys Lys Gln Ile
505                 510                 515

CTG CGC ACG GAT AAC ATC AGC TTC ATG CTA AAA CGC TGC TGC CAG       1789
Leu Arg Thr Asp Asn Ile Ser Phe Met Leu Lys Arg Cys Cys Gln
520                 525                 530
```

FIG. 2G

```
CCC AAG CCC CGA GAA ATC TCC AAC CTG CTG GTG GCT ACT AAG AAA
Pro Lys Pro Arg Glu Ile Ser Asn Leu Leu Val Ala Thr Lys Lys    1834
535                 540                 545

GCC CAG GAG TGG CAG CCC TAC CCC ATG AGC CAG CTG AGT TTC
Ala Gln Glu Trp Gln Pro Tyr Pro Met Ser Gln Leu Ser Phe        1879
550                 555                 560

GAT CGG ATC CTC AAG AAG GAT CTG GTG CAG GGC GAG CAC CTT GGG
Asp Arg Ile Leu Lys Lys Asp Leu Val Gln Gly Glu His Leu Gly    1924
565                 570                 575
        I_a

AGA GGC ACG AGA ACA CAC ATC TAT TCT GGG ACC CTG ATG GAT TAC
Arg Gly Thr Arg Thr His Ile Tyr Ser Gly Thr Leu Met Asp Tyr    1969
580                 585                 590

AAG GAT GAC GAA GGA ACT TCT GAA GAG AAG AAG ATA AAA GTG ATC
Lys Asp Asp Glu Gly Thr Ser Glu Glu Lys Lys Ile Lys Val Ile    2014
595                 600                 605
II_a

CTC AAA GTC TTA GAC CCC AGC CAC AGG GAT ATT TCC CTG GCC TTC
Leu Lys Val Leu Asp Pro Ser His Arg Asp Ile Ser Leu Ala Phe    2059
605                 615                 620
```

FIG. 2H

```
          IIIₐ                                                                IVₐ
TTC GAG GCA GCC AGC ATG AGA CAG GTC TCC CAC AAA CAC ATC    2104
Phe Glu Ala Ala Ser Met Arg Gln Val Ser His Lys His Ile
            625                 630                 635

GTG TAC CTC TAT GGC GTC TGT GTC CGC GAC GTG GAG AAT ATC ATG    2149
Val Tyr Leu Tyr Gly Val Cys Val Arg Asp Val Glu Asn Ile Met
            640                 645                 650
                            Vₐ
GTG GAA GAG TTT GTG GAA GGG GGT CCT CTG GAT CTC TTC ATG CAC    2194
Val Glu Glu Phe Val Glu Gly Gly Pro Leu Asp Leu Phe Met His
            655                 660                 665

CGG AAA AGT GAT GTC CTT ACC ACA CCA TGG AAA TTC AAA GTT GCC    2239
Arg Lys Ser Asp Val Leu Thr Thr Pro Trp Lys Phe Lys Val Ala
            670                 675                 680

AAA CAG CTG GCC AGT GCC CTG AGC TAC TTG GAG GAT AAA GAC CTG    2284
Lys Gln Leu Ala Ser Ala Leu Ser Tyr Leu Glu Asp Lys Asp Leu
            685                 690                 695
         VIₐ
GTC CAT GGA AAT GTG TGT ACT AAA AAC CTC CTG CTG GCC CGT GAG    2329
Val His Gly Asn Val Cys Thr Lys Asn Leu Leu Leu Ala Arg Glu
            700                 705                 710
```

FIG. 21

```
                                                                                      VIIₐ
GGA ATC GAC AGT GAG TGT CCA TTC ATC AAG CTC AGT GAC CCC    2374
Gly Ile Asp Ser Glu Cys Gly Pro Phe Ile Lys Leu Ser Asp Pro
715                 720                 725

GGC ATC CCC ATT ACG GTG CTG TCT AGG CAA GAA TGC ATT GAA CGA    2419
Gly Ile Pro Ile Thr Val Leu Ser Arg Gln Glu Cys Ile Glu Arg
730                 735                 740
        VIIIₐ
ATC CCA TGG ATT GCT CCT GAG TGT GTT GAG GAC TCC AAG AAC CTG    2464
Ile Pro Trp Ile Ala Pro Glu Cys Val Glu Asp Ser Lys Asn Leu
745                 750                 755
                                IXₐ
AGT GTG GCT GCT GAC AAG TGG AGC TTT GGA ACC ACG CTC TGG GAA    2509
Ser Val Ala Ala Asp Lys Trp Ser Phe Gly Thr Thr Leu Trp Glu
760                 765                 770

ATC TGC TAC AAT GGC GAG ATC CCC TTG AAA GAC AAG ACG CTG ATT    2554
Ile Cys Tyr Asn Gly Glu Ile Pro Leu Lys Asp Lys Thr Leu Ile
775                 780                 785
                                            Xₐ
GAG AAA GAG AGA TTC TAT GAA AGC CGG TGC AGG CCA GTG ACA CCA    2599
Glu Lys Glu Arg Phe Tyr Glu Ser Arg Cys Arg Pro Val Thr Pro
790                 795                 800
                                                            XIₐ
TCA TGT AAG GAG CTG GCT GAC CTC ATG ACC CGC TGC ATG AAC TAT    2644
Ser Cys Lys Glu Leu Ala Asp Leu Met Thr Arg Cys Met Asn Tyr
805                 810                 815
```

FIG. 2J

```
GAC CCC AAT CAG AGG CCT TTC TTC CGA GCC ATC ATG AGA GAC ATT    2689
Asp Pro Asn Gln Arg Pro Phe Phe Arg Ala Ile Met Arg Asp Ile
820                 825                 830

AAT AAG CTT GAA GAG CAG AAT CCA GAT ATT GTT TCC AGA AAA AAA    2734
Asn Lys Leu Glu Glu Gln Asn Pro Asp Ile Val Ser Arg Lys Lys
        835                 840                 845

AAC CAG CCA ACT GAA GTG GAC CCC ACA CAT TTT GAG AAG CGC TTC    2779
Asn Gln Pro Thr Glu Val Asp Pro Thr His Phe Glu Lys Arg Phe
850                 855                 860
                                    I

CTA AAG AGG ATC CGT GAC TTG GGA GAG GGC CAC TTT GGG AAG GTT    2824
Leu Lys Arg Ile Arg Asp Leu Gly Glu Gly His Phe Gly Lys Val
        865                 870                 875

GAG CTC TGC AGG TAT GAC CCC GAA GAC AAT ACA GGG GAG CAG GTG    2869
Glu Leu Cys Arg Tyr Asp Pro Glu Asp Asn Thr Gly Glu Gln Val
880                 885                 890
II

GCT GTT AAA TCT CTG AAG CCT GAG AGT GGA GGT AAC CAC ATA GCT    2914
Ala Val Lys Ser Leu Lys Pro Glu Ser Gly Gly Asn His Ile Ala
        895                 900                 905

GAT CTG AAA AAG GAA ATC TTA AGG AAC CTC TAT CAT GAG            2959
Asp Leu Lys Lys Glu Ile Leu Arg Asn Leu Tyr His Glu
910                 915                 920
        III
```

FIG. 2K

```
      IV
AAC ATT GTG AAG TAC AAA GGA ATC TGC ACA GAA GAC GGA GGA AAT    3004
Asn Ile Val Lys Tyr Lys Gly Ile Cys Thr Glu Asp Gly Gly Asn
        925                 930                 935
                                                 V
GGT ATT AAG CTC ATC ATG GAA TTT CTG CCT TCG GGA AGC CTT AAG    3049
Gly Ile Lys Leu Ile Met Glu Phe Leu Pro Ser Gly Ser Leu Lys
        940                 945                 950

GAA TAT CTT CCA AAG AAT AAA AAA ATA AAC CTC AAA CAG CAG        3094
Glu Tyr Leu Pro Lys Asn Lys Lys Ile Asn Leu Lys Gln Gln
        955                 960                 965

CTA AAA TAT GCC GTT CAG ATT TGT AAG GGG ATG GAC TAT TTG GGT    3139
Leu Lys Tyr Ala Val Gln Ile Cys Lys Gly Met Asp Tyr Leu Gly
        970                 975                 980
                         VI
TCT CGG CAA TAC GTT CAC CGG GAC TTG GCA GCA AGA AAT GTC CTT    3184
Ser Arg Gln Tyr Val His Arg Asp Leu Ala Ala Arg Asn Val Leu
        985                 990                 995
                                         VII
GTT GAG AGT GAA CAC CAA GTG AAA ATT GGA GAC TTC GGT TTA ACC    3229
Val Glu Ser Glu His Gln Val Lys Ile Gly Asp Phe Gly Leu Thr
        1000                1005                1010

AAA GCA ATT GAA ACC GAT AAG GAG TAT TAC ACC GTC AAG GAT GAC    3279
Lys Ala Ile Glu Thr Asp Lys Glu Tyr Tyr Thr Val Lys Asp Asp
        1015                1020                1025
```

FIG. 2L

```
      VIII
CGG GAC AGC CCT GTG TTT TGG TAT GCT CCA GAA TGT TTA ATG CAA    3319
Arg Asp Ser Pro Val Phe Trp Tyr Ala Pro Glu Cys Leu Met Gln
    1030                    1035                    1040
                                                     IX
TCT AAA TTT TAT ATT GCC TCT GAC GTC TGG TCT TTT GGA GTC ACT    3364
Ser Lys Phe Tyr Ile Ala Ser Asp Val Trp Ser Phe Gly Val Thr
    1045                    1050                    1055

CTG CAT GAG CTG CTG ACT TAC TGT GAT TCA GAT TCT AGT CCC ATG    3409
Leu His Glu Leu Leu Thr Tyr Cys Asp Ser Asp Ser Ser Pro Met
    1060                    1065                    1070
                                                     X
GCT TTG TTC CTG AAA ATG ATA GGC CCA ACC CAT GGC CAG ATG ACA    3454
Ala Leu Phe Leu Lys Met Ile Gly Pro Thr His Gly Gln Met Thr
    1075                    1080                    1085

GTC ACA AGA CTT GTG AAT ACG TTA AAA GAA GGA AAA CGC CTG CCG    3499
Val Thr Arg Leu Val Asn Thr Leu Lys Glu Gly Lys Arg Leu Pro
    1090                    1095                    1100

TGC CCA CCT AAC TGT CCA GAT GAG GTT TAT CAG CTT ATG AGA AAA    3544
Cys Pro Pro Asn Cys Pro Asp Glu Val Tyr Gln Leu Met Arg Lys
    1105                    1110                    1115
```

FIG. 2M

```
                                                                               XI
TGC TGG GAA TTC CAA CCA AAT CGG ACA AGC TTT CAG AAC CTT        3589
Cys Trp Glu Phe Gln Pro Asn Arg Thr Ser Phe Gln Asn Leu
   1120                            1125                1130

ATT GAA GGA TTT GAA GCA CTT TTA AAA TAAGAAGCAT GAATAACATT
3636
Ile Glu Gly Phe Glu Ala Leu Leu Lys
   1135                    1140

TAAATTCCAC AGATTATCAA GTCCTTCTCC TGCAACAAAT GCCCAAGTCA TTTTTTAAAA3696
ATTTCTAATG AAAGAAGTTT GTGTTCTGTC CAAAAAGTCA CTGAACTCAT ACTTCAGTAC3756
ATATACATGT ATAAGGCACA CTGTAGTGCT TAATATGTGT AAGGACTTCC TCTTTAAATT3816
TGCACCAGTA ACTTAGTGAC ACATAATGAC AACCAAAATA TTTGAAAGCA CTTAAGCACT3876
CCTCCTTGTG GAAAGAATAT ACCACCATTT CATCTGGCTA GTTCACCATC ACAACTGCAT3936
TACCAAAAGG GGATTTTTGA AAACGAGGAG TTGACCAAAA TAATATCTGA AGATGATTGC3996
TTTTCCCTGC TGCCAGCTGA CTGAAATGTT TTCCTGGCAC ATTAATCATA GATAAAGAAG4056
ATTGATGGAC TTAGCCCTCA AACAGTATCT ATACAGTACT AGACCATGCA TTCTTAAAAT4116
ATTAGATACC AGGTAGTATA TATTGTTTCT GTACAAAAAT GACTGTATTC TCTCACCAGT4176
AGGACTTAAA CTTTGTTTCT CCAGTGGCTT AGCTCCTGTT CCTTTGGGTG ATCACTAG 4234
```

FIG. 3A

```
              I                                II                    III
Domain 1  HLGRGTRTHIYSGTLMDYKDDEGTSEEKKIKVILRKVLDPS...HRDISLAGGEAASM         -60aa-
Domain 2  DLGEGHFGKVELCRT.DPEDNTGE.......QVAVKSLKPES.GGNHIADLKKEIEIL         -63aa-
CDC2-H    KIGEGTYGVVYKGRH....KYYG.......QVVAMKKIRLESEEEGVPSTAIREISLL         -55aa- IX
              VI                              VII                   IAPECVEDSKNLSVAADKWSFGTTLWEIC  -20aa-
Domain 1  SYLEDKDLVHGNVCTKNLLLAREGIDSECGPFIKLSDPGIPITVLS.......RQECIERIPW.YAPECLMQSKF.YIASDVWSFGVTLHELL  -38aa-
Domain 2  DYLGSRQYVHRDLAARNVLVESE......VKIGDFGLTKAIETDKEYYTVKDDRDSPCFW.LMYRSPEVLLGSARYSTPVDIWSIGTIFAELA  -50aa-
CDC2-H    VFCHSRRVLHRDLKPQNLLIDDKG......TIKLADGGLARAFGIPIRVYTHE...VVT.

XI
Domain 1  SRCRPVTPSCKELADLMTRCMNYDPNQRPF
Domain 2  LPCPPNCPDEVYQ..LMRKCWEFQPSNRTS
CDC2-H    LASHHVKNLDENGLDLLSKMLIYDPAKRIS
```

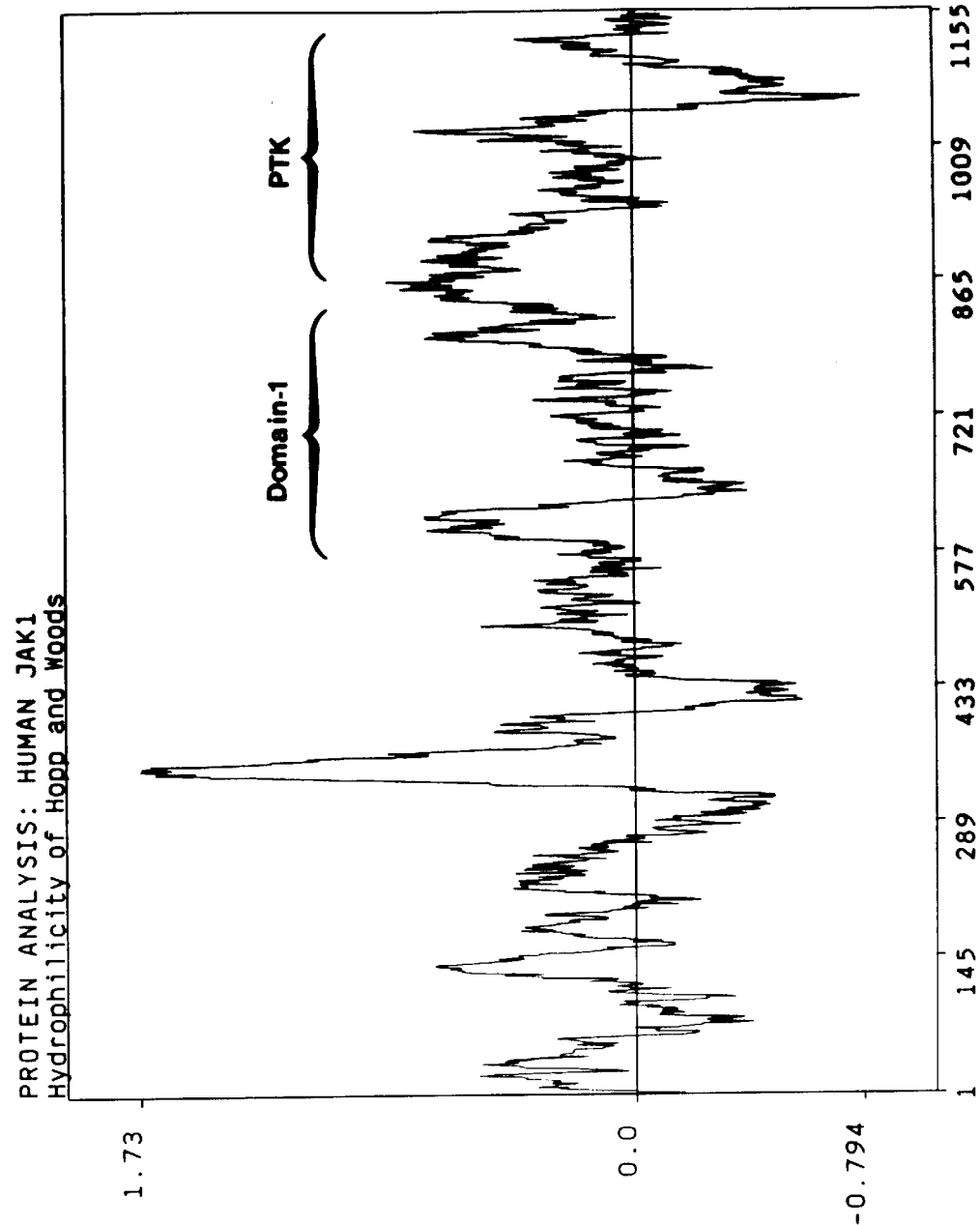

FIG. 5

```
                    Ia                              IIa         IIIa 70
VFHKIRNEDL IFNESLGQGT FTKIFKGVRR EVGDYGQLHE TE...VLLKV LDKAHRNYSE SFFEAASMMS MJAK2
 *$*         **  $ *  ** **   * *$ *   $ *      * *$*** **  **  * ********
SFDRILKKDL VQGEHLGRGT RTHIYSGTLM DYKDDEGTSE EKKIKVILKV LDPSHRDISL AFFEAASMMR HJAK1

IVa                 Va                                              140
QLSHKHLVLN YGVCVCGEEN ILVQEFVKFG SLDTYLKKNK NSINILWKLG VAKQLAWAMH FLEEKSLIHG MJAK2
*$****$*    *****      ** * ***  *  ** $   $      **  ****** *  $**$*  *$**
QVSHKHIVYL YGVCVRDVEN IMVEEFVEGG PLDLFMHRKS DVLTTPWKFK VAKQLASALS YLEDKDLVHG HJAK1

VIa              VIIa                         VIIIa         210
NVCAKNILLI REEDRRTGNP PFIKLSDPGI SITVLPKDIS SCCFQVLQER IPWVPPECIE NPKNLTLATD MJAK2
***  **$**   **         *********  ****  $         *  ** ***$  ***$*   ***$$* *
NVCTKNLLLA REGIDSECGP .FIKLSDPGI PITVLSR... .....QECIER IPWIAPECVE DSKNLSVAAD HJAK1

IXa                        Xa                     XIa          280
KWSFGTTLWE ICSGGDKPLS ALDSQRKLQF YEDKHQLPAP KWTELANLIN NCMDYEPDFR PAFRAVIRDL MJAK2
**********  **   *$ **        *  * ** $    *       *** *   ** *$*  *  * ***$  **$
KWSFGTTLWE ICYNGEIPLK DKTLIEKERF YESRCRPVTP SCKELADLMT RCMNYDPNQR PFFRAIMRDI HJAK1

I           350
NSLFTPDYEL LTENDMLPNM RIGALGFSGA FEDRDPTQFE ERHLKFLQQL GKGNFGSVEM CRYDPLQDNT MJAK2
 * *        $ $$      *               *** *  *  ** $  * ** ** **  *****   ***
NKLEEQNPDI VSRKKNQPTE V..........  ....DPTHFT KRFLKRIRDL GEGHFGKVEL CRYDPE.DNT HJAK1

II        III          IV                               V         420
GEVVAVKKLQ H.STEEHLRD FEREIEILKS LQHDNIVKYK GVCYSAGRRN LRLIMEYLPY GSLRDYLQKH MJAK2
**  **** *    *  *$ *  $*****$   * *$****** *$*    *   $$****$**  ***$$** *
GEQVAVKSLK PESGGNHIAD LKKEIEILRN LYHENIVKYK GICTEDGGNG IKLIMEFLPS GSLKEYLPKN HJAK1

VI         VII               490
KERIDHKKLL QYTSQICKGM EYLGTKRYIH RDLATRNILV ENENRVKIGD FGLTKVLPQD KEYYKVKEPG MJAK2
 * $*  *  *  *  ****** $***$$ *$* **** **$**  *  ***** *****$$  *  **** **$
KNKINLKQQL KYAVQICKGM DYLGSRQYVH RDLAARNVLV ESEHQVKIGD FGLTKAIETD KEYYTVKDDR HJAK1

VIII         IX                                                    560
ESPIFWYAPE SLTESKFSVA SDVWSFGVVL YELFTYIEKS KSPPVEFMRM IGNDKQGQMI VFHLIELLKS MJAK2
$**$*******    *  *** $*  ********* *  ** ** $    ** $  * $* **   ***  *   *$  **
DSPVFWYAPE CLMQSKFYIA SDVWSFGVTL HELLTYCDSD SSPMALFLKM IGPTH.GQMT VTRLVNTLKE HJAK1

X             XI          600
NGRLPRPEGC PDEIYVIMTE CWNNNVSQRP SFRDLSFGWI KSGTV       MJAK2
***  *  *  ***$*  $*    **    *  *  ** *    *
GKRLPCPPNC PDEVYQLMRK CWEFQPSNRT SFQNLIEGFE ALLK        HJAK1
```

FIG. 8A

```
CTG CTT GAT GAC TTT GTC ATG TCT TAC CTT TCC CCT CAG TGG CGG        45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA        90
His Asp Phe Val His Gly Trp Ile Lys Val Pro Val Thr His Glu
                 20                  25                  30

ACT CAG GAA GAG TGT CTT GGG ATG GCG GTG TTA GAC ATG ATG AGA       135
Thr Gln Glu Glu Cys Leu Gly Met Ala Val Leu Asp Met Met Arg
                 35                  40                  45

ATA GCT AAG GAG AAA GAC CAG ACT CCA CTG GCT GTC TAT AAC TCT       180
Ile Ala Lys Glu Lys Asp Gln Thr Pro Leu Ala Val Tyr Asn Ser
                 50                  55                  60

GTC AGC TAC AAG ACA TTC TTA CCA AAG TGC GTT CGA GCG AAG ATC       225
Val Ser Tyr Lys Thr Phe Leu Pro Lys Cys Val Arg Ala Lys Ile
                 65                  70                  75

CAA GAC TAT CAC ATT TTA ACC CGG AAG CGA ATC AGG TAC AGA TTT       270
Gln Asp Tyr His Ile Leu Thr Arg Lys Arg Ile Arg Tyr Arg Phe
                 80                  85                  90

CGC AGA TTC ATT CAG CAA TTC AGT CAA TGT AAA GCC ACT GCC AGG       315
Arg Arg Phe Ile Gln Gln Phe Ser Gln Cys Lys Ala Thr Ala Arg
                 95                 100                 105

AAC CTA AAA CTT AAG TAT CTT ATA AAC CTG GAA ACC CTG CAG TCT       360
Asn Leu Lys Leu Lys Tyr Leu Ile Asn Leu Glu Thr Leu Gln Ser
                110                 115                 120

GCC TTC TAC ACA GAA CAG TTT GAA GTA AAA GAA TCT GCA AGA GGT       405
Ala Phe Tyr Thr Glu Gln Phe Glu Val Lys Glu Ser Ala Arg Gly
                125                 130                 135

CCT TCA GGT GAG GAG ATT TTT GCA ACC ATT ATA ATA ACT GGA AAC       450
Pro Ser Gly Glu Glu Ile Phe Ala Thr Ile Ile Ile Thr Gly Asn
                140                 145                 150

GGT GGA ATT CAG TGG TCA AGA GGG AAA CAT AAG GAA AGT GAG ACA       495
Gly Gly Ile Gln Trp Ser Arg Gly Lys His Lys Glu Ser Glu Thr
                155                 160                 165
```

FIG. 8B

```
CTG ACA GAA CAG GAC GTA CAG TTA TAT TGT GAT TTC CCT GAT ATT        540
Leu Thr Glu Gln Asp Val Gln Leu Tyr Cys Asp Phe Pro Asp Ile
            170             175             180

ATT GAT GTC AGT ATT AAG CAA GCA AAT CAG GAA TGC TCA ACT GAA        585
Ile Asp Val Ser Ile Lys Gln Ala Asn Gln Glu Cys Ser Thr Glu
            185             190             195

AGT AGA GTT GTG ACC GTC CAC AAG CAG GAC GGG AAG GTC TTG GAA        630
Ser Arg Val Val Thr Val His Lys Gln Asp Gly Lys Val Leu Glu
            200             205             210

ATA GAA CTT AGC TCA TTA AAA GAA GCC TTG TCA TTC GTG TCA TTA        675
Ile Glu Leu Ser Ser Leu Lys Glu Ala Leu Ser Phe Val Ser Leu
            215             220             225

ATT GAC GGG TAT TAC AGA CTA ACT GCG GAT GCA CAC CAT TAC CTC        720
Ile Asp Gly Tyr Tyr Arg Leu Thr Ala Asp Ala His His Tyr Leu
            230             235             240

TGC AAA GAG GTG GCT CCC CCA GCT GTG TTC GAG AAC ATA CAC AGC        765
Cys Lys Glu Val Ala Pro Pro Ala Val Phe Glu Asn Ile His Ser
            245             250             255

AAC TGC CAC GGC CCA ATT TCA ATG GAT TTT GCC ATC AGC AAA CTA        810
Asn Cys His Gly Pro Ile Ser Met Asp Phe Ala Ile Ser Lys Leu
            260             265             270

AAG AAG GCA GGA AAC CAG ACT GGA CTG TAT GTA CTT CGA TGT AGC        855
Lys Lys Ala Gly Asn Gln Thr Gly Leu Tyr Val Leu Arg Cys Ser
            275             280             285

CCT AAG GAC TTC AAC AAA TAC TTC CTG ACC TTT GCC GTT GAG CGA        900
Pro Lys Asp Phe Asn Lys Tyr Phe Leu Thr Phe Ala Val Glu Arg
            290             295             300

GAA AAT GTT ATT GAA TAT AAA CAC TGT TTG ATT ACA AAG AAT GAG        945
Glu Asn Val Ile Glu Tyr Lys His Cys Leu Ile Thr Lys Asn Glu
            305             310             315
```

FIG. 8C

```
AAT GGA GAG TAC AAC CTC AGT GGG ACT AAG AGG AAC TTC AGT AGT        990
Asn Gly Glu Tyr Asn Leu Ser Gly Thr Lys Arg Asn Phe Ser Ser
                320                 325                 330

CTT AAG GAC CTT TTG AAT TGC TAC CAG ATG GAA ACT GTG CGC TCA       1035
Leu Lys Asp Leu Leu Asn Cys Tyr Gln Met Glu Thr Val Arg Ser
                335                 340                 345

GAC AGT ATC ATC TTC CAG TTC ACC AAA TGC TGT CCT CCA AAG CCG       1080
Asp Ser Ile Ile Phe Gln Phe Thr Lys Cys Cys Pro Pro Lys Pro
                350                 355                 360

AAA GAT AAA TCA AAC CTT CTT GTC TTC AGA ACA AAT GGT GTT TCT       1125
Lys Asp Lys Ser Asn Leu Leu Val Phe Arg Thr Asn Gly Val Ser
                365                 370                 375

GAT GTT CAG CTC TCA CCA ACA TTA CAG AGG CAT AAT AAT GTG AAT       1170
Asp Val Gln Leu Ser Pro Thr Leu Gln Arg His Asn Asn Val Asn
                380                 385                 390

CAA ATG GTG TTT CAC AAA ATC AGG AAT GAA GAT TTG ATA TTT AAT       1215
Gln Met Val Phe His Lys Ile Arg Asn Glu Asp Leu Ile Phe Asn
                395                 400                 405
                         Iₐ
GAA AGC CTT GGC CAA GGC ACT TTT ACA AAA ATA TTT AAA GGT GTA       1260
Glu Ser Leu Gly Gln Gly Thr Phe Thr Lys Ile Phe Lys Gly Val
                410                 415                 420

AGA AGA GAA GTT GGA GAT TAT GGT CAG CTG CAC GAA ACC GAA GTT       1305
Arg Arg Glu Val Gly Asp Tyr Gly Gln Leu His Glu Thr Glu Val
                425                 430                 435
 IIₐ
CTT TTG AAA GTC CTA GAT AAA GCA CAT AGA AAC TAT TCA GAG TCT       1350
Leu Leu Lys Val Leu Asp Lys Ala His Arg Asn Tyr Ser Glu Ser
                440                 445                 450
     IIIₐ
TTC TTT GAA GCA GCA AGC ATG ATG AGT CAG CTT TCT CAC AAG CAT       1395
Phe Phe Glu Ala Ala Ser Met Met Ser Gln Leu Ser His Lys His
                455                 460                 465
```

FIG. 8D

```
     IVa
TTG GTT TTG AAT TAT GGA GTA TGT GTC TGT GGA GAG GAG AAC ATT       1440
Leu Val Leu Asn Tyr Gly Val Cys Val Cys Gly Glu Glu Asn Ile
            470             475             480

TTG GTT CAA GAG TTT GTA AAA TTT GGA TCA CTG GAT ACA TAC CTG       1485
Leu Val Gln Glu Phe Val Lys Phe Gly Ser Leu Asp Thr Tyr Leu
            485             490             495

AAG AAG AAC AAA AAT TCT ATA AAT ATA TTA TGG AAA CTT GGA GTG       1530
Lys Lys Asn Lys Asn Ser Ile Asn Ile Leu Trp Lys Leu Gly Val
            500             505             510

GCG AAG CAG TTG GCA TGG GCC ATG CAC TTC CTC GAA GAA AAA TCC       1575
Ala Lys Gln Leu Ala Trp Ala Met His Phe Leu Glu Glu Lys Ser
            515             520             525
                 VIa
CTT ATT CAT GGG AAT GTG TGT GCT AAA AAT ATC CTG CTT ATC AGA       1620
Leu Ile His Gly Asn Val Cys Ala Lys Asn Ile Leu Leu Ile Arg
            530             535             540

GAA GAA GAC AGG AGA ACG GGG AAC CCA CCT TTC ATC AAA CTT AGT       1665
Glu Glu Asp Arg Arg Thr Gly Asn Pro Pro Phe Ile Lys Leu Ser
            545             550             555
     VIIa
GAT CCT GGC ATT AGC ATT ACA GTT CTA CCG AAG GAC ATT TCT TCC       1710
Asp Pro Gly Ile Ser Ile Thr Val Leu Pro Lys Asp Ile Ser Ser
            560             565             570
                                                 VIIIa
TGT TGT TTC CAA GTT CTT CAG GAG AGA ATA CCA TGG GTA CCA CCT       1755
Cys Cys Phe Gln Val Leu Gln Glu Arg Ile Pro Trp Val Pro Pro
            575             580             585

GAG TGC ATT GAG AAT CCT AAA AAT CTA ACT CTG GCA ACA GAC AAG       1800
Glu Cys Ile Glu Asn Pro Lys Asn Leu Thr Leu Ala Thr Asp Lys
            590             595             600
     IXa
TGG AGC TTC GGG ACC ACT CTG TGG GAG ATC TGC AGT GGA GGA GAT       1845
Trp Ser Phe Gly Thr Thr Leu Trp Glu Ile Cys Ser Gly Gly Asp
            605             610             615
```

FIG. 8E

```
AAG CCC CTG AGT GCT CTG GAT TCT CAA AGA AAG CTG CAG TTC TAT    1890
Lys Pro Leu Ser Ala Leu Asp Ser Gln Arg Lys Leu Gln Phe Tyr
                620                 625                 630
                 Xa
GAA GAT AAG CAT CAG CTT CCT GCA CCC AAG TGG ACA GAG TTG GCA    1935
Glu Asp Lys His Gln Leu Pro Ala Pro Lys Trp Thr Glu Leu Ala
                635                 640                 645
                                     XIa
AAC CTT ATA AAT AAT TGC ATG GAC TAT GAG CCA GAT TTC AGG CCT    1980
Asn Leu Ile Asn Asn Cys Met Asp Tyr Glu Pro Asp Phe Arg Pro
                650                 655                 660

GCT TTC AGA GCT GTC ATC CGT GAT CTT AAC AGC CTG TTT ACT CCA    2025
Ala Phe Arg Ala Val Ile Arg Asp Leu Asn Ser Leu Phe Thr Pro
                665                 670                 675

GAT TAT GAA CTA CTA ACA GAA AAT GAC ATG CTA CCA AAC ATG AGA    2070
Asp Tyr Glu Leu Leu Thr Glu Asn Asp Met Leu Pro Asn Met Arg
                680                 685                 690

ATA GGT GCC CTA GGG TTT TCT GGT GCT TTT GAA GAC AGG GAC CCT    2115
Ile Gly Ala Leu Gly Phe Ser Gly Ala Phe Glu Asp Arg Asp Pro
                695                 700                 705

ACA CAG TTT GAA GAG AGA CAC TTG AAG TTT CTA CAG CAG CTT GGC    2160
Thr Gln Phe Glu Glu Arg His Leu Lys Phe Leu Gln Gln Leu Gly
                710                 715                 720
  I
AAA GGT AAC TTC GGG AGT GTG GAG ATG TGC CGC TAT GAC CCG CTG    2205
Lys Gly Asn Phe Gly Ser Val Glu Met Cys Arg Tyr Asp Pro Leu
                725                 730                 735
                                     II
CAG GAC AAC ACT GGC GAG GTG GTC GCT GTG AAG AAA CTC CAG CAC    2250
Gln Asp Asn Thr Gly Glu Val Val Ala Val Lys Lys Leu Gln His
                740                 745                 750
                                         III
AGC ACT GAA GAG CAC CTC CGA GAC TTT GAG AGG GAG ATC GAG ATC    2295
Ser Thr Glu Glu His Leu Arg Asp Phe Glu Arg Glu Ile Glu Ile
                755                 760                 765
                           IV
CTG AAA TCC TTG CAG CAT GAC AAC ATC GTC AAG TAC AAG GGA GTG    2340
Leu Lys Ser Leu Gln His Asp Asn Ile Val Lys Tyr Lys Gly Val
                770                 775                 780
```

FIG. 8F

```
TGC TAC AGT GCG GGT CGG CGC AAC CTA AGA TTA ATT ATG GAA TAT        2385
Cys Tyr Ser Ala Gly Arg Arg Asn Leu Arg Leu Ile Met Glu Tyr
            785                 790                 795
        V
TTA CCA TAT GGA AGT TTA CGA GAC TAT CTC CAA AAA CAT AAA GAA        2430
Leu Pro Tyr Gly Ser Leu Arg Asp Tyr Leu Gln Lys His Lys Glu
            800                 805                 810

CGG ATA GAT CAC AAA AAA CTT CTT CAA TAC ACA TCT CAG ATA TGC        2475
Arg Ile Asp His Lys Lys Leu Leu Gln Tyr Thr Ser Gln Ile Cys
            815                 820                 825

AAG GGC ATG GAA TAT CTT GGT ACA AAA AGG TAT ATC CAC AGG GAC        2520
Lys Gly Met Glu Tyr Leu Gly Thr Lys Arg Tyr Ile His Arg Asp
            830                 835                 840
VI
CTG GCA ACA AGG AAC ATA TTG GTG GAA AAT GAG AAC AGG GTT AAA        2565
Leu Ala Thr Arg Asn Ile Leu Val Glu Asn Glu Asn Arg Val Lys
            845                 850                 855
        VII
ATA GGA GAC TTC GGA TTA ACC AAA GTC TTG CCG CAG GAC AAA GAA        2610
Ile Gly Asp Phe Gly Leu Thr Lys Val Leu Pro Gln Asp Lys Glu
            860                 865                 870

TAC TAC AAA GTA AAG GAG CCA GGG GAA AGC CCC ATA TTC TGG TAC        2655
Tyr Tyr Lys Val Lys Glu Pro Gly Glu Ser Pro Ile Phe Trp Tyr
            875                 880                 885
VIII
GCA CCT GAA TCC TTG ACG GAG AGC AAG TTT TCT GTG GCC TCA GAT        2700
Ala Pro Glu Ser Leu Thr Glu Ser Lys Phe Ser Val Ala Ser Asp
            890                 895                 900
        IX
GTG TGG AGC TTT GGA GTG GTT CTA TAC GAA CTT TTC ACA TAC ATC        2745
Val Trp Ser Phe Gly Val Val Leu Tyr Glu Leu Phe Thr Tyr Ile
            905                 910                 915

GAG AAG AGT AAA AGT CCA CCC GTG GAA TTT ATG CGA ATG ATT GGC        2790
Glu Lys Ser Lys Ser Pro Pro Val Glu Phe Met Arg Met Ile Gly
            920                 925                 930

AAT GAT AAA CAA GGG CAA ATG ATT GTG TTC CAT TTG ATA GAG CTA        2835
Asn Asp Lys Gln Gly Gln Met Ile Val Phe His Leu Ile Glu Leu
            935                 940                 945
```

FIG. 8G

```
                        X
CTG AAG AGC AAC GGA AGA TTG CCA AGG CCA GAA GGA TGC CCA GAT         2880
Leu Lys Ser Asn Gly Arg Leu Pro Arg Pro Glu Gly Cys Pro Asp
                    950                 955                 960

GAG ATT TAT GTG ATC ATG ACA GAG TGC TGG AAC AAC AAT GTG AGC         2925
Glu Ile Tyr Val Ile Met Thr Glu Cys Trp Asn Asn Asn Val Ser
                    965                 970                 975
            XI
CAG CGT CCC TCC TTC AGG GAC CTT TCC TTC GGG TGG ATC AAA TCC         2970
Gln Arg Pro Ser Phe Arg Asp Leu Ser Phe Gly Trp Ile Lys Ser
                    980                 985                 990

GGG ACA GTA TAGCTGCGTG AAAGAGATGG CCTTACTCAG AGACCAAGCA             3019
Gly Thr Val

GACTTCCAGA ACCAGAACAA AGCTCTGTAG CCTTGTGTCT ACACATCCTT              3069
ATCATGACGC TAGCTAGGCA GAAAGAAAAC TGTGACGCCG TCTGCTCAAA              3119
AGCTTTGGAA AACGCCGTGC AGGTTTGTTT CATCACCATC TGTAAAAACC              3169
ACTGCTCAAG TCTGGCAGCA TGCTTGTGGG CTGATGCATG GAGCTCACCA              3219
CAGAGTCTCT GCATCTCCTC TGACAGAAGA AGAAAAATAG ACAATTTTCA              3269
ACTCACTTTT TTGAGAAATG GAAAAAAATT ATAATGTAAA TTTTTCAGTG              3319
TAGGAAATAC ACAGAACATA CATGTACAGT TTTTACCACG TGGAGTGTAT              3369
AATACTTTGG CCTCTTGTGT GATTTACATG AGGGCTGATG TTTGTTAATG              3419
TTTTCTAATT TTTCCATAGG TGATCTATAA TAACTTCATG ATACAAATTA              3469
AAATGCTCAG AAAATTAAAA AAAAAA                                        3495
```

FIG. 11A

```
         1           11          21          31          41          51          61          71          81          91
J1   MQYLNIKEDCNAMAFCAKMRSSKKTEVNLEAPEPGVEIFYLSDREPLRLGSEYTAEELCIRAAQACRISPLCHNLFALYDENTKLWYAPNRTITVDDK
J2
T2   MPLRHWGMARGSKPVGDGAQPMAAMGGLKVLLHWAGPGGGEPWVTFSESSLI....AAEEVCIHIAHKVGITPPCFNLFALFDAQAQVWLPPNHILEIPRD
                                                                AEE-CI-------P-C-NLFAL----W--PN-----------

101         111         121         131         141         151         161         171         181         191
J1   MSLRLHYRMRFYFTNWHGTNDNEQSVWRHSPKKQKNGYEKKKIPDATPLLDASSLEYLFAQGQYDLVKCLAPIRDPK.TEQDGHDIENECLGMAVLAISHY
J2                                                           LLDDFVMSYLSPQWRHDFVHGWIKVPVTHETQEE........CLGMAVLDMMRI
T2   ASLMLYFRIRFYFRNWHGMNPREPAGYRCGPPGTEASSDQTAQGMQ...LLDPASFEYLFEQGKHEFENDVASLWELS.TEEEIHHFKNESLGMAFLHLCHL
     -SL--L--R--RFYF-NWHG--N---E-----R--P----------------LLD---S-EYLF--QG-HDFV----A------------TEEE-H----NECLGMAVL---H--
                                               JH6→

201         211         221         231         241         251         261         271         281         291
J1   AMMKKMQLPELPKDISYKRYIPETLNKSIRQRNLLTRMRINNVFKDFLKEFNNKTICDSSVSTHDLKVKYLATLETLTKHYGAEIFETSMLLISSENEMN
J2   AKEKDQTPLAVYNSVSYKTFLPKCVRAKIQDYHILTRKIRYRFRRFIQQFSQCKATARN......LKLKYLINLETLQSAFYTEQFEVKESARGPSGEEI
T2   ALRHGIPLEEVAKKTSFKDCIPRSFRRHIRQHSALTRLRLRNVFRRFLRDFQPGRLSQQM.....VMVKYLATLERLAPRFGTERVPVCHLRLLAQAEGE
     A---K----L--EV--K---SYK----IP------R---IRQ----R-IRNVFRRFL---F---------LTR--RIRNVFRRFL-----FGTE-FEV---L-----E-----
                                                                                                              →JH6

301         311         321         331         341         351         361         371         381         391
J1   WFHSNDGGNVLYY...........EVMVTGNLGIQWRHKPNVVSVEKEKNKLKRKKLENKDKKDEEKNK.......IREEWNNFSFFPEITHIVIKESV
J2   FAT.........IIITGNGGIQWSRGKHKESETLTEQDLQLYCDFP.........DIIDVSIKQANQECSTESRI
T2   PSYIRDSGVAPTDPGPESAAGPPTHEVLVTGTGGIQWPVEEEVNKEEGSGSSARNPQASLFGKKAKAHKAFGQPADRPREPLMAYFCDITHVVLKEHC
     ------D-G-----      EV--VTGNGGIQW------VS--E-|-----------L-----------K-----------R-------S-F--ITH-V--KE--
                               JH5→                                                      JH4→

401         411         421         431         441         451         461         471         481         491
J1   VSINKQDNKKMELKLSSHEEALSFVSLVDGYFRLTADAHHYLCTDVAPPLIVHNIQNGCHGPIC-EYAI.NKLRQEGSEEGMYVLRWSCTDFDNILMTVT
J2   VTVHKQDGEVLEIELSSLKEALSFVSLIDGYYRLTADAHHYLCKEVAPPAVLENIHSNCHGPISMDFAI.SKLKKAGNQTGLYVLRCSPKDFNKYFLTFA
T2   VSIHRQDNKCLELSLPSRAAALSFESLVDGYFRLTADSSHYLCHEVAPPRLVMSIRDGIHGPLLEPFVQQAKLRP..LEDGLYLIHWSTSHPYRLLILTVA
     VSIHKQDNK--LEL--LSS--EALSFVSLVDGYFRLTADAHHYLC--EVAPP----V--NI---GCHGPI-----FAI---KLR---G--E-GLYVLRWS---DF-----LTVA
                                                                                                              →JH4
```

FIG. 11B

```
        501         511         521         531         541         551         561         571         581         591
J1  CFEKSEQVQGAQKQFKNFQIEVQKGRYSLHGSDRSFPSLGDLMSHLKKQILRTDNISFMLKRCCQPKPREISNLLVATKKAQEWQPVYPMSQLSFDRILK
J2  VER.....ENVIEYKHCLITKNENGEYNLSGTKRNFSSLKDLLNCYQMETVRSDSIIFQFTKCCPPKPKDKSNLLVFRTNGVSDVQLSPTLQRHNNVNQM
T2  QRSQAPDGMQSLRLRKF.PIEQQDGAFVLEGWGRSFPSVRELGAALQGCLLRAGDDCFSLRRCCLPQPGETSNLIIMRGARASPRTL.NLSQLSFHRVDQ
    -----------------K---IE-Q-G-Y-L-G--RSFPSL-DL---LQ---LR-D-I-F-L-RCC-PKP-E-SNLLV-R---S---L-P-SQLSF-R---
                      JH3→
        601         611         621         631         641         651         661         671         681         691
J1  KD.......LVQGEHLGRGTRTHIYSGTLMDYKDDEGTSEEKK..................IKVILKVLDPSHRDISLAFFEAASMMRQVSHKHIVYLYGVC
J2  VFHKIRNEDLIFNESLGQGTFTKIFKGVRREVGDY.GQLHETE..............VLLKVLDKAHRNYSESFFEAASMMSQLSHKHLVLNYGVC
T2  KE......ITQLSHLGQGTRTNVYEGRLRVEGS..GDPEEGKMDDEDPLVPGRDRGQELRVLKVLDPSHHDIALAFYETASLMSQVSHTHLAFVHGVC
    K-......L-Q-EHLGQGTRT-IY-G-LR--GD--G--EE-K.........--V-LKVLDPSHRDISLAFFEAASMMSQVSHKHLV--YGVC
         ↑JH2
         JH3
        701         711         721         731         741         751         761         771         781         791
J1  VRDVENIMVEEFVEGGPLDLFMHRKSDVLTTPWKFKVAKQLASALSYLEDKDLVHGNVCTKNLLLAREGIDSECGPFIKLSDPGIPITVLSRQECIERIP
J2  VCGEENILVQEFVKFGSLDTYLKKNSINILWKLGVAKQLAWAMHFLEEKSLIHGNVCAKNILIREEDRRTGNPFIKLSDPGISITVLPKDISSCCF.
T2  VRGPENSMVTEYVEHGPLDVWLRRERGHVPMAWKMVVAQQLASALSYLENKNLVHGNVCGRNILLARLGLAEGTSPFIKLSDPGCLGALSREERVERIP
    VRG-ENIMV-EFVE-GPLD--L-R-------WK--VAKQLASALSYLE--K-LVHGNVC-KNILLAREG------PFIKLSDPGI-ITVLSR-E--ERIP
        801         811         821         831         841         851         861         871         881         891
J1  .......WIAPECVED.SKNLSVAADKWSFGTTLWEICYNGEIPLKDKTLIEKERFYESRCRPVTPSCKELADLMTRCMNYDPNQRPFFRAIMRDINKLE
J2  QVLQERIPWVPPECIEN.PKNLTLATDKWSFGTTLWEICSGGDKPLSALDSQRKLQFYEDKHQLPAPKWTELANLINNCMDYEPDFRPAFRAVIRDLNSLF
T2  .......WLAPECLPGGANSLSTAMDKWGFGATLLEICFDGEAPLQSRSPSEKEHFYQRQHRLPEPSCPQLATLTSQCLTYEPTQRPSFATILRDLTAVQ
    W-APEC-E----NNLS-A-DKWSFGTTLWEIC--GE-PL------EKE-FYE--HRLP-PSC-ELA-L---CM-YEP-QRP-FRAI-RDLN-L--
```

FIG. 11C

```
       901              911              921              931              941              951              961              971              981              991
J1     EQNPDIVSRKKNQP........................................TEVDPTHF.KRFLKRIRDLGEGHFGKVELCRYDP.EDNTGEQVAVKSLKPESGGNHIADLKKEIEILRNLYHE
J2     TPDYELLTENDMLPNMRIGALGFSGAFEDRDPTQFEERHLKFLQQLGKGNFGSVEMCRYDPLQDNTGEVVAVKKLQH.STEEHLRDFEREIEILKSLQHD
T2     PHNLADVLTVNRDS...........................PAVGPTTFHKRYLKKIRDLGEGHFGKVSLYCYDPTNDGTGEMVAVKALKADCGPQHRSGWKQEIDILRTLYHE
       --N----V-----P------[                  ]---VDPT-F-KR-LK-IRDLGEGHFGKVELCRYDP--DNTGE-VAVK-LK---SG--H--D-K-EIEILR-LYHE
                           →JH2

1001             1011             1021             1031             1041             1051             1061             1071             1081             1091
J1     NIVKYKGICTEDGGNGIKLIMEFLPSGSLKEYLPKNKNKINLKQQLKYAVQICKGMDYLGSRQYVHRDLAARNVLVESEHQVKIGDFGLTKAIETDKEYY
J2     NIVKYKGVCYSAGRRNLRLIMEYLPYGSLRDYLQKHKERIDHKKLLQYTSQICKGMEYLGTKRYIHRDLATRNILVENENRVKIGDFGLTKVLPQDKEYY
T2     HIIKYKGCC.EDQGE.KSLVMEYVPLGSLRDYLPRHS..IGLAQLLLFAQQICEGMAYLHADYIHRDLAARNVLLDNDRLVKIGDFGLAKAVPEGHEYY
       NIVKYKG-C-EDGG----LIMEYLP-GSLRDYLPKHK---I-LKQLL-YA-QICKGM--YLG---YIHRDLAARNVLVENE--VKIGDFGLTKA-P-DKEYY 1101             1111             1121             1131             1141             1151             1161             1171             1181             1191
J1     TVKDDRDSPVFWYAPECLMQSKFYIASDVWSFGVTLHELLTYCDSDSSPMALFLKMIG.PTHGQMTVTRLVNTLKEGKRLPCPPNCPDEVYQLMRKCWEF
J2     KVKEPGESPIFWYAPESLTESKFSVASDVWSFGVVLYELFTYIEKSKSPPVEFMRMIGNDKQGQMIVFHLIELLKSNGRLPRPEGCPDEIYVIMTECWNN
T2     RVREDGDSPVFWYAPECLKEYNFYYASDVWSFGVTLYELLTHCDSSQSPPTKFLELIG.IAQGQMTVLRLTELLEAGERLPRPDKCPCEVYHLMKNCWET
       -VKEDGDSPVFWYAPECL-ESKFY-ASDVWSFGVTLYELLTYCDSS-SPP---FL-MIG----QGQMTV-RL-ELLK-G-RLPRP--CPDEVY-LM--CWE- 1201             1211             1221             1231
J1     NVSQRPSFRDLSFGWIKSGTV*
J2     QPSNRTSFQNLIEGFEALLK*
T2     EASFRPTFENSIPILKTVHEKYQGQAPSVSSVC*
       --S-RPSF-NLI-G-[       ]
                     →JH1
```

FIG. 12

```
JAK1    QNGCHGPIC-EYAI.NKLRQEGSEEGMYVLRWSCT...DFDNILMTVTCFEKSEQVQGAQKQFKNFQIEVQKGRYSLHGSDRSFPSLGDLMSHLKKQILRTDNISFMLKRCCQPKP
JAK2    HSNCHGPISMDFAI.SKLKKAGNQTGLYVLRCSPK...DFNKYFLTFAVER...ENVIEYKHCLITKNENGEYNLSGTKRNFSSLKDLLNCYQMETVRSDSIIFQFTKCCPPKP
TYK2    RDGIHGPLLEPFVQQAKLRP..LEDGLYLIHWSTS...HPYRLILTVAQRSQAPDGMQSLRLRKF.PIEQQDGAFVLEGWGRSFPSVRELGAALQGCLLRAGDDCFSLRRCCLPQP
        -GCHGPI----FAI--KLR--G-E--GLYVLRWS-------DF------K---IE-Q-G-Y-L-G---RSFPSL-DL----LQ----LR-D-I-F-L-RCC-PKP
GAP-N   WYHGKI----A----L-----GSYLIRES----PGDFVLS-------------------Y----G--R-F-SL-DL--YY--------------L-EPV
GAP-C   WYHGKLDRTIA.EERLR.QAGKSGSYLIRESDRRPGSFVLSFLSQT.NV......VNHFRI..IAMC.GDYY.IGG.RFSSLSDLIGYYSHVSCLLKGE....KLLYPV
v-Crk   WFHGKISKQEA.YNLIM.TVGQACSFLVRPSDNTPGDYSLYF.RTSENIQ..R...FKI.CPTPN.NQFM.MGG.RYYNSIGDIIDHYRKEQIVEGYY.....LKEPV
        WYWGRLSRGDA.VSLLQ..GQRHGTFLVRDSGSIPGDFVLSV.SESSRVS......HYIVNSLGPAGGRRAGGE.[18]..FDSLPSLLEFYKIHYLDTT......TLIEPV
```

PROTEIN TYROSINE KINASE

The present invention relates generally to a novel protein tyrosine kinase and to genetic sequences encoding same.

Protein tyrosine kinases (PTKs) are structurally well suited to a role introcellular signal transduction. Many growth factor receptors, for example, transduce the extracellular stimulus they receive through interaction with their cognate ligand via an intracellular tyrosine kinase domain. At least one of the non-receptor PTKs, namely LCK, is believed to mediate the transduction in T-cells of a signal from the interaction of a cell-surface protein (CD4) with a cross-linked anti-CD4 antibody.

The broader family of PTKs can be sub-divided on the basis of structural parameters of individual members. For example, the src family of PTKs now numbers 8 members (Marth et al., 1985; Nishizawa et al. 1986; Semba et al., 1986; Martinez et al., 1987; Sukegawa et al., 1987; Yamanishi et al., 1987; Hotzman et al., 1987; Dymecki et al., 1990), each with a characteristic complement of extra-catalytic domains, including an SH2, an SH3 domain and a variable ligand binding domain. It is clear that a process of gene duplication has taken place in this case, so that the evolutionarily successful thematic structure of this family can be employed in a variety of cellular contexts. Similarly PTK structural sub-families exist based around the PGF receptor and the CSF-1 receptor (reviewed in Wilks, 1990).

However, one feature in common with the aforementioned PTKs is that each kinase bears a single highly related "catalytic" domain.

In accordance with the present invention a protein tyrosine kinase is provided which is distinct from those previously known, in particular, the protein tyrosine kinase of the present invention is unique since it possesses more than one protein kinase catalytic domain. Furthermore, the kinase does not bear an SH2 domain. The novel protein tyrosine kinase of present invention represents a new sub-family or class of protein tyrosine kinase.

Accordingly, one aspect of the present invention is directed to an animal protein tyrosine kinase-like molecule comprising a polypeptide having multiple protein kinase catalytic domains but no SH2 domain.

Preferably, the polypeptide has two protein kinase catalytic domains.

Preferably, the animal is a mammal and is most preferably a human or a mouse.

Hereinafter, a protein having these characteristics will be referred to as a "JAK" (from JAnus Kinase: Janus, in Encyclopacdia Britannica (11Th Ed) Vol XV pp 155–156). The present invention is specifically exemplified using JAK1 and JAK2 from humans and mice. This is done, however, with the understanding that the present invention extends to the whole family of JAKs from all animals and to mutants, derivatives, analogues and homologues thereof. The term "protein tyrosine kinase-like molecule" (abbreviated herein to "PTK-like molecule") is used throughout the specification and claims to emphasise that the present invention encompasses all members of the JAK family and to their mutants, derivatives, analogues and homologues.

In accordance with the present invention, there is provided a PTK-like molecule. Preferably the molecule is in biological pure or in substantially pure and/or synthetic form. The purity of the preparation is characterized by a sample comprising at least 70% by weight, preferably at least 80% by weight and most preferably at least 90% by weight PTK-like molecule. Alternatively, where the purity of the enzyme preparation is not critical, the present invention also encompasses an impure PTK-like molecule preparation but which possesses a substantial amount of JAK activity.

The present invention is directed to a naturally occurring PTK-like molecule, biologically pure or substantially pure as hereinbefore defined and to derivatives, functional analogues and homologues thereof. Such derivatives include polypeptides having single or multiple amino acid substitutions, deletions and/or additions relative to the naturally occurring sequence. These derivatives, functional analogues and homologues also encompass single or multiple substitutions, deletions and/or additions to any associated molecules such a carbohydrate, lipid and/or proteinacious moieties. Reference herein to "PTK-like molecules" includes all such derivatives, functional analogues and homologues. The present invention also extends to synthetic forms of the polypeptides which include recombinant molecules and molecules prepared by the stepwise addition of amino acids to groups of amino acids in defined order.

A range of derivatives and analogues of the PTK-like molecule are contemplated herein and include altering the molecule at its nucleotide sequence-encoding level, during its expression within a cell or in vitro or post-synthesis modification. Such derivatives and analogues include, but are not limited to, modifications to side chains, incorporation of unnatural amino acids during polypeptide synthesis and the use of crosslinkers and other methods which impose conformational constraints on the polypeptide or their analogues.

Examples of side chain modifications contemplated by the present invention include modifications of amino groups such as by reductive alkylation by reaction with an aldehyde followed by reduction with $NaBII_4$; amidination with methylacetimidate; acylation with acetic anhydride; carbamoylation of amino groups with cyanate; trinitrobenzylation of amino groups with 2, 4, 6, trinitrobenzene sulphonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginic residues may be modified by the formation of heterocyclic condensation products with reagents such as 2,3-butanedione, phenylglyoxal and glyoxal.

The carboxyl group may be modified by carbodiimide, activation via O-acylisourca formation followed by subsequent derivatisation, for example, to a corresponding amide.

Sulphydryl groups may be modified by methods such as carboxymethylation with iodioacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercurlbenzoate, 4-chloromercurlphenylsulphonic acid, phenylmercury chloride, 2-chloromercurl-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole rings of a histidine residue may be accomplished by alkylation with iodoacetic acid derivatives or N-carbethoxylation with diethylpyrocarbonate.

Examples of incorporating unnatural amino acids and derivatives during polypeptide synthesis include, but are not limited to, use of norleucine-4-amino butyric acid, 4-amino-3-hydroxy-5-phenylpentanoic acid, G aminohexanoic acid, t-butylglycine, norvaline, phenylglycine, ornithine, sarcosine, 4-amino-3 hydroxy-6-methylheptanoic acid, 2-thienyl alanine and/or D-isomers of amino acids.

Crosslinkers can be used, for example, to stabilise 3D conformations, using homo-bifunctinoal crosslinkers such as the bifunctional imido esters having $(CH_2)_n$ space groups with n=1 to n=6, glutaraldehyde, N hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, polypeptides could be conformationally constrained by, for example, incorporation of $C_a$ $N_a$-methylamino acids, introduction of double bonds between $C_a$ and $C_B$ atoms of amino acids and the formation of cyclic polypeptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof corresponding to regions of PTK-like molecules. Preferably, the PTK-like molecules will retain JAK activity. However, molecules carrying mutations in the catalytic domains rendering these inactive may be useful in, for example, titrating out activity and generation of antibodies such molecules are encompassed by the present invention.

The molecular weights of the PTK-like molecules of the present invention range from 100,000 to 200,000 daltons and preferably from 120,000 to 150,000 daltons.

In a most preferred embodiment, the present inventions provides JAK1 and JAK2. JAK1 is an approximately 1142 amino acid molecule with a molecular weight of about 132,000 daltons and a nucleotide sequence shown in FIG. 2, JAK2 is an approximately 1,000 amino acid molecule with a molecular weight of about 130,000 daltons and with a nucleotide sequence shown in FIG. 8.

The present invention is also directed to genetic sequences including DNA, cDNA and mRNA which encode the PTK-like molecules hereindescribed. Such genetic sequences include single or multiple nucleotide substitutions, deletions and/or additions relative the naturally occurring sequence and extend to sequences encoding the derivatives, functional analogues and homologues of the PTK-like molecules. The present invention also provides these genetic sequences in vector and expression vector systems either in vitro or in a biological system (i.e. eukaryotic or prokaryotic cells) transformed with such vectors or genetic sequences. In a most preferred embodiment the present invention provides cDNA encoding JAK1 and JAK2 as set forth in FIGS. 2 and 8, respectively. A range of mutants can be obtained using standard techniques such as an oligonucleotide mutagenesis and chemical mutagenesis, and all such mutants and derivatives are encompassed by the present invention.

The present invention also provides antibodies to a PTK-like molecule. Such antibodies may be monoclonal or polyclonal.

The PTK-like molecule of the present invention have varying utility such as in the phosphorylation of proteins, incorporation of labels and in the design of analogues, antagonist and agonists of JAKs.

Accordingly, another aspect of the present invention contemplates a method for phosphorlyating a protein comprising containing said protein with a phosphorylating effective amount of a PTK-like molecule, said molecule comprising a polypeptide having a multiple protein kinase catalytic domains but no SH2 domain for a time and under conditions sufficient for said first protein to be phosphorylated. Preferably, the polypeptide has two protein kinase catalytic domains and most preferably is JAK1 and/or JAK2 and/or their derivatives.

The present invention is further described by reference to the following non-limiting Figures and Examples.

Figure 1B:
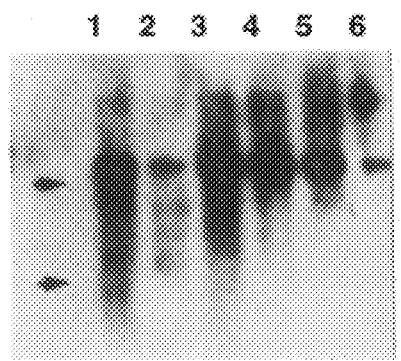

In the Figures:

FIGS. 1A and 1B are a photographic representation of a Northern analysis of murine and human JAK1.

FIG. 1A. 2 μg aliquots of poly(A)+ mRNA from murine tissues: lane 1, lung: lane 2, liver; lane 3, kidney; lane 4, intestine; lane 5, brain; lane 6, skeletal muscle; lane 7, spleen; lane 8, slivary gland; lane 9, placenta; lane 10, mammary gland, were fractionated on a 1.0% agarose/formaldehyde (Moran et al. 1988) gel and the RNA transferred onto a Genescreen plus (Dupont) membrane. The transferred RNA was hybridized with a 1.8 kb $^{32}$P-labelled murine JAK1 probe and the filter autoradiographed for 16 hr. at −70° C. with two intensifying screens. The relative mobilities of 28S rRNA (upper arrow) and 18S rRNA (lower arrow) are shown.

FIG. 1B. 2 μg aliquots of poly(A)+ mRNA from the human haemopoictic cell lines; lane 1, IIL60 (myelomonocytic); lane 2, U937 (monocytic): lane 3, LK63 (pre-B): lane 4, RAJI (B-cell): lane 5, CEM (T-cell): lane 6, K562 (erythroleuknemia) were fractionated on a 1.0% agarose/formaldehyde (Moran et al., 1988) gel and the RNA transferred onto a Genescreen plus (Dupont) membrane. The transferred RNA was hybridized with a full-length $^{32}$P-labelled human JAK1 probe and the filter autoradiographed for 16 hr. at −70° C. with two intensifying screens. The relative mobilities of 28S rRNA (upper arrow) and 18S rRNA (lower arrow) are shown.

FIG. 2 is a representation showing nucleotide sequence and predicted amino acid sequence of human JAK1. The DNA sequence is numbered at the end of each line of sequences from the first nucleotide of the largest clone (pTIJ7.3), the amino acid sequence (in one letter code) is numbered from the putative AUG and appears above the line to which it refers. The two kinase catalytic domains are boxed with arrows, and kinase consensus motifs are enumerated according to the nomenclature of Hanks et al (1988). The suffix a (e.g. IIa) denotes the kinase related motifs present in the first kinase related domain (designated domain-1 in FIG. 3a) also numbered according to the same nomenclature. The tyrosine residue in an analogous position to the autophosphorylation site of a number of other protein tyrosine kinases is marked with an inverted triangle.

FIGS. 3A and 3B are a representation showing:

FIG 3A. Amino-acid sequence comparison of the two kinase-related domains of JAK1. The amino-acid sequences (expressed in one-letter amino acid code) of the two kinase-related domains (domain-1 amino-acids 576–825; domain-2 (PTK-domain) amino-acids 868–1139) of JAK1 and the human threonine/serine-specific kinase CDC2 (24) (amino acids 9-272) are aligned in order to maximize identity. The kinase-related domains have been divided into three segments and the number of amino acid residues separating each segment appears at the end of each line. Motifs held in common between at least two of these domains are both bolded and boxed. Roman numerals above the alignment correspond to the conserved domain nomenclature devised by Hanks et al (1988).

FIG. 3B Hydropathy plot of the human JAK1 protein. The protein sequence of human JAK1 (including the 10 extra amino acids which precede the most likely initiation codon) were analysed by the hydrophilicity algorithm of Kyte and Doolittle (1982) using a span length of 25 amino acids. The relative locations of the two kinase related domains are marked as Domain-1 and PTK. The absence of a hydrophobic transmembrance domain is clearly seen, as can the presence of a highly hydrophilic region between amino acids 323 and 350.

Figure 4A:
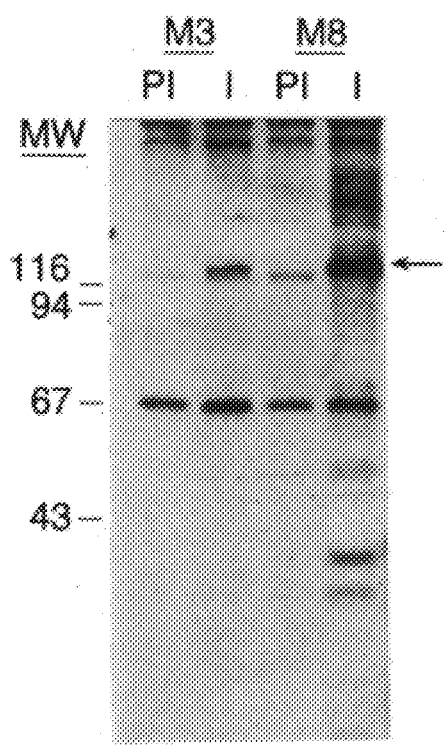
Figure 4B:
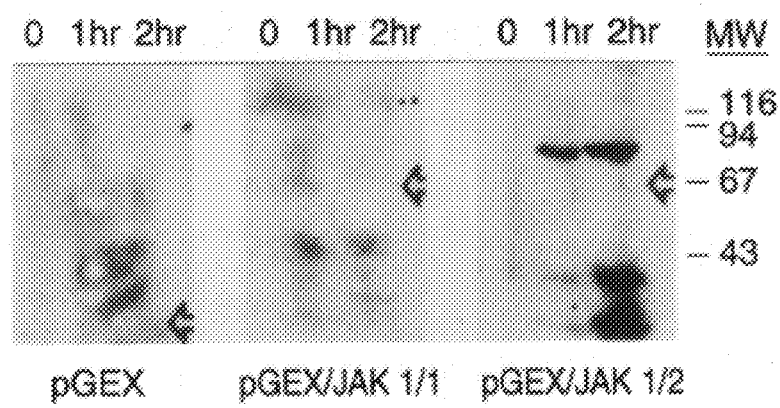
Figure 4C:
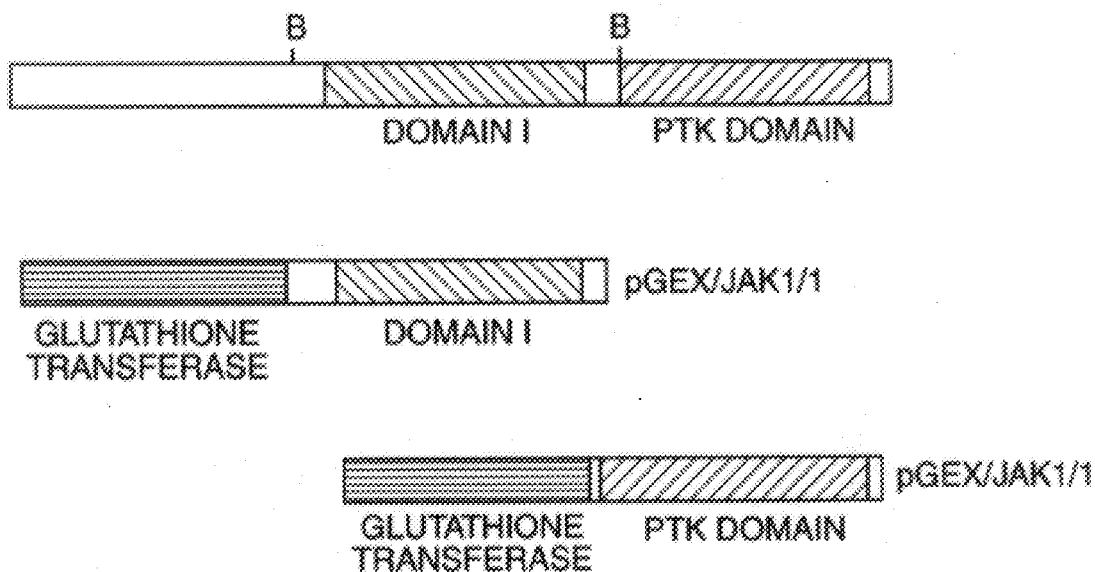

FIGS. 4A–4C are a representation of an analysis of the JAC1 protein.

FIG. 4A. Cellular proteins of the murine mammary fibroblast cell line (17) were labelled with $^{35}$S-methionine (panel A) and immunoprecipitated with either pre-immune (PI) or immune (I) anti-JAK rabbit antiserum (raised in rabbit M8 against the pGEX/JAK1/1 fusion protein or the C-terminal peptide [M3]) and fractionated on a 9.5% SDS-PAGE gel (Laemmil, 1970). Both rabbit antisera specifically immunoprecipitated an $^{35}$S-labelled protein of apparent of apparent molecular weight 130,000D.

FIG. 4B. Demonstration of tyrosine kinase activity in JAK1 bacterial fusion proteins. JAK1 fusion proteins were generated using pGEX2 (Smith and Johnson, 1988). The entire domain-1 region was included in construct pGEX/JAX1/1. The PTK domain portion of the fusion protein extended to the BamHI site 15 nucleoides 5' of the first glycine codon of the GXGXXG motif (SEQ ID. No: 3) of the ATP binding site. An empty vector control was also performed. The bacteria were induced by the addition of 1 mM. IPTG as described by Smith and Johnson (1988) and two 1 ml aliquots of the bacteria were removed at 60 minutes and 120 minutes post-induction and lysed with SDS sample buffer. Western analysis of the samples was performed using anti-phosphotyrosine antisera (PY-20 [ICN]). The arrow heads mark the positions of the GEX-JAK fusion proteins, in each induction.

FIG. 4C. Construction of the pGEX/JAK fusion proteins. The locations of the two kinase related demains of JAK1 are shown, and below, the structure of the fusion proteins with the glutathione S. transferase gene.

FIG. 5 is a representation of a sequence comparison between JAK1 and JAK2 kinase-related domains. The deduced amino acid sequence of murine JAK2 was compared to the human JAK1 amino acid sequence by application of an alignment programme of the Staden VAX-based suite of Sequence analysis programmes. Asterisks (*) denote identity, dollar signs ($) denote conservative substitutions. Sequences are numbered with respect to the JAK1 sequence. The extent of the domain-1 are PTK domains is shown by arrows above the amino acid sequence.

Figure 6:
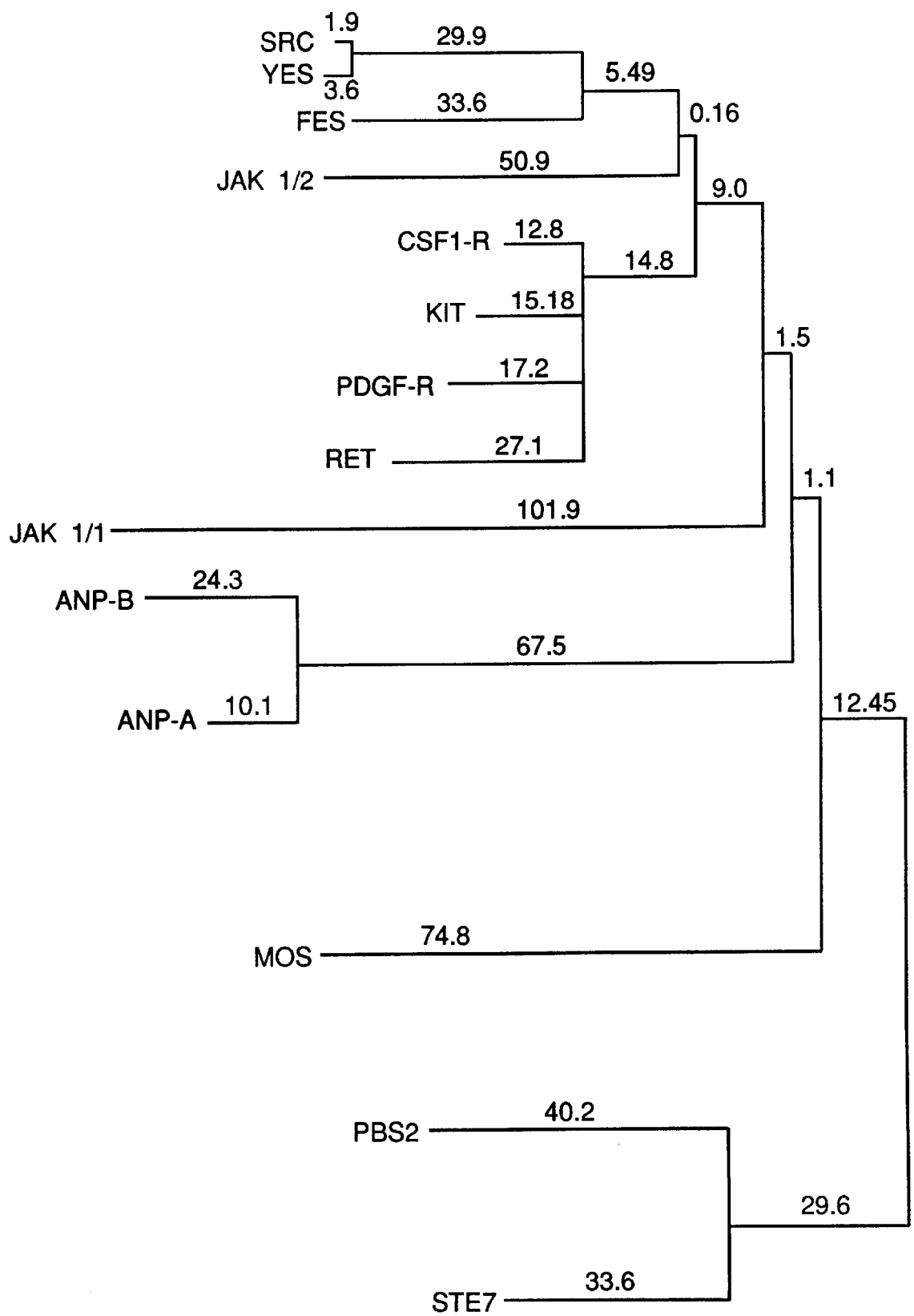

FIG. 6 is a graphical representation of a phylogenetic analysis of the two JAK1 Kinase-like domains. The tree building concept of Fitch and Margoliash (1967) as implemented by Feng and Doolittle (1987) and Hanks et al. (1988) was used to generate a phylogenetic tree as described in Example 1. In each case the catalytic domain alone was used for comparison. The two kinase related domains of the JAK1 protein were compared independently. Branch order is a function of structural similarity, branch length a function of sequence identity. The abbreviations used are: SRC=c-scr; YES=c-Yes; FES=c-fes; CSF1-R=Colony stimulating factor-1 receptor; KIT=c-kit; PDGF-R=Platelet derived growth factor receptor-A; RET=c-RET; ANP-A=Atrial naturetic peptide receptor-A; ANP-B=Atrial naturetic peptide receptor-B; MOS=c-mos; PBS2=polyxinn B antibiotic resistance gene product; STE7=sterile mutant wild-type allele gene product; JAK1/1=Domain-1 of Human JAK1; JAK1/2=PTK domain of Human JAK1.

Figure 7A:
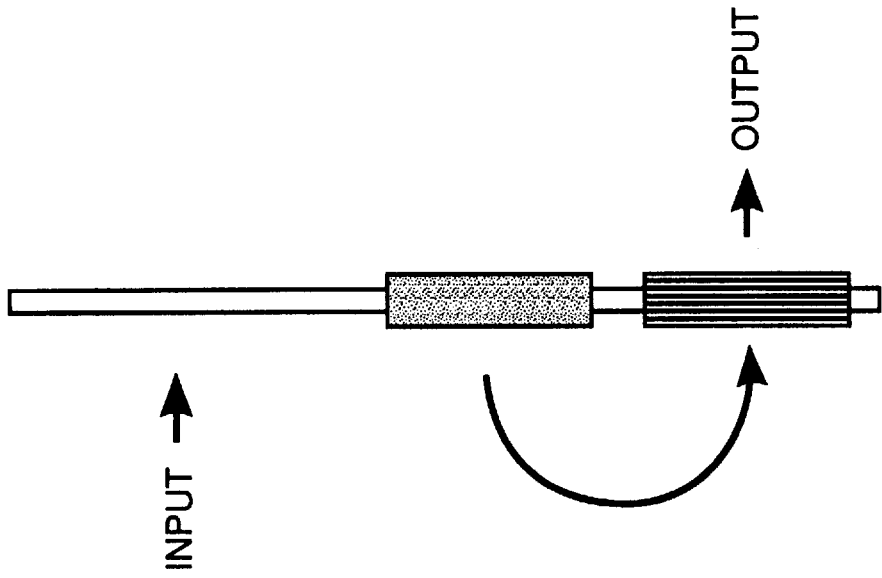
Figure 7B:
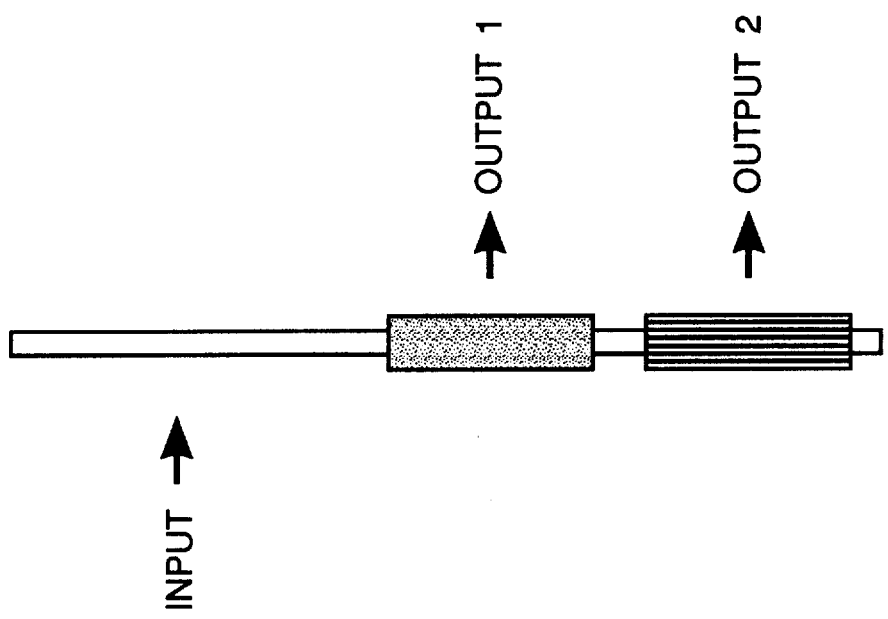

FIG. 7 is a diagramatic representation showing models for the rule of members of the JAK family of PTKs in signal transduction. Two possible scenarios are considered based on an extrapolation of the current notions of the role of PTKs in signal transduction. In panel A the N-terminal domain of the JAK protein serves to sense a particular metabolic cue and convert this input into two distinct outputs. Presumably the output of the second PTK-related domain is tyrosine kinase activity; the activity of Domain-1 remains unknown. In panel B an alternative scenario is considered. In this case the function of Domain-1 is the regulation of the PTK domain. In this scenario the sole output of the JAK protein is the PTK activity.

FIGS. 8A and 8B are a representation of a nucleotide sequence and predicted amino acid sequence of murine JAK2. The nucleotide sequence is numbered beneath each line of sequence, from the first nucleotide of the most 5' clone. The predicted amino acid sequence, in one letter code, is numbered at the end of each line of sequence. The two putative kinase domains are shown boxed with arrows, and the kinase consensus motifs are enumerated according to the nomenclature of Hanks et al (1988). The subscript a denotes the kinase-related motifs present in the first kinase-related domain, which are numbered according to the same nomenclature.

Figure 9:
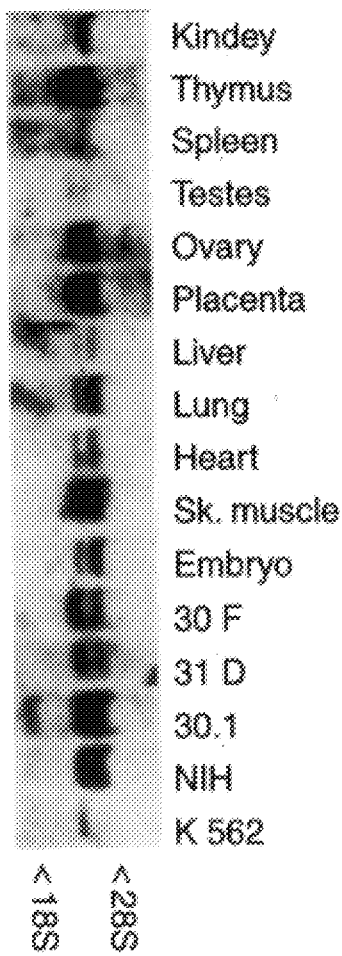

FIG. 9 is a photographic representation showing expression of JAK2 in murine tissues. Northern blot analysis of 5 μg of mRNA from each of the tissues shown on top of the figure and from various murine (30F: mammary fibroblasts; 31A: mammary epithelial cells; 30.1; factor independent subline of the hemopoietic cell line FDC.Pl; N1H: fibroblasts) and human (K562; chronic myclogenous leukaemic cells) cell line. The blots were hybridized with a $^{32}$P-labelled 2.2 kb JAK2 probe and autoradiographed was for 4 days. The relative mobilities of the 28S and the 18S rRNA are indicated.

Figure 10:
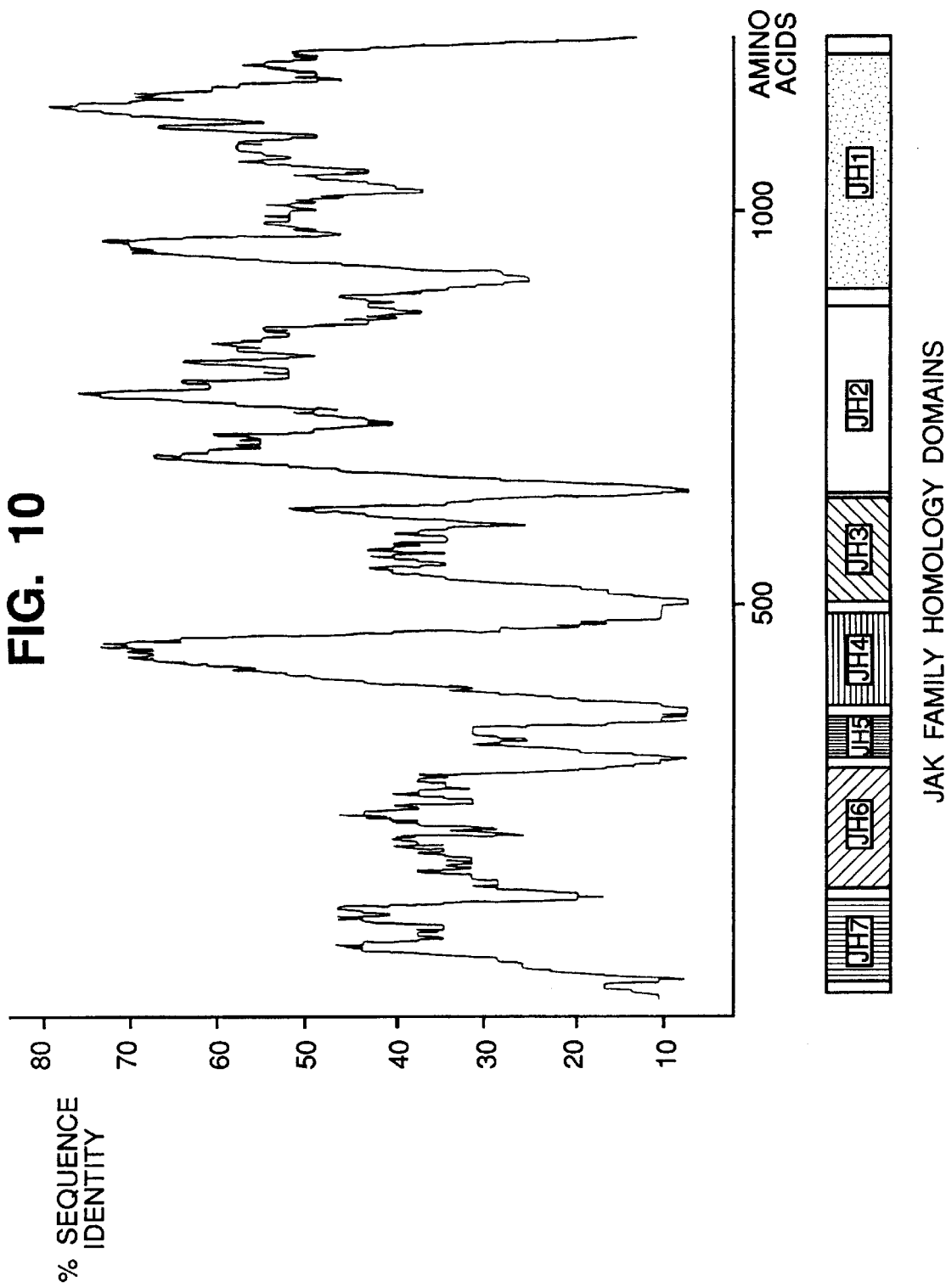

FIG. 10 is a graphical representation showing comparison of JAK1 and TYK2 amino acid sequences. The amino acid sequences of JAK1 (Wilks et al, 1991) and TYK2 (Firmback-Kraft et al, 1990) were compared using the HOMOLOGY option in the programme SEQMATCH, using a window length of 21 amino acids. The ordinate of the graph represents the percentage identity between the two sequences, the abscissa represents the amino acid position in JAK1 at which the particular level of identity was calculated. The shaded boxes below the graph represent arbitrarily ascribed JAK homology domains as discussed in the test and further demonstrated in FIG. 11.

FIG. 11 is a representation showing amino acid sequence comparison of members of the JAK family of PTKs. The aminoacid sequences of JAK1 (Wilks et al, 1991) (designated J1 in this figure), JAK2 (J2 in this figure), and TYK2 (Firmback-Kraft et al., 1990) (T2 in this figure) were aligned using the CLUSTAL program (Higgins and Sharp, 1988). The numbering system is relative only to the first amino acid of JAK1, and does not take into account the insertion of gaps into this sequence; it is therefore useful only as a relative measure of location. The extent of each of the JAK homology domains was determined with reference to the homology plot shown in FIG. 10. Amino acid positions conserved in at least 2 our the 3 sequences presented are bolded and presented below the TYK2 sequence as a consensus sequence.

FIG. 12 is a representation showing a comparison of the JH3/JH4 domain region with SH2 domains. The two SH2 domains of GAP (the more N-terminal domain denominated GAP-N (residues 178–269), the more C-terminal, GAP-C, (residues 348–438) (Trahey et al, 1988), and the SH2 domain of work (residues 248–354) (Mayer et al, 1988) were compared with the JH3/JH4 of JAK1 (residues 425–536) (Wilks et al, 1991), JAK2 (residues 252–359) (this manuscript) and TYK2 (residues 449–555) (Firmback-Kraft et al, 1990). Amino acids held in common between the two classes of sequence are denoted by vertical lines between the two sets of sequences. Conserved residues held in common by members of the same class of domain are bolded.

EXAMPLE 1

Materials and Methods

Screening of cDNA libraries

Several cDNA libraries were screened according to the protocols outlined in Maniatis et al, (1982). cDNA libraries from Murine NFS TPA activated spleen (Clontech cat. #ML1018), murine swiss-albino 3T3 fibroblast (Clontech cat.#1023b), murine balb/c bone marrow (Blontech cat.#ML1007), murine swiss-webster whole brain (Blontech cat.#ML1002), murine ICR linoleic acid activated pleural macrophage (Clontech cat.#ML1005b), and human 1st-trimaster foetal liver (Clontech cat.#HL1005b) were all generated in λgt 11. cDNA libraries from murine Balb/c testis (Clontech cat.#ML1020b), murine day 10 embryonic neuro-epithellum (Reid et al, 1990) and human foreskin fibroblast cell line AG1518 (Claesson-Welsh et al, 1989) were generated in λgt10. Around $10^6$ recombinants of each of these libraries were screened on each occasion.

Library screening was carried out as follows. The FD22 (JAK1) PCR clone was labelled by nick-translation (Maniatis et al, 1982) and used to screen the murine libraries. A murine cDNA clone of 1.8 kb was isolated amongst 3 other positives from the neuro-epithelial and bone marrow cDNA libraries. Two full-length human JAK1 cDNA clones were isolated from the unamplified human foreskin fibroblast cell-line AG1518 by using the murine cDNA as a probe. Hybridisation was at 65° C. in 6xSSC; 1% SDS; 0.5% Blotto; 200 µg/ml sonicated and denatured herring sperm DNA. After hybridisation, the stringency of the final wash was 0.2xSSC; 0.1% SDS at 65° C. Filters were autoradiographed overnight using Kodak XAR-5 X-ray film.

For JAK2, the murine macrophage was screened first with the FD 17 (JAK2) PCR clone, Yielding 5 positives, and a portion of the longest cDNA clone isolated and used to screen the remaining cDNA libraries. Hybridisation conditions were as above for JAK1.

DNA sequencing

Two strategies were employed for the sequencing of JAK1 and JAK2 cDNA clones. In the case of the human JAK1 sequence, the Erase-a-Base kit (PROMEGA) was employed to generate nested deletions of the largest EcoRI fragment. All of the murine JAK2 sequence data, and the remainder of the human JAK1 sequence, was determined using oligonucleotide primers based on previously determined DNA sequence. In each case the sequence information was generated using the dideoxynucleotide chain termination method (Sanger et al, 1977). All sequence information was determined on both strands.

Northern Analysis

Poly A+ mRNA samples were prepared as elsewhere described elsewhere (Wilks and Kurbon, 1988). Aliquots (1 µg) were analysed by electrophoresis on a 1% agarose gel containing 2.2M formaldehyde; 20 ml MOPS, pH 6.8; 1 mM EDTA; 5 mM sodium acetate, and transferred to Hybond (Amersham, cat #RPN303N) or nitrocellulose (Schleicher & Schuell, HA85, cat #401196) membranes. Filters were pre-hybridised for 4 hr in 50% formamide containing 3xSSC, 5xDenhardts; 10 mM HEPES pH 7.0; 100 µg. ml 1; poly C; 100 µg/ml denatured herring sperm DNA; 10 µg/ml E. coli DNA; 0.1% SDS, and hybridised in the same solution with nick-traslated $^{32}$P-labelled murine or human JAK1 or JAK2 insert, for 18 hr. at 42° C. Filters were washed to a final stringency of 0.2xSSC; 0.1% SDS at 65° C., before exposure to Kodak XAR-5 X-ray film, with two intensifying screens.

Antibody Reagents and Protein Analysis

Polyclonal rabbit antisera M7 and M8 were raised against affinity purified pGEX/JAK1/1 bacterial fusion protein (see section on kinase assays). Polyclonal antibodies M3 and M4 against the C-terminal peptide (-TSFQNLIECFEALLKC-) (SEQ ID No:4) of JAK1 were raised in rabbits. Peptide was coupled in Keyhole Limpet Heamocyanin with 0.05% gluteraldehyde, emulsified in Frends' complete adjuvant and injected intradermally at several sites. The animals were boosted four and seven weeks later with coupled peptide emulsified in Freunds' incomplete adjuvant and bled ten days after the last injection.

Cells were metabolically labelled with either $^{35}$S-methionine or $^{32}$P-orthophosphate in methionine- or phosphate-free medium containing 100 µCi/ml and 1 mCi/ml isotope respectively. RIPA-buffer (20 mM Tris, pH7.5 containing 1% Triton X100, 1% Na deoxycholate, 0.1% SDS, 1 mM EDTA, 1 mM PMSF) extracts were incubated on ice with antiserum and immune-complexes isolated using Protein A bearing Staphylococus aureus bacteria. Proteins were resolved by SDS-PAGE (Laemmli, 1970) and radio-actively labelled bands detected by exposure to X-ray film (Kodak XAR-5). The RPTA buffer for $^{23}$P-labelled calls contained in addition 20 mM EDTA, 10 mM NaF, 100 µM orthovanedate as phosphatase inhibitors.

Phosphoamino-acid analysis of excised $^{32}$P-labelled bands was carried out exactly as described by Hunter and Sefton (1980) Western blot analysis was performed as described by Towbin et al. (1979) as modified in Ziemiecki et al (1990) using either alkaline phosphatase or $^{125}$I-labelled protein-A as a detection system.

Protein Kinase Assays

A variety of protocols have been tried in order to reveal the PTK activity of the JAK1 protein. First, extraction of murine mammary fibroblasts, Reichmann et al (1989) has been performed in a range of buffers, containing Triton-X100 or Nonidet P40 (1.0%) alone, or with added Sodium Deoxycholate (0.5% or 1.0%) or in RIPA buffer (containing 1.0% Triton-X100; 1.0% Sodium Deoxycholate; 0.1% Sodium Dodecylsulphate). Cells have been extracted in the presence or absence of phosphates inhibitors, such as 20 mM EDTA, 10 mM NaF and 100 µM Na2V04.

After immunoprecipitation, kinase assays have been performed in a range of ATP concentrations (100 nM-10 mM) or with carrier-free γ-35P-ATP (Amersham cat #10169) in either 20 mM Tris, pH 7.4 or 50 mMM HEPES PII 7.4, with either 10 mM Mn$^{++}$, Mg$^{++}$ or Zn$^{++}$ as divalent cation. Incubations have been performed on ice (15 min), at 250° C. (15 min), at 30° C. (15 min) or at 37° C. (2 min) in the presence or absence of the phosphatase inhibitor Na2V04. Finally, γ-32P-GTP was employed as phosphate donor in lieu or γ-32P-ATP, with no success.

In order to generate the JAK1glutathione transferase fusion proteins shown in FIG. 4, domain-1 (from nucleotides 1770–2672 in FIG. 2) and the PTK domain (from nucleotides 2672-end in FIG. 2, thus including 5 extra amino acids beyond the ATP binding glycine motif) were each fused into the BamHI site of pGEX2. The fusion protein was induced by the addition of 1 mM IPTG as described elsewhere (Smith and Johnson, 1983) and Western blot analysis performed on an induction time course with the M3 anti-JAK1 serum, and the anti-phosphotyrosine antiserum (Kamps and Sefton, 1988). Several sources of anti-phosphotyrosine antisera were tried. The data in FIG. 4b were obtained using a commercially available monoclonal antibody preparation PY-20 (ICN). In control experiments, induction of the insert-less pGEX or pGEX/JAK1 fusion protein produced no detectable tyrosine phosphorylation of bacterial substrates and the reactivity of the anti-phosphotyrosine antiserum could be completely abolished by the additional of phenyl phosphate.

Computer Aided Sequence Analysis

Amino acid sequence comparisons were performed using an alignment programme from the Staden-based suite of programmes on a VAX VMS 5.2. The phylogenetic analysis of the two kinase-like domains of JAK1 was performed using the tree-building concept of Fitch and Margoliash (1967) as implemented by Feng and Doolittle (1987). The SCORE programme used to construct the difference matrices from which the trees were derived using the BORD AND BLEN programmes, were all the gift of Dr. R Doolittle of the University of California—San Diego.

The sequence alignment shown in FIG. 11 was assembled using the CLUSTRAL program (Higgins and Sharp, 1988) on a VAX VMS 5.2 minocomputer. The homology plot shown in FIG. 10 was assembled using the HOMOLOGY option of the programme SEQMATCH. Database searches with each of the JAK homology domains was reformed using the PASTA programme, based on the Pearson/Lippman algorithm (Pearson and Lippman, 1988).

Rack/Anchor PCK

RACE/Anchor PCR (Frohman et al., 1990; Loh et al., 1990) was performed by a modification of the original protocol. Briefly, 2 µg of poly(A+) mRNA is converted to cDNA using an Amersham cDNA synthesis kit (cat No. RPN 1256) and 40 ng. of a JAK2 specific oligonucleotide primer (5' TACACCTTTAAATATTTTTGT-B') (SEQ ID. No: 5). Prior to the addition of the reverse transcriptase, the reaction mixture was heated to 65° C. cDNA synthesis was initiated by the addition of 20 units of reverse transcriptase, and the reaction incubated at 55° C. for 75 minutes. The newly sunthesised cDNA was recovered by passage through a spun sephadex column (Maniatis et al. 1982) followed by ethanol precipitation. The mRNA/cDNA, heteroduplex was G-Tailed in 30 µl containing 140 mM potassium cacodylate, 30 mM Tris, (pH 7.2). 1 mM $CoCl_2$, 0.1 mM DTT, 6 mM dGTP and 15 units of TdT (1BI), for 10 minutes at 37° C. The reaction was terminated by heating to 65° C. for 15 minutes and then diluted to 500 µl with 10 mM Tris. HCl (pH7.5). 1 mM EDTA. For the RACE/Anchor PCR, 10 µl of the tailed cDNA was reconstituted into 100 µl PCH buffer (50 mM KCl, 10 mM Tris. HCl[pH8.3], 1.51 mM $MgCl_2$, 0.01% gelatin, 200 µM of each dNTP) to this was added 50 mg of "poly-C" oligonucleotide primer (5'-CTCGAGTCGACGAATTC$_{14}$-3') (SEQ ID No: 6) and 2.5 units of TAQ polymerase (Cetus). the complementary strand of the cDNA was synthesised with one cycle of 95° C. (5 minutes), 52° C. (5 minutes) and 68° C. (40 minutes), whereupon 500 µg of the "RACE/Anchor" primer (5'-CTCGAGTCGACGAATTC-3') (SEQ ID. No: 7) and a nested JAK2 specific primer (5'-CTTGCTTAATACTGACATCA-3) (SEQ ID. No: 8) were added and the reaction mix subjected to 30 cycles of 95° C. (1 minute), 52° C. (2 minutes) and 68° C. (5 minutes). The PCR product was phenol/chloroform extracted, precipitated and resuspended in 100 µl of water. The amplified material was then kinased, size fractionated on a low-melting temperature agarose gel and cloned into SmaI cleaved M13mp8. Plaques were screened by hybridisation with a JAK2 cDNA, and positives sequenced.

EXAMPLE 2

Isolation and DNA sequencing of cDNA clones encoding JAK1

JAK1 cDNA was cloned using PCR. Northern analysis (FIG. 1a and b) demonstrated that in both mouse and human tissues and cell lines FD22 (JAK1) was encoded by a single widely expressed 5.4 kb mRNA. Human cDNA clones of FD22 (JAK1) were isolated from a human foreskin fibroblast cell line (AG 1518) cDNA library (Claesson-Welsh et al., 1989). Two of the 8 primary isolates cloned contained inserts which were candidates for being full-length cDNAs (−5.3 kb).

The nucleotide sequence of human JAK1 is shown in FIG. 2. The 5' end of the clone has stop codons in all 3 reading frames prior to the putative initiation ATG. Two ATG start codons in frame with the longest open reading frame were found at positions 40 and 76 in the nucleotide sequence shown in FIG. 2. The first of these is embedded in a particularly poor. "Kozak" consensus sequence (Kozak, 1984) (-TAAATGCAC-) (SEQ. ID. No: 9) whereas the second matches strongly with the optimal consensus sequence defined by Kozak, namely -GCCATGGCT (SEQ. ID. No: 10). The second ATG is considered to be the initiation codon for this protein, since the first one transgresses one of the strongest correlations found in the sequences which precede initiation codons, namely the presence of a T residue (in lieu of an A residue) 3 nucleotides before the ATG sequence. At the 3' end, an in-frame stop codon at position 3502 defines the C-terminus of the protein. A large (1.405 kb) 3' untranslated region containing a polyadenylation signals completes the mRNA sequence.

The JAK1 coding region of 3426 bp encodes a protein of 1142 amino-acids with a calculated molecular mass of 132,000 daltons. The PTK catalytic domain is located towards the C-terminus of the JAK1 protein (FIG. 2). In describing the structural features of this domain we have chosen to adopt the nomenclature of Hanks et al (1988). The putative ATP binding the site composed of the motif GLY-X-GLY-X-X-GLY-Y (SEQ. ID. No: 3) (subdomain 1) followed by an invariant lysine residue (subdomain II) is located between amino acid residues 871 and 896 of the JAK1 protein. The core motifs of the PTK catalytic domain (sub-domains VI to IX) are also in their appropriate locations, and are well conserved with respect to their primary sequence and their relationship to each other. The presence of a tyrosine residue at position 1022 in the JAK1 protein, 11 residues C-terminal to sub-domain VII (a similarly placed tyrosine is a site of tyrosine autophosphorylation in v-fps; Weinmaster et al., 1984) is a consistent feature of members of the PTK family and is considered diagnostic of membership of this class of kinases. The arginine residue at position 1126 (domain XI) marks the end of the highly conserved regions of the PTK catalytic domain and the entire catalytic domain of 255 amino acids is approximately 28% (with c-fes; Wilks and Kurbon, 1988) to 37% (with TRK; Korman et al, 1988) identical to other functionally defined PTKs. Finally, there is a rare variant of the highly conserved subdomain VIII motif (residues 1032–1039), which is believed to lie close to the active site (Hanks et al, 1988). The presence of phenylalanine and tyrosine flanking the conserved tryptophan in this motif is unique to JAK1 and JAK2.

A second protein kinse-related domain (designated here Domain-1) is located between amino acids 578 and 824, 47 amino acids N-terminal to the putative PTK domain. All of the conserved elements of protein kinases are preserved spatially in this domain. In FIG. 2 these elements are numbered with respect to their similarity to the subdomains of protein kinases described by Hanks et al, (1988) (with the suffix$_a$, e.g. III$_a$) and the amino acid sequences of the two kinases-related domains of JAK1 are compared to each other and to human CDC2 (Lee and Nurse, 187) in FIG. 3a. The overall structural similarity of this domain to the kinase domains of both the PTK and threonine/serine kinase families strongly suggest that this region of the protein also functions as a protein kinase. There are, however, significant differences in the sequences of key motifs within this domain which suggest that Domain-1 may confer a catalytic activity other than serine/threonine or tyrosine phosphorylation. For example, sub-domain VI$_a$ is poorly conserved with respect to the equivalent motifs in the outer kinase families, and the normally invariant -ASP-PHE-GLY- sequence of the PTK and threonine/serine kinase families (sub-domain VII$_a$) is replaced by the motif ASP-PRO-GLY- in Domain-1 of JAK1. As has been noted elsewhere, the conservation of the precise sequence of sub-domain VI in the PTK and threonine/serin kinase families appears to correlate with the substrate specificity of the kinase. Thus, it is possible that Domain-1 of the JAK1 kinase has a substrate specificity other than that exhibited by the PTK and threonine/serine kinase has a substrate specificity other than that exhibited by the PTK and threonine/serine kinases. In support of this notion there are subtle differences in the normally consistent spacing between certain key motifs in Domain-1 of JAK1. The components of the ATP binding site (sub-domains I$_a$ and II$_a$) are some 7 amino acids further apart in this domain that they are in both the PTK family and the threonine/serine kinase family. Moreover, the spacing between sub-domains VI$_a$ and VII$_a$ in this region is also longer by 9 amino acids. Conversely, the distance between sub-domains VII$_a$ and IX$_a$ is 7 amino acids shorter than the corresponding region in the PTK catalytic domain. The overall structure of this domain can be expected to be somewhat different to the catalytic domains of the members of the PTK and threonine/serine kinase families.

The sequences N-terminal to Domain-1 bear no homology to any other portion of a previously described protein kinase. Specifically, no homology was detected to the SH2 domain described for the cytoplasmic PTKs such as c-fex/fps. (Sadowski et al, 1986) GAP (Trahey et al, 1988) and the phospholipase-C family of proteins (Suh et al, 1988). This is a particularly interesting observation since no other non-receptor PTK has been described which lacks this feature. A hydrophilicity plot failed to demonstrate the present of a hydrophobic domain characteristic of the growth factor receptor type of PTK (FIG. 3b) suggesting that this protein is wholly intracellar like, other members of the non-receptor class of PTKs. The one outstanding feature of the JAK1 hydropathy plot is the highly hydrophilic sequence between residues 320–350. This sequence is not conserved in the murine JAK2 protein, however, its remarkable nature suggests that it may well be involved in some function of the JAK1 protein.

Expression of JAK1 protein

Several antisera were generated against the human JAK1 protein. Polyclonal antisera directed against the hexadecamer -TSFONLIECFEALLKC- (SEQ ID No: 4) (the C terminal 15 amino acids of JAK1) were raised in rabbits and used to investigate the nature of the JAK1 protein. A second rabbit antiserum was generated using a pGEX bacterial fusion protein containing the entire Domain-1 region of the human JAK1 protein (see Example 1). Preliminary sequence analysis of cDNA clones of murine JAK1 demonstrated that the C-terminus of the human and murine versions of this protein were identical whereas the murine and human Domain-1 regions exhibited a very high degree of identity. Both systems have thus been used interchangeably in the investigation of the properties of the JAK1 protein.

Both antisera have been used for Western blot analyses and immunoprecipitation studies and the data confirm the mRNA expression studies shown in FIG. 1. For example, antisera M3 and M8 both immunoprecipitate a protein of the same apparent molecular weight (130 kDaltons) from $^{35}$S-methionine labelled murine breast fibroblasts (FIG. 4a). From the same source, $^{32}$P-orthophosphate labelled JAK1 was immunoprecipitated as a phosphothreonine and phosphoserine containing phosphorprotein. It is a feature characteristic of members of the protein tyrosine kinase family that they are able to accomplish an act of self phosphorylation in vitro. Intriguingly, despite the high degree of sequence similarity held by the PTK-related sequence of JAK1 to the PTK family in general, it was not possible to demonstrate tyrosine kinase catalytic activity in immunoprecipitates of this protein from any of the murine or human sources tested. A wide range of possibilities has been tested in search of suitable conditions for the demonstration of this activity. These are listed in Example 1. The reason for the lack of activity may lie with a steric effect of the antibody in the active site of the enzyme.

In order to determine whether domain 1 or the PTK domain, in isolation, bore catalytic activity, bacterial fusion proteins of each were generated with the glutathione transferase protein of *Schistosoma japonicum* (Smith and Johnson, 1988) and an attempt was made to demonstrate with the aid of anti-phosphotyrosine antibodies (Kamps and Sefton, 1988) the co-ordinate induction of the fusion protein and tyrosine phosphorylated protein. In this system there is no cross-reactive background of the anti-phosphotyrsine antiserum, since there are not tyrosine kinases in bacteria (FIG. 4b). The phosphorylation of bacterial proteins on tyrosine is thus easily detectable with such a serum. In this series of experiments neither pGEX without insert nor pGEX bearing Domain-1 (pGEX/JAK/1/1) demonstrated any tyrosine kinase activity. The pGEX/JAK/1 fusion protein was further purified by affinity chromatography on a reduced glutathione column and have failed to detect any kinase activity using either histones, casein or enolase as an exogenous substrate. The pattern of inducible tyrosine phosphorylation exhibited by the pGEX PTK fusion protein (pGEX/JAK/2) (FIG. 4b) is ususually simple for an ectopically expressed PTK fusion protein. Remarkably, the auto-phosphorylation of the fusion protein itself does not seem to occur, an observation which may go some way toward explaining why we have had difficulty in demonstrating PTK activity in the intact protein.

cDNA clones covering the coding region of the PCR clone FD17 (JAK2) have been isolated from a range of murine cDNA libraries. The predicted amino acid sequences of JAK2 and JAK1 show several regions of significant similarity to each other (FIG. 5, see also Example 3).

Phylogenetic analysis

The phylogenetic relationship of the catalytic domains of must of the protein kinases has been determined using the tree-building programme of Feng and Doolittle (1987). FIG. 6 shows the phylogenetic relationship of the two kinase-related domains of the JAK1 protein to the rest of the kinase family. It is concluded from this family tree that these two domains had a common ancestor which pre-dated the development of the PTK sub-family. It is of interest to note that the kinase related domains of the ANP-receptor/guanylate cyclase family diverge at a point close by.

EXAMPLE 3

Cloning and sequencing of JAK2

Sequence of Murine JAK2

The PCR close FD17 was used as a basis to begin the cloning of longer cDNA clones of murine JAK2, cDNAs were isolated from a range of cDNA libraries, and by RACE (Frohman et al, 1989, Loh et al, 1989). The sequence of murine JAK2 is presented in FIG. 8. The predicted amino acid sequence indicates that this protein is highly related to JAK1. At the C-terminus, and extending approximately 270 amino acids towards the N-terminus (AA 715–980), are sequences bearing all the hall marks of a PTK catalytic domain. These are labelled in FIG. 8 according to the Hanks nomenclature. Immediately N-terminal to this (AA 400–600) lies the kinase-related domain characteristic of this class of PTKs (Wilks et al, 1991). The approach outlined in Example 2 in relation to JAK1 was followed and assigned these kinase related domains according to the Hanks nomenclature, appending the suffix Na to denote their origin. One unusual feature of this domain is an apparent insertion of seven amino acids between elements VIIa and VIIIa (Hanks nomenclature; Hanks and Quinn, 1991) with respect to other members of this family. This feature appeared in only one clone of the four sequenced which covered this region, and it remains possible that its presence is due to an infrequent splicing abberation, rather than being of functional significance.

Distribution of JAK2

Northern analysis of the expression of JAK2 in the mouse demonstrated tow mRNA transcripts (4.8 and 4.4 kb) hybridizing to the JAK2 probe under low and high stringency hybridization conditions (FIG. 9). It is intriguing to note that the levels of these transcripts alter with respect to one another in different tissues. For example, the kidney, spleen and lung appear to express predominantly the larger form, whereas ovary, placenta, skeletal (sk) muscle and all murine cell lines analyzed express both forms at about equal levels. Under low stringency hybridization conditions the murine JAK2 probe recognizes human JAK2 RNA (K562), however, only the smaller transcript of 4.4 kb could be detected. At this point, the origins of either of the two transcripts are unclear and no differential splicing events which could account for the differences between them could be detected. However, the major source of size differential in these transcripts may lie in the use of different polyadenylation signals. JAK2 is widely expressed in mouse organs, albeit to different levels. High expression was found in thymus, skeletal muscle, ovary and placenta, but JAK2 transcripts were barely detectable in testes or liver. In addition, JAK2 expression was detected in murine cell lines of fibroblastic (30F, NIH), epithelial (3ID) and hemopoietic (30.1) origin.

JAK Family Homology Domains

The cloning of JAK1 and JAK2 has facilitated the identification of JAK family homology domains. FIG. 10 shows a comparison of the amino acid sequences of JAK1. Sequence identity between these two proteins manifests itself as seven clearly defined homology domains. These seven domains are defined at a primary sequences level in FIG. 11. The PTK domain is classified as the JAK-homology Domain 1 (Hl), the second kinase related domain as the JH2 Domain, and so on to JH7. The boundaries of the JAK homology domains are arbitrary, and may or may not define functional domains. However, their delineation is a useful device to aid the consideration of the overall structural similarity of this class of proteins. The structure of the JH1 and JH2 Domains are described in Example 2. The JH3 is one of the least highly conserved of the JAK homology domains, each family member bearing between 35% (JAK2) to 50% (JAK1) of the deduced consensus sequence. The JH4 domain bears the sequence -GLYVLRWS- (SEQ. ID. No: 11) close to its C-terminal boundary, which has some degree of homology to the SH2 domain core sequence (see below). In addition, the most highly conserved sub-domain of this region bears a potential tyrosine phosphorylation site, namely, -VDGYFRI- (SEQ. ID. No: 12). Overall, the JH4 domain has between 51% (JAK2) and 64% (JAK1) of the deduced consensus sequence for this domain. Each of the remaining JAK, homology domains has been independently screened against the NKR1, and EMBL databases using the FASTA programme. There were no compelling homologies found with anything in these databases. It is concluded that these domains are structurally and functionally conserved in members of the JAK family of PTKs, but may not, in contradistinction to the SH2 and SH3 domains of the arc family of PTKs, have a role to play in other signal transduction molecules.

The apparent absence of an SH2 domain in any of the JAK family of PTKs is intriguing. Subtle sequence similarities have been detected between SH2 consensus sequences and portions of the JH3 and JH4 domains (H. Hanafusa and A. Bernards, personal communication). FIG. 12 shows an alignment of these two domains. Whilst the similarity of the JH3 domain to SH2 domains is most evident in the region surrounding the SH2 core sequence (FLVRES), the homology does not extend far in either direction beyond this region, and only reappears again close to the C-terminal boundary of the SH2 domain. This lack of extensive homology, particularly in many of those elements most highly conserved between SH2 domains (Koch et al., 1991) (presumably indicating those residues most intimately involved in the conserved function of this domain), suggests that the homology detected is either happenstance, or the product of considerable sequence divergence in evolution. The SH2 domain is currently believed to interact with phosphorylated tyrosine residues on the substrates of PTKs (reviewed in Pawson, 1989; Koch et al, 1991). Whether the JH3/JH4 domains play a similar functional role remaining to be determined.

EXAMPLE 4

To show that JAKs are represented in a range of animals, oligonucleotide probes were prepared and used to amplify and screen genomes from a variety of animals. JAK DNA was detected in Drosophila, Xenopus, mouse and human genomes. The main conserved sequence was DPG common to all animals tested.

REFERENCES

Claesson-Welsh, L., Eriksson, A., Westermark, B. and Heldin, C. H., *Proc Nat. Acad. Sci., USA* 86: 4917–4921, 1989.

Feng, D. F. and Doolittle, R. F. *Jour. Mol. Evolution* 25: 351–360, 1987.

Fitch, W. M. and Margoliash, E., *Science* 12: 279–284, 1967.

Hunter, T., and Sefton, B. M. *Proc. Nat. Acad. Sci.* 77: 1311–1315, 1980.

Kamps, M. P., and Sefton, B. M. *Oncogene* 2: 305–315, 1988.

Kozak, M. *Nucleic Acids Res.* 12: 857–872, 1984.

Kozma, S. C. Redmond, S. M. S., Xiano-Chan, F., Saurer, S. M. Groner, B., and Hynes, N. E. *EMBO J.* 7: 147–154, 1988.

Kyte, J. and Doolittle, R. F. *J. Mol. Biol,* 157: 105–132, 1982.

Laemmli, U. K. *Nature (London)* 227: 680–685, 1970.

Lee, M. G. and Nurse, P. *Nature (London)* 327: 31÷35, 1987.

Maniatis, T., Fritsch, E. T., and Sambrook, J., in *Molecular Cloning: A Laboratory Manual* Cold Spring Harbor, N.Y. 1982.

Moran, M. F., Koch, C. A., Sadowksi, I., and Pawson, T. *Oncogene* 3: 665–672, 1988.

Reichmann, E., Ball, R., Groner, B., and Friis, R. R. *J. Cell Bio,* 108: 1127–1138, 1989.

Smith, D. B. and Johnson, K. S. *Gene* 67: 31–40, 1988.

Suh, P., Ryu, S. H., Moon, K. H., Suh, H. W., and Rhee, S. G. *Cell* 54: 161–169, 1988.

Towbin, H., Stehelin, T., and Gordon, J., *Proc. Nat. Acad. Sci. USA* 76: 4350–4354, 1970.

Weinmaster, G., Zoller, M. M., Smith, M., Hinze, H., and Pawson, T. *Cell* 37: 559–568, 1984.

Wilks, A. F. and Kurban, R. H. *Oncogene* 3: 289–294, 1988.

Ziemiecki, A., Mueller, R. G., Xiao-Chan, F., Hynes, N. E. and Koznia, S., *EMBO J.,* 9: 191–196, 1990.

Dymecki, S. M., Neiderhuber, J. E., and Desiderio, S.v. *Science* 247: 332–336, 1990.

Firmback-Kraft, I., Byers, M., Showes, T., Dalla-Favera, R., and Krolewski, J. J., *Oncogene* 5: 1329–1336, 1990.

Frohman, M. A., Dush, J. M. and Martin, G., *Proc. Nat. Acad. Sci. USA* 85: 8998–9002, 1988.

Hanks, S. K. and Quinn, A. M. *Methods in Enzymology* 200: 38–62, 1991.

Hanks, S. K., Quinn, A. M. and Hunter, T. *Science* 241: 42–52, 1988.

Higgins, D. G. and Sharp, P. M. *Gene* 73: 237–244, 1988.

Holtzman, D. A., Cook, W. D. and Dunn, A. R. *Proc. Natl. Acad. Sci. USA* 84: 8325–8329, 1987.

Koch, C. A., Anderson, D., Moran, M. F., Ellis, C., and Pawson, T., 252: 668–674, 1991.

Loh, E. Y., Elliott, J. F., Cwirla, S., Lanier, T. D. and Davis, M. M. *Science* 243: 217–220, 1989.

Marth, J. D., Peet, R., Krebs, E. G., and Perimutter, R. M. *Cell* 43: 393–404, 1985.

Martinez, R., Mathey-Prevot, B., Bernards, A. and Baltimore, D. *Science* 237: 411–414, 1987.

Mayer, B. I., Hamaguchi, H., and Hanafusa, H., *Nature* 332: 272–274, 1988.

Nishizawa, M., Semba, K., Yoshida, M. C. Yamamoto, T., Sasaki, M., and Toyoshima, K. *Mol. Cell Biol.* 6: 511–517, 1986.

Pawson, T., *Oncogene* 3: 491–495, 1988.

Pearson, W. R. and Lippman, D. J. *Proc. Natl. Acad. Sci.* 85: 2444–2448, 1988.

Reid, H. H., Wilks, A. F., and Bernard, O., *Proc. Nat. Acad. Sci.* 87:14 1596–1600, 1990.

Sadowski, L., Stone, J. C., and Pawson, T. *Mol. Cell. Biol.* 6: 4396–4408, 1986.

Sanger, F., Nickleu, S., and Couson, A. R., *Proc. Nat. Acad. Sci. USA* 74: 5463–5467, 1977.

Semba, K., Nishizawa, M., Myajima, N., Yoshida, M. C., Sukagawa, J., Yamanishi, Y., Sasaki, M., Yamamoto, T., and Toyoshima, K., *Proc. Natl. Acad. Sci.* 83: 5459–5463, 1986.

Sukagawa, J., Semba, K., Yamanashi, Y., Nishizawa, M., Myajima, N., Kamamoto, T., and Toyoshima, K., *Mol. Cell. Biol.* 7: 41–47, 1987.

Trahey, M., Wong, G., Halenbeck, R., Rubinfeld, B., Martin, G. A., Ladner, M., Long, C. M., Crosier, W. J., Watt, K., Koths, K., and McCormick, F., *Science* 243: 1697–1700, 1988.

Wilks., A. F., *Process in Growth Factor Research* 2: 97–111, 1990.

Wilks, A. F., Harpur, A., Kurban, R. R., Ralph, S. J., Zuercher, G., and Ziemiecki, A. *Molecular and Cellular Biology* 11: 2057–2065, 1991.

Yamasmishi, Y., Pukishige, S. I., Semba, K., Sukegawa, J., Miyayjima, N., Matsubara, K. I., Yamamoto, T., and toyoshima, K., *Molec. Cell. Biol.* 7: 237–243, 1987.

I claim:

1. A purified isolated nucleic acid molecule which codes for a human protein tyrosine kinase like molecule which has multiple protein kinase catalytic domains, but no SH2 domains, the complementary sequence of which hybridizes to the nucleotide sequence set forth in SEQ ID NO: 1 at a temperature of 65° C. 6XSSC, 1% SDS, with a final wash of 0.2xSSC, 0.1% SDS, at 65° C.

2. The isolated nucleic acid molecule, consisting of the nucleotide sequence set forth in SEQ ID No: 1.

3. The isolated nucleic acid molecule of claim 1, wherein said polypeptide comprises two kinase catalytic domains.

4. The isolated nucleic acid molecule of claim 1, wherein said human protein tyrosine kinase like molecule has a molecular weight of form about 100,000 to about 200,000 daltons.

5. The isolated nucleic acid molecule of claim 4, wherein said protein tyrosine kinase like molecule has a molecular weight of from about 120,000 to about 150,000 daltons.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 4234 base pairs
        ( B ) TYPE: nucleic acid
        ( C ) STRANDEDNESS: single
        ( D ) TOPOLOGY: linear ( i i ) MOLECULE TYPE: nucleic acid ( x i ) SEQUENCE DESCRIPTION: SEQ ID NO: 1:

```
TGGCCGCCTA  GCGAGCTGCC  GGTCGACCCC  AGCCAGCCGA  GCGACGGGCG  CTGCCTGGCC        60
```

```
CAGGGCACAC GGAAGTGCGC TTCTCTGAAG TAGCTTTGGA AAGTAGAGAA GAAAATCCAG        120

TTTGCTTCTT GGAGAACACT GGACAGCTGA ATAA ATG CAG TAT CTA AAT               169
                                      Met Gln Tyr Leu Asn
                                                      -10

ATA AAA GAG GAC TGC AAT GCC ATG GCT TTC TGT GCT AAA ATG AGG             214
Ile Lys Glu Asp Cys Asn Ala Met Ala Phe Cys Ala Lys Met Arg
         -5              +1                  5

AGC TCC AAG AAG ACT GAG GTG AAC CTG GAG GCC CCT GAG CCA GGG             259
Ser Ser Lys Lys Thr Glu Val Asn Leu Glu Ala Pro Glu Pro Gly
         10              15                  20

GTG GAA GTG ATC TTC TAT CTG TCG GAC AGG GAG CCC CTC CGG CTG             304
Val Glu Val Ile Phe Tyr Leu Ser Asp Arg Glu Pro Leu Arg Leu
         25              30                  35

GGC AGT GGA GAG TAC ACA GCA GAG GAA CTG TGC ATC AGG GCT GCA             349
Gly Ser Gly Glu Tyr Thr Ala Glu Glu Leu Cys Ile Arg Ala Ala
         40              45                  50

CAG GCA TGC CGT ATC TCT CCT CTT TGT CAC AAC CTC TTT GCC CTG             394
Gln Ala Cys Arg Ile Ser Pro Leu Cys His Asn Leu Phe Ala Leu
         55              60                  65

TAT GAC GAG AAC ACC AAG CTC TGG TAT GCT CCA AAT CGC ACC ATC             439
Tyr Asp Glu Asn Thr Lys Leu Trp Tyr Ala Pro Asn Arg Thr Ile
         70              75                  80

ACC GTT GAT GAC AAG ATG TCC CTC CGG CTC CAC TAC CGG ATG AGG             484
Thr Val Asp Asp Lys Met Ser Leu Arg Leu His Tyr Arg Met Arg
         85              90                  95

TTC TAT TTC ACC AAT TGG CAT GGA ACC AAC GAC AAT GAG CAG TCA             529
Phe Tyr Phe Thr Asn Trp His Gly Thr Asn Asp Asn Glu Gln Ser
        100             105                 110

GTG TGG CGT CAT TCT CCA AAG AAG CAG AAA AAT GGC TAC GAG AAA             574
Val Trp Arg His Ser Pro Lys Lys Gln Lys Asn Gly Tyr Glu Lys
        115             120                 125

AAA AAG ATT CCA GAT GCA ACC CCT CTC CTT GAT GCC AGC TCA CTG             619
Lys Lys Ile Pro Asp Ala Thr Pro Leu Leu Asp Ala Ser Ser Leu
        130             135                 140

GAG TAT CTG TTT GCT CAG GGA CAG TAT GAT TTG GTG AAA TGC CTG             664
Glu Tyr Leu Phe Ala Gln Gly Gln Tyr Asp Leu Val Lys Cys Leu
        145             150                 155

GCT CCT ATT CGA GAC CCC AAG ACC GAG CAG GAT GGA CAT GAT ATT             709
Ala Pro Ile Arg Asp Pro Lys Thr Glu Gln Asp Gly His Asp Ile
        160             165                 170

GAG AAC GAG TGT CTA GGG ATG GCT GTC CTG GCC ATC TCA CAC TAT             754
Glu Asn Glu Cys Leu Gly Met Ala Val Leu Ala Ile Ser His Tyr
        175             180                 185

GCC ATG ATG AAG AAG ATG CAG TTG CCA GAA CTG CCC AAG GAC ATC             799
Ala Met Met Lys Lys Met Gln Leu Pro Glu Leu Pro Lys Asp Ile
        190             195                 200

AGC TAC AAG CGA TAT ATT CCA GAA ACA TTG AAT AAG TCC ATC AGA             844
Ser Tyr Lys Arg Tyr Ile Pro Glu Thr Leu Asn Lys Ser Ile Arg
        205             210                 215

CAG AGG AAC CTT CTC ACC AGG ATG CGG ATA AAT AAT GTT TTC AAG             889
Gln Arg Asn Leu Leu Thr Arg Met Arg Ile Asn Asn Val Phe Lys
        220             225                 230

GAT TTC CTA AAG GAA TTT AAC AAC AAG ACC ATT TGT GAC AGC AGC             934
Asp Phe Leu Lys Glu Phe Asn Asn Lys Thr Ile Cys Asp Ser Ser
        235             240                 245

GTG TCC ACG CAT GAC CTG AAG GTG AAA TAC TTG GCT ACC TTG GAA             979
Val Ser Thr His Asp Leu Lys Val Lys Tyr Leu Ala Thr Leu Glu
        250             255                 260

ACT TTG ACA AAA CAT TAC GGT GCT GAA ATA TTT GAG ACT TCC ATG            1024
```

-continued

```
          Thr  Leu  Thr  Lys  His  Tyr  Gly  Ala  Glu  Ile  Phe  Glu  Thr  Ser  Met
               265                 270                 275

TTA  CTG  ATT  TCA  TCA  GAA  AAT  GAG  ATG  AAT  TGG  TTT  CAT  TCG  AAT              1069
Leu  Leu  Ile  Ser  Ser  Glu  Asn  Glu  Met  Asn  Trp  Phe  His  Ser  Asn
     280                 285                 290

GAC  GGT  GGA  AAC  GTT  CTC  TAC  TAC  GAA  GTG  ATG  GTG  ACT  GGG  AAT              1114
Asp  Gly  Gly  Asn  Val  Leu  Tyr  Tyr  Glu  Val  Met  Val  Thr  Gly  Asn
     295                 300                 305

CTT  GGA  ATC  CAG  TGG  AGG  CAT  AAA  CCA  AAT  GTT  GTT  TCT  GTT  GAA              1159
Leu  Gly  Ile  Gln  Trp  Arg  His  Lys  Pro  Asn  Val  Val  Ser  Val  Glu
     310                 315                 320

AAG  GAA  AAA  AAT  AAA  CTG  AAG  CGG  AAA  AAA  CTG  GAA  AAT  AAA  GAC              1204
Lys  Glu  Lys  Asn  Lys  Leu  Lys  Arg  Lys  Lys  Leu  Glu  Asn  Lys  Asp
     325                 330                 335

AAG  AAG  GAT  GAG  GAG  AAA  AAC  AAG  ATC  CGG  GAA  GAG  TGG  AAC  AAT              1249
Lys  Lys  Asp  Glu  Glu  Lys  Asn  Lys  Ile  Arg  Glu  Glu  Trp  Asn  Asn
     340                 345                 350

TTT  TCA  TTC  TTC  CCT  GAA  ATC  ACT  CAC  ATT  GTA  ATA  AAG  GAG  TCT              1294
Phe  Ser  Phe  Phe  Pro  Glu  Ile  Thr  His  Ile  Val  Ile  Lys  Glu  Ser
     355                 360                 365

GTG  GTC  AGC  ATT  AAC  AAG  CAG  GAC  AAC  AAG  AAA  ATG  GAA  CTG  AAG              1339
Val  Val  Ser  Ile  Asn  Lys  Gln  Asp  Asn  Lys  Lys  Met  Glu  Leu  Lys
     370                 375                 380

CTC  TCT  TCC  CAC  GAG  GAG  GCC  TTG  TCC  TTT  GTG  TCC  CTG  GTA  GAT              1384
Leu  Ser  Ser  His  Glu  Glu  Ala  Leu  Ser  Phe  Val  Ser  Leu  Val  Asp
     385                 390                 395

GGC  TAC  TTC  CGG  CTC  ACA  GCA  GAT  GCC  CAT  CAT  TAC  CTC  TGC  ACC              1429
Gly  Tyr  Phe  Arg  Leu  Thr  Ala  Asp  Ala  His  His  Tyr  Leu  Cys  Thr
     400                 405                 410

GAC  GTG  GCC  CCC  CCG  TTG  ATC  GTC  CAC  AAC  ATA  CAG  AAT  GGC  TGT              1474
Asp  Val  Ala  Pro  Pro  Leu  Ile  Val  His  Asn  Ile  Gln  Asn  Gly  Cys
     415                 420                 425

CAT  GGT  CCA  ATC  TGT  ACA  GAA  TAC  GCC  ATC  AAT  AAA  TTG  CGG  CAA              1519
His  Gly  Pro  Ile  Cys  Thr  Glu  Tyr  Ala  Ile  Asn  Lys  Leu  Arg  Gln
     430                 435                 440

GAA  GGA  AGC  GAG  GAG  GGG  ATG  TAC  GTG  CTG  AGG  TGG  AGC  TGC  ACC              1564
Glu  Gly  Ser  Glu  Glu  Gly  Met  Tyr  Val  Leu  Arg  Trp  Ser  Cys  Thr
     445                 450                 455

GAC  TTT  GAC  AAC  ATC  CTC  ATG  ACC  GTC  ACC  TGC  TTT  GAG  AAG  TCT              1609
Asp  Phe  Asp  Asn  Ile  Leu  Met  Thr  Val  Thr  Cys  Phe  Glu  Lys  Ser
     460                 465                 470

GAG  CAG  GTG  CAG  GGT  GCC  CAG  AAG  CAG  TTC  AAG  AAC  TTT  CAG  ATC              1654
Glu  Gln  Val  Gln  Gly  Ala  Gln  Lys  Gln  Phe  Lys  Asn  Phe  Gln  Ile
     475                 480                 485

GAG  GTG  CAG  AAG  GGC  CGC  TAC  AGT  CTG  CAC  GGT  TCG  GAC  CGC  AGC              1699
Glu  Val  Gln  Lys  Gly  Arg  Tyr  Ser  Leu  His  Gly  Ser  Asp  Arg  Ser
     490                 495                 500

TTC  CCC  AGC  TTG  GGA  GAC  CTC  ATG  AGC  CAC  CTC  AAG  AAG  CAG  ATC              1744
Phe  Pro  Ser  Leu  Gly  Asp  Leu  Met  Ser  His  Leu  Lys  Lys  Gln  Ile
     505                 510                 515

CTG  CGC  ACG  GAT  AAC  ATC  AGC  TTC  ATG  CTA  AAA  CGC  TGC  TGC  CAG              1789
Leu  Arg  Thr  Asp  Asn  Ile  Ser  Phe  Met  Leu  Lys  Arg  Cys  Cys  Gln
     520                 525                 530

CCC  AAG  CCC  CGA  GAA  ATC  TCC  AAC  CTG  CTG  GTG  GCT  ACT  AAG  AAA              1834
Pro  Lys  Pro  Arg  Glu  Ile  Ser  Asn  Leu  Leu  Val  Ala  Thr  Lys  Lys
     535                 540                 545

GCC  CAG  GAG  TGG  CAG  CCC  GTC  TAC  CCC  ATG  AGC  CAG  CTG  AGT  TTC              1879
Ala  Gln  Glu  Trp  Gln  Pro  Val  Tyr  Pro  Met  Ser  Gln  Leu  Ser  Phe
     550                 555                 560

GAT  CGG  ATC  CTC  AAG  AAG  GAT  CTG  GTG  CAG  GGC  GAG  CAC  CTT  GGG              1924
```

|  |  |
|---|---|
| Asp Arg Ile Leu Lys Lys Asp Leu Val Gln Gly Glu His Leu Gly<br>565                          570                                     575 |  |
| AGA GGC ACG AGA ACA CAC ATC TAT TCT GGG ACC CTG ATG GAT TAC<br>Arg Gly Thr Arg Thr His Ile Tyr Ser Gly Thr Leu Met Asp Tyr<br>580                        585                                  590 | 1969 |
| AAG GAT GAC GAA GGA ACT TCT GAA GAG AAG AAG ATA AAA GTG ATC<br>Lys Asp Asp Glu Gly Thr Ser Glu Glu Lys Lys Ile Lys Val Ile<br>595                        600                                  605 | 2014 |
| CTC AAA GTC TTA GAC CCC AGC CAC AGG GAT ATT TCC CTG GCC TTC<br>Leu Lys Val Leu Asp Pro Ser His Arg Asp Ile Ser Leu Ala Phe<br>605                        615                                  620 | 2059 |
| TTC GAG GCA GCC AGC ATG ATG AGA CAG GTC TCC CAC AAA CAC ATC<br>Phe Glu Ala Ala Ser Met Met Arg Gln Val Ser His Lys His Ile<br>625                        630                                  635 | 2104 |
| GTG TAC CTC TAT GGC GTC TGT GTC CGC GAC GTG GAG AAT ATC ATG<br>Val Tyr Leu Tyr Gly Val Cys Val Arg Asp Val Glu Asn Ile Met<br>640                        645                                  650 | 2149 |
| GTG GAA GAG TTT GTG GAA GGG GGT CCT CTG GAT CTC TTC ATG CAC<br>Val Glu Glu Phe Val Glu Gly Gly Pro Leu Asp Leu Phe Met His<br>655                        660                                  665 | 2194 |
| CGG AAA AGT GAT GTC CTT ACC ACA CCA TGG AAA TTC AAA GTT GCC<br>Arg Lys Ser Asp Val Leu Thr Thr Pro Trp Lys Phe Lys Val Ala<br>670                        675                                  680 | 2239 |
| AAA CAG CTG GCC AGT GCC CTG AGC TAC TTG GAG GAT AAA GAC CTG<br>Lys Gln Leu Ala Ser Ala Leu Ser Tyr Leu Glu Asp Lys Asp Leu<br>685                        690                                  695 | 2284 |
| GTC CAT GGA AAT GTG TGT ACT AAA AAC CTC CTC CTG GCC CGT GAG<br>Val His Gly Asn Val Cys Thr Lys Asn Leu Leu Leu Ala Arg Glu<br>700                        705                                  710 | 2329 |
| GGA ATC GAC AGT GAG TGT GGC CCA TTC ATC AAG CTC AGT GAC CCC<br>Gly Ile Asp Ser Glu Cys Gly Pro Phe Ile Lys Leu Ser Asp Pro<br>715                        720                                  725 | 2374 |
| GGC ATC CCC ATT ACG GTG CTG TCT AGG CAA GAA TGC ATT GAA CGA<br>Gly Ile Pro Ile Thr Val Leu Ser Arg Gln Glu Cys Ile Glu Arg<br>730                        735                                  740 | 2419 |
| ATC CCA TGG ATT GCT CCT GAG TGT GTT GAG GAC TCC AAG AAC CTG<br>Ile Pro Trp Ile Ala Pro Glu Cys Val Glu Asp Ser Lys Asn Leu<br>745                        750                                  755 | 2464 |
| AGT GTG GCT GCT GAC AAG TGG AGC TTT GGA ACC ACG CTC TGG GAA<br>Ser Val Ala Ala Asp Lys Trp Ser Phe Gly Thr Thr Leu Trp Glu<br>760                        765                                  770 | 2509 |
| ATC TGC TAC AAT GGC GAG ATC CCC TTG AAA GAC AAG ACG CTG ATT<br>Ile Cys Tyr Asn Gly Glu Ile Pro Leu Lys Asp Lys Thr Leu Ile<br>775                        780                                  785 | 2554 |
| GAG AAA GAG AGA TTC TAT GAA AGC CGG TGC AGG CCA GTG ACA CCA<br>Glu Lys Glu Arg Phe Tyr Glu Ser Arg Cys Arg Pro Val Thr Pro<br>790                        795                                  800 | 2599 |
| TCA TGT AAG GAG CTG GCT GAC CTC ATG ACC CGC TGC ATG AAC TAT<br>Ser Cys Lys Glu Leu Ala Asp Leu Met Thr Arg Cys Met Asn Tyr<br>805                        810                                  815 | 2644 |
| GAC CCC AAT CAG AGG CCT TTC TTC CGA GCC ATC ATG AGA GAC ATT<br>Asp Pro Asn Gln Arg Pro Phe Phe Arg Ala Ile Met Arg Asp Ile<br>820                        825                                  830 | 2689 |
| AAT AAG CTT GAA GAG CAG AAT CCA GAT ATT GTT TCC AGA AAA AAA<br>Asn Lys Leu Glu Glu Gln Asn Pro Asp Ile Val Ser Arg Lys Lys<br>835                        840                                  845 | 2734 |
| AAC CAG CCA ACT GAA GTG GAC CCC ACA CAT TTT GAG AAG CGC TTC<br>Asn Gln Pro Thr Glu Val Asp Pro Thr His Phe Glu Lys Arg Phe<br>850                        855                                  860 | 2779 |
| CTA AAG AGG ATC CGT GAC TTG GGA GAG GGC CAC TTT GGG AAG GTT | 2824 |

```
          Leu  Lys  Arg  Ile  Arg  Asp  Leu  Gly  Glu  Gly  His  Phe  Gly  Lys  Val
          865                      870                      875

GAG  CTC  TGC  AGG  TAT  GAC  CCC  GAA  GAC  AAT  ACA  GGG  GAG  CAG  GTG           2869
Glu  Leu  Cys  Arg  Tyr  Asp  Pro  Glu  Asp  Asn  Thr  Gly  Glu  Gln  Val
880                      885                      890

GCT  GTT  AAA  TCT  CTG  AAG  CCT  GAG  AGT  GGA  GGT  AAC  CAC  ATA  GCT           2914
Ala  Val  Lys  Ser  Leu  Lys  Pro  Glu  Ser  Gly  Gly  Asn  His  Ile  Ala
895                      900                      905

GAT  CTG  AAA  AAG  GAA  ATC  GAG  ATC  TTA  AGG  AAC  CTC  TAT  CAT  GAG           2959
Asp  Leu  Lys  Lys  Glu  Ile  Glu  Ile  Leu  Arg  Asn  Leu  Tyr  His  Glu
910                      915                      920

AAC  ATT  GTG  AAG  TAC  AAA  GGA  ATC  TGC  ACA  GAA  GAC  GGA  GGA  AAT           3004
Asn  Ile  Val  Lys  Tyr  Lys  Gly  Ile  Cys  Thr  Glu  Asp  Gly  Gly  Asn
925                      930                      935

GGT  ATT  AAG  CTC  ATC  ATG  GAA  TTT  CTG  CCT  TCG  GGA  AGC  CTT  AAG           3049
Gly  Ile  Lys  Leu  Ile  Met  Glu  Phe  Leu  Pro  Ser  Gly  Ser  Leu  Lys
940                      945                      950

GAA  TAT  CTT  CCA  AAG  AAT  AAG  AAC  AAA  ATA  AAC  CTC  AAA  CAG  CAG           3094
Glu  Tyr  Leu  Pro  Lys  Asn  Lys  Asn  Lys  Ile  Asn  Leu  Lys  Gln  Gln
955                      960                      965

CTA  AAA  TAT  GCC  GTT  CAG  ATT  TGT  AAG  GGG  ATG  GAC  TAT  TTG  GGT           3139
Leu  Lys  Tyr  Ala  Val  Gln  Ile  Cys  Lys  Gly  Met  Asp  Tyr  Leu  Gly
970                      975                      980

TCT  CGG  CAA  TAC  GTT  CAC  CGG  GAC  TTG  GCA  GCA  AGA  AAT  GTC  CTT           3184
Ser  Arg  Gln  Tyr  Val  His  Arg  Asp  Leu  Ala  Ala  Arg  Asn  Val  Leu
985                      990                      995

GTT  GAG  AGT  GAA  CAC  CAA  GTG  AAA  ATT  GGA  GAC  TTC  GGT  TTA  ACC           3229
Val  Glu  Ser  Glu  His  Gln  Val  Lys  Ile  Gly  Asp  Phe  Gly  Leu  Thr
1000                     1005                     1010

AAA  GCA  ATT  GAA  ACC  GAT  AAG  GAG  TAT  TAC  ACC  GTC  AAG  GAT  GAC           3274
Lys  Ala  Ile  Glu  Thr  Asp  Lys  Glu  Tyr  Tyr  Thr  Val  Lys  Asp  Asp
1015                     1020                     1025

CGG  GAC  AGC  CCT  GTG  TTT  TGG  TAT  GCT  CCA  GAA  TGT  TTA  ATG  CAA           3319
Arg  Asp  Ser  Pro  Val  Phe  Trp  Tyr  Ala  Pro  Glu  Cys  Leu  Met  Gln
1030                     1035                     1040

TCT  AAA  TTT  TAT  ATT  GCC  TCT  GAC  GTC  TGG  TCT  TTT  GGA  GTC  ACT           3364
Ser  Lys  Phe  Tyr  Ile  Ala  Ser  Asp  Val  Trp  Ser  Phe  Gly  Val  Thr
1045                     1050                     1055

CTG  CAT  GAG  CTG  CTG  ACT  TAC  TGT  GAT  TCA  GAT  TCT  AGT  CCC  ATG           3409
Leu  His  Glu  Leu  Leu  Thr  Tyr  Cys  Asp  Ser  Asp  Ser  Ser  Pro  Met
1060                     1065                     1070

GCT  TTG  TTC  CTG  AAA  ATG  ATA  GGC  CCA  ACC  CAT  GGC  CAG  ATG  ACA           3454
Ala  Leu  Phe  Leu  Lys  Met  Ile  Gly  Pro  Thr  His  Gly  Gln  Met  Thr
1075                     1080                     1085

GTC  ACA  AGA  CTT  GTG  AAT  ACG  TTA  AAA  GAA  GGA  AAA  CGC  CTG  CCG           3499
Val  Thr  Arg  Leu  Val  Asn  Thr  Leu  Lys  Glu  Gly  Lys  Arg  Leu  Pro
1090                     1095                     1100

TGC  CCA  CCT  AAC  TGT  CCA  GAT  GAG  GTT  TAT  CAG  CTT  ATG  AGA  AAA           3544
Cys  Pro  Pro  Asn  Cys  Pro  Asp  Glu  Val  Tyr  Gln  Leu  Met  Arg  Lys
1105                     1110                     1115

TGC  TGG  GAA  TTC  CAA  CCA  TCC  AAT  CGG  ACA  AGC  TTT  CAG  AAC  CTT           3589
Cys  Trp  Glu  Phe  Gln  Pro  Ser  Asn  Arg  Thr  Ser  Phe  Gln  Asn  Leu
1120                     1135                     1130

ATT  GAA  GGA  TTT  GAA  GCA  CTT  TTA  AAA  TAAGAAGCAT  GAATAACATT               3636
Ile  Glu  Gly  Phe  Glu  Ala  Leu  Leu  Lys
1135                     1140

TAAATTCCAC  AGATTATCAA  GTCCTTCTCC  TGCAACAAAT  GCCCAAGTCA  TTTTTAAAA            3696

ATTTCTAATG  AAAGAAGTTT  GTGTTCTGTC  CAAAAAGTCA  CTGAACTCAT  ACTTCAGTAC           3756

ATATACATGT  ATAAGGCACA  CTGTAGTGCT  TAATATGTGT  AAGGACTTCC  TCTTTAAATT           3816
```

```
TGCACCAGTA ACTTAGTGAC ACATAATGAC AACCAAAATA TTTGAAAGCA CTTAAGCACT    3876

CCTCCTTGTG GAAAGAATAT ACCACCATTT CATCTGGCTA GTTCACCATC ACAACTGCAT    3936

TACCAAAAGG GGATTTTTGA AAACGAGGAG TTGACCAAAA TAATATCTGA AGATGATTGC    3996

TTTTCCCTGC TGCCAGCTGA CTGAAATGTT TTCCTGGCAC ATTAATCATA GATAAAGAAG    4056

ATTGATGGAC TTAGCCCTCA AACAGTATCT ATACAGTACT AGACCATGCA TTCTTAAAAT    4116

ATTAGATACC AGGTAGTATA TATTGTTTCT GTACAAAAAT GACTGTATTC TCTCACCAGT    4176

AGGACTTAAA CTTTGTTTCT CCAGTGGCTT AGCTCCTGTT CCTTTGGGTG ATCACTAG     4234
```

( 2 ) INFORMATION FOR SEQ ID NO:2:

( i ) SEQUENCE CHARACTERISTICS:
        ( A ) LENGTH: 3495 base pairs
        ( B ) TYPE: nucleic acid
        ( D ) STRANDEDNESS: single
        ( D ) TOPOLOGY: linear ( i i ) MOLECULE TYPE: nucleic acid ( x i ) SEQUENCE DESCRIPTION: SEQ ID NO: 2:

```
CTG CTT GAT GAC TTT GTC ATG TCT TAC CTT TCC CCT CAG TGG CGG          45
Leu Leu Asp Asp Phe Val Met Ser Tyr Leu Ser Pro Gln Trp Arg
 1               5                  10                  15

CAT GAT TTT GTT CAC GGA TGG ATA AAA GTA CCT GTG ACT CAT GAA          90
His Asp Phe Val His Gly Trp Ile Lys Val Pro Val Thr His Glu
             20                  25                  30

ACT CAG GAA GAG TGT CTT GGG ATG GCG GTG TTA GAC ATG ATG AGA         135
Thr Gln Glu Glu Cys Leu Gly Met Ala Val Leu Asp Met Met Arg
                 35                  40                  45

ATA GCT AAG GAG AAA GAC CAG ACT CCA CTG GCT GTC TAT AAC TCT         180
Ile Ala Lys Glu Lys Asp Gln Thr Pro Leu Ala Val Tyr Asn Ser
                     50                  55                  60

GTC AGC TAC AAG ACA TTC TTA CCA AAG TGC GTT CGA GCG AAG ATC         225
Val Ser Tyr Lys Thr Phe Leu Pro Lys Cys Val Arg Ala Lys Ile
                         65                  70                  75

CAA GAC TAT CAC ATT TTA ACC CGG AAG CGA ATC AGG TAC AGA TTT         270
Gln Asp Tyr His Ile Leu Thr Arg Lys Arg Ile Arg Tyr Arg Phe
                             80                  85                  90

CGC AGA TTC ATT CAG CAA TTC AGT CAA TGT AAA GCC ACT GCC AGG         315
Arg Arg Phe Ile Gln Gln Phe Ser Gln Cys Lys Ala Thr Ala Arg
                                 95                 100                 105

AAC CTA AAA CTT AAG TAT CTT ATA AAC CTG GAA ACC CTG CAG TCT         360
Asn Leu Lys Leu Lys Tyr Leu Ile Asn Leu Glu Thr Leu Gln Ser
                                    110                 115                 120

GCC TTC TAC ACA GAA CAG TTT GAA GTA AAA GAA TCT GCA AGA GGT         405
Ala Phe Tyr Thr Glu Gln Phe Glu Val Lys Glu Ser Ala Arg Gly
                                        125                 130                 135

CCT TCA GGT GAG GAG ATT TTT GCA ACC ATT ATA ATA ACT GGA AAC         450
Pro Ser Gly Glu Glu Ile Phe Ala Thr Ile Ile Ile Thr Gly Asn
                                            140                 145                 150

GGT GGA ATT CAG TGG TCA AGA GGG AAA CAT AAG GAA AGT GAG ACA         495
Gly Gly Ile Gln Trp Ser Arg Gly Lys His Lys Glu Ser Glu Thr
                                                155                 160                 165

CTG ACA GAA CAG GAC GTA CAG TTA TAT TGT GAT TTC CCT GAT ATT         540
Leu Thr Glu Gln Asp Val Gln Leu Tyr Cys Asp Phe Pro Asp Ile
                                                    170                 175                 180

ATT GAT GTC AGT ATT AAG CAA GCA AAT CAG GAA TGC TCA ACT GAA         585
Ile Asp Val Ser Ile Lys Gln Ala Asn Gln Glu Cys Ser Thr Glu
                                                        185                 190                 195
```

```
AGT  AGA  GTT  GTG  ACC  GTC  CAC  AAG  CAG  GAC  GGG  AAG  GTC  TTG  GAA         630
Ser  Arg  Val  Val  Thr  Val  His  Lys  Gln  Asp  Gly  Lys  Val  Leu  Glu
                    200                 205                      210

ATA  GAA  CTT  AGC  TCA  TTA  AAA  GAA  GCC  TTG  TCA  TTC  GTG  TCA  TTA         675
Ile  Glu  Leu  Ser  Ser  Leu  Lys  Glu  Ala  Leu  Ser  Phe  Val  Ser  Leu
               215                 220                      225

ATT  GAC  GGG  TAT  TAC  AGA  CTA  ACT  GCG  GAT  GCA  CAC  CAT  TAC  CTC         720
Ile  Asp  Gly  Tyr  Tyr  Arg  Leu  Thr  Ala  Asp  Ala  His  His  Tyr  Leu
                    230                 235                      240

TGC  AAA  GAG  GTG  GCT  CCC  CCA  GCT  GTG  TTC  GAG  AAC  ATA  CAC  AGC         765
Cys  Lys  Glu  Val  Ala  Pro  Pro  Ala  Val  Phe  Glu  Asn  Ile  His  Ser
               245                 250                      255

AAC  TGC  CAC  GGC  CCA  ATT  TCA  ATG  GAT  TTT  GCC  ATC  AGC  AAA  CTA         810
Asn  Cys  His  Gly  Pro  Ile  Ser  Met  Asp  Phe  Ala  Ile  Ser  Lys  Leu
                    260                 265                      270

AAG  AAG  GCA  GGA  AAC  CAG  ACT  GGA  CTG  TAT  GTA  CTT  CGA  TGT  AGC         855
Lys  Lys  Ala  Gly  Asn  Gln  Thr  Gly  Leu  Tyr  Val  Leu  Arg  Cys  Ser
               275                 280                      285

CCT  AAG  GAC  TTC  AAC  AAA  TAC  TTC  CTG  ACC  TTT  GCC  GTT  GAG  CGA         900
Pro  Lys  Asp  Phe  Asn  Lys  Tyr  Phe  Leu  Thr  Phe  Ala  Val  Glu  Arg
                    290                 295                      300

GAA  AAT  GTT  ATT  GAA  TAT  AAA  CAC  TGT  TTG  ATT  ACA  AAG  AAT  GAG         945
Glu  Asn  Val  Ile  Glu  Tyr  Lys  His  Cys  Leu  Ile  Thr  Lys  Asn  Glu
               305                 310                      315

AAT  GGA  GAG  TAC  AAC  CTC  AGT  GGG  ACT  AAG  AGG  AAC  TTC  AGT  AGT         990
Asn  Gly  Glu  Tyr  Asn  Leu  Ser  Gly  Thr  Lys  Arg  Asn  Phe  Ser  Ser
                    320                 325                      330

CTT  AAG  GAC  CTT  TTG  AAT  TGC  TAC  CAG  ATG  GAA  ACT  GTG  CGC  TCA        1035
Leu  Lys  Asp  Leu  Leu  Asn  Cys  Tyr  Gln  Met  Glu  Thr  Val  Arg  Ser
               335                 340                      345

GAC  AGT  ATC  ATC  TTC  CAG  TTC  ACC  AAA  TGC  TGT  CCT  CCA  AAG  CCG        1080
Asp  Ser  Ile  Ile  Phe  Gln  Phe  Thr  Lys  Cys  Cys  Pro  Pro  Lys  Pro
                    350                 355                      360

AAA  GAT  AAA  TCA  AAC  CTT  CTT  GTC  TTC  AGA  ACA  AAT  GGT  GTT  TCT        1125
Lys  Asp  Lys  Ser  Asn  Leu  Leu  Val  Phe  Arg  Thr  Asn  Gly  Val  Ser
               365                 370                      375

GAT  GTT  CAG  CTC  TCA  CCA  ACA  TTA  CAG  AGG  CAT  AAT  AAT  GTG  AAT        1170
Asp  Val  Gln  Leu  Ser  Pro  Thr  Leu  Gln  Arg  His  Asn  Asn  Val  Asn
                    380                 385                      390

CAA  ATG  GTG  TTT  CAC  AAA  ATC  AGG  AAT  GAA  GAT  TTG  ATA  TTT  AAT        1215
Gln  Met  Val  Phe  His  Lys  Ile  Arg  Asn  Glu  Asp  Leu  Ile  Phe  Asn
               395                 400                      405

GAA  AGC  CTT  GGC  CAA  GGC  ACT  TTT  ACA  AAA  ATA  TTT  AAA  GGT  GTA        1260
Glu  Ser  Leu  Gly  Gln  Gly  Thr  Phe  Thr  Lys  Ile  Phe  Lys  Gly  Val
                    410                 415                      420

AGA  AGA  GAA  GTT  GGA  GAT  TAT  GGT  CAG  CTG  CAC  GAA  ACC  GAA  GTT        1305
Arg  Arg  Glu  Val  Gly  Asp  Tyr  Gly  Gln  Leu  His  Glu  Thr  Glu  Val
               425                 430                      435

CTT  TTG  AAA  GTC  CTA  GAT  AAA  GCA  CAT  AGA  AAC  TAT  TCA  GAG  TCT        1350
Leu  Leu  Lys  Val  Leu  Asp  Lys  Ala  His  Arg  Asn  Tyr  Ser  Glu  Ser
                    440                 445                      450

TTC  TTT  GAA  GCA  GCA  AGC  ATG  ATG  AGT  CAG  CTT  TCT  CAC  AAG  CAT        1395
Phe  Phe  Glu  Ala  Ala  Ser  Met  Met  Ser  Gln  Leu  Ser  His  Lys  His
               455                 460                      465

TTG  GTT  TTG  AAT  TAT  GGA  GTA  TGT  GTC  TGT  GGA  GAG  GAG  AAC  ATT        1440
Leu  Val  Leu  Asn  Tyr  Gly  Val  Cys  Val  Cys  Gly  Glu  Glu  Asn  Ile
                    470                 475                      480

TTG  GTT  CAA  GAG  TTT  GTA  AAA  TTT  GGA  TCA  CTG  GAT  ACA  TAC  CTG        1485
Leu  Val  Gln  Glu  Phe  Val  Lys  Phe  Gly  Ser  Leu  Asp  Thr  Tyr  Leu
               485                 490                      495
```

|       |       |       |       |       |       |       |       |       |       |       |       |       |       |       |      |
|-------|-------|-------|-------|-------|-------|-------|-------|-------|-------|-------|-------|-------|-------|-------|------|
| AAG   | AAG   | AAC   | AAA   | AAT   | TCT   | ATA   | AAT   | ATA   | TTA   | TGG   | AAA   | CTT   | GGA   | GTG   | 1530 |
| Lys   | Lys   | Asn   | Lys   | Asn   | Ser   | Ile   | Asn   | Ile   | Leu   | Trp   | Lys   | Leu   | Gly   | Val   |      |
|       |       |       |       | 500   |       |       |       | 505   |       |       |       |       |       | 510   |      |
| GCG   | AAG   | CAG   | TTG   | GCA   | TGG   | GCC   | ATG   | CAC   | TTC   | CTC   | GAA   | GAA   | AAA   | TCC   | 1575 |
| Ala   | Lys   | Gln   | Leu   | Ala   | Trp   | Ala   | Met   | His   | Phe   | Leu   | Glu   | Glu   | Lys   | Ser   |      |
|       |       |       |       | 515   |       |       |       | 520   |       |       |       |       |       | 525   |      |
| CTT   | ATT   | CAT   | GGG   | AAT   | GTG   | TGT   | GCT   | AAA   | AAT   | ATC   | CTG   | CTT   | ATC   | AGA   | 1620 |
| Leu   | Ile   | His   | Gly   | Asn   | Val   | Cys   | Ala   | Lys   | Asn   | Ile   | Leu   | Leu   | Ile   | Arg   |      |
|       |       |       |       | 530   |       |       |       | 535   |       |       |       |       |       | 540   |      |
| GAA   | GAA   | GAC   | AGG   | AGA   | ACG   | GGG   | AAC   | CCA   | CCT   | TTC   | ATC   | AAA   | CTT   | AGT   | 1665 |
| Glu   | Glu   | Asp   | Arg   | Arg   | Thr   | Gly   | Asn   | Pro   | Pro   | Phe   | Ile   | Lys   | Leu   | Ser   |      |
|       |       |       |       | 545   |       |       |       | 550   |       |       |       |       |       | 555   |      |
| GAT   | CCT   | GGC   | ATT   | AGC   | ATT   | ACA   | GTT   | CTA   | CCG   | AAG   | GAC   | ATT   | TCT   | TCC   | 1710 |
| Asp   | Pro   | Gly   | Ile   | Ser   | Ile   | Thr   | Val   | Leu   | Pro   | Lys   | Asp   | Ile   | Ser   | Ser   |      |
|       |       |       |       | 560   |       |       |       | 565   |       |       |       |       |       | 570   |      |
| TGT   | TGT   | TTC   | CAA   | GTT   | CTT   | CAG   | GAG   | AGA   | ATA   | CCA   | TGG   | GTA   | CCA   | CCT   | 1755 |
| Cys   | Cys   | Phe   | Gln   | Val   | Leu   | Gln   | Glu   | Arg   | Ile   | Pro   | Trp   | Val   | Pro   | Pro   |      |
|       |       |       |       | 575   |       |       |       | 580   |       |       |       |       |       | 585   |      |
| GAG   | TGC   | ATT   | GAG   | AAT   | CCT   | AAA   | AAT   | CTA   | ACT   | CTG   | GCA   | ACA   | GAC   | AAG   | 1800 |
| Glu   | Cys   | Ile   | Glu   | Asn   | Pro   | Lys   | Asn   | Leu   | Thr   | Leu   | Ala   | Thr   | Asp   | Lys   |      |
|       |       |       |       | 590   |       |       |       | 595   |       |       |       |       |       | 600   |      |
| TGG   | AGC   | TTC   | GGG   | ACC   | ACT   | CTG   | TGG   | GAG   | ATC   | TGC   | AGT   | GGA   | GGA   | GAT   | 1845 |
| Trp   | Ser   | Phe   | Gly   | Thr   | Thr   | Leu   | Trp   | Glu   | Ile   | Cys   | Ser   | Gly   | Gly   | Asp   |      |
|       |       |       |       | 605   |       |       |       | 610   |       |       |       |       |       | 615   |      |
| AAG   | CCC   | CTG   | AGT   | GCT   | CTG   | GAT   | TCT   | CAA   | AGA   | AAG   | CTG   | CAG   | TTC   | TAT   | 1890 |
| Lys   | Pro   | Leu   | Ser   | Ala   | Leu   | Asp   | Ser   | Gln   | Arg   | Lys   | Leu   | Gln   | Phe   | Tyr   |      |
|       |       |       |       | 620   |       |       |       | 625   |       |       |       |       |       | 630   |      |
| GAA   | GAT   | AAG   | CAT   | CAG   | CTT   | CCT   | GCA   | CCC   | AAG   | TGG   | ACA   | GAG   | TTG   | GCA   | 1935 |
| Glu   | Asp   | Lys   | His   | Gln   | Leu   | Pro   | Ala   | Pro   | Lys   | Trp   | Thr   | Glu   | Leu   | Ala   |      |
|       |       |       |       | 635   |       |       |       | 640   |       |       |       |       |       | 645   |      |
| AAC   | CTT   | ATA   | AAT   | AAT   | TGC   | ATG   | GAC   | TAT   | GAG   | CCA   | GAT   | TTC   | AGG   | CCT   | 1980 |
| Asn   | Leu   | Ile   | Asn   | Asn   | Cys   | Met   | Asp   | Tyr   | Glu   | Pro   | Asp   | Phe   | Arg   | Pro   |      |
|       |       |       |       | 650   |       |       |       | 655   |       |       |       |       |       | 660   |      |
| GCT   | TTC   | AGA   | GCT   | GTC   | ATC   | CGT   | GAT   | CTT   | AAC   | AGC   | CTG   | TTT   | ACT   | CCA   | 2025 |
| Ala   | Phe   | Arg   | Ala   | Val   | Ile   | Arg   | Asp   | Leu   | Asn   | Ser   | Leu   | Phe   | Thr   | Pro   |      |
|       |       |       |       | 665   |       |       |       | 670   |       |       |       |       |       | 675   |      |
| GAT   | TAT   | GAA   | CTA   | CTA   | ACA   | GAA   | AAT   | GAC   | ATG   | CTA   | CCA   | AAC   | ATG   | AGA   | 2070 |
| Asp   | Tyr   | Glu   | Leu   | Leu   | Thr   | Glu   | Asn   | Asp   | Met   | Leu   | Pro   | Asn   | Met   | Arg   |      |
|       |       |       |       | 680   |       |       |       | 685   |       |       |       |       |       | 690   |      |
| ATA   | GGT   | GCC   | CTA   | GGG   | TTT   | TCT   | GGT   | GCT   | TTT   | GAA   | GAC   | AGG   | GAC   | CCT   | 2115 |
| Ile   | Gly   | Ala   | Leu   | Gly   | Phe   | Ser   | Gly   | Ala   | Phe   | Glu   | Asp   | Arg   | Asp   | Pro   |      |
|       |       |       |       | 695   |       |       |       | 700   |       |       |       |       |       | 705   |      |
| ACA   | CAG   | TTT   | GAA   | GAG   | AGA   | CAC   | TTG   | AAG   | TTT   | CTA   | CAG   | CAG   | CTT   | GGC   | 2160 |
| Thr   | Gln   | Phe   | Glu   | Glu   | Arg   | His   | Leu   | Lys   | Phe   | Leu   | Gln   | Gln   | Leu   | Gly   |      |
|       |       |       |       | 710   |       |       |       | 715   |       |       |       |       |       | 720   |      |
| AAA   | GGT   | AAC   | TTC   | GGG   | AGT   | GTG   | GAG   | ATG   | TGC   | CGC   | TAT   | GAC   | CCG   | CTG   | 2205 |
| Lys   | Gly   | Asn   | Phe   | Gly   | Ser   | Val   | Glu   | Met   | Cys   | Arg   | Tyr   | Asp   | Pro   | Leu   |      |
|       |       |       |       | 725   |       |       |       | 730   |       |       |       |       |       | 735   |      |
| CAG   | GAC   | AAC   | ACT   | GGC   | GAG   | GTG   | GTC   | GCT   | GTG   | AAG   | AAA   | CTC   | CAG   | CAC   | 2250 |
| Gln   | Asp   | Asn   | Thr   | Gly   | Glu   | Val   | Val   | Ala   | Val   | Lys   | Lys   | Leu   | Gln   | His   |      |
|       |       |       |       | 740   |       |       |       | 745   |       |       |       |       |       | 750   |      |
| AGC   | ACT   | GAA   | GAG   | CAC   | CTC   | CGA   | GAC   | TTT   | GAG   | AGG   | GAG   | ATC   | GAG   | ATC   | 2295 |
| Ser   | Thr   | Glu   | Glu   | His   | Leu   | Arg   | Asp   | Phe   | Glu   | Arg   | Glu   | Ile   | Glu   | Ile   |      |
|       |       |       |       | 755   |       |       |       | 760   |       |       |       |       |       | 765   |      |
| CTG   | AAA   | TCC   | TTG   | CAG   | CAT   | GAC   | AAC   | ATC   | GTC   | AAG   | TAC   | AAG   | GGA   | GTG   | 2340 |
| Leu   | Lys   | Ser   | Leu   | Gln   | His   | Asp   | Asn   | Ile   | Val   | Lys   | Tyr   | Lys   | Gly   | Val   |      |
|       |       |       |       | 770   |       |       |       | 775   |       |       |       |       |       | 780   |      |
| TGC   | TAC   | AGT   | GCG   | GGT   | CGG   | CGC   | AAC   | CTA   | AGA   | TTA   | ATT   | ATG   | GAA   | TAT   | 2385 |
| Cys   | Tyr   | Ser   | Ala   | Gly   | Arg   | Arg   | Asn   | Leu   | Arg   | Leu   | Ile   | Met   | Glu   | Tyr   |      |
|       |       |       |       | 785   |       |       |       | 790   |       |       |       |       |       | 795   |      |

```
TTA  CCA  TAT  GGA  AGT  TTA  CGA  GAC  TAT  CTC  CAA  AAA  CAT  AAA  GAA        2430
Leu  Pro  Tyr  Gly  Ser  Leu  Arg  Asp  Tyr  Leu  Gln  Lys  His  Lys  Glu
                    800                      805                      810

CGG  ATA  GAT  CAC  AAA  AAA  CTT  CTT  CAA  TAC  ACA  TCT  CAG  ATA  TGC        2475
Arg  Ile  Asp  His  Lys  Lys  Leu  Leu  Gln  Tyr  Thr  Ser  Gln  Ile  Cys
                    815                      820                      825

AAG  GGC  ATG  GAA  TAT  CTT  GGT  ACA  AAA  AGG  TAT  ATC  CAC  AGG  GAC        2520
Lys  Gly  Met  Glu  Tyr  Leu  Gly  Thr  Lys  Arg  Tyr  Ile  His  Arg  Asp
                    830                      835                      840

CTG  GCA  ACA  AGG  AAC  ATA  TTG  GTG  GAA  AAT  GAG  AAC  AGG  GTT  AAA        2565
Leu  Ala  Thr  Arg  Asn  Ile  Leu  Val  Glu  Asn  Glu  Asn  Arg  Val  Lys
                    845                      850                      855

ATA  GGA  GAC  TTC  GGA  TTA  ACC  AAA  GTC  TTG  CCG  CAG  GAC  AAA  GAA        2610
Ile  Gly  Asp  Phe  Gly  Leu  Thr  Lys  Val  Leu  Pro  Gln  Asp  Lys  Glu
                    860                      865                      870

TAC  TAC  AAA  GTA  AAG  GAG  CCA  GGG  GAA  AGC  CCC  ATA  TTC  TGG  TAC        2655
Tyr  Tyr  Lys  Val  Lys  Glu  Pro  Gly  Glu  Ser  Pro  Ile  Phe  Trp  Tyr
                    875                      880                      885

GCA  CCT  GAA  TCC  TTG  ACG  GAG  AGC  AAG  TTT  TCT  GTG  GCC  TCA  GAT        2700
Ala  Pro  Glu  Ser  Leu  Thr  Glu  Ser  Lys  Phe  Ser  Val  Ala  Ser  Asp
                    890                      895                      900

GTG  TGG  AGC  TTT  GGA  GTG  GTT  CTA  TAC  GAA  CTT  TTC  ACA  TAC  ATC        2745
Val  Trp  Ser  Phe  Gly  Val  Val  Leu  Tyr  Glu  Leu  Phe  Thr  Tyr  Ile
                    905                      910                      915

GAG  AAG  AGT  AAA  AGT  CCA  CCC  GTG  GAA  TTT  ATG  CGA  ATG  ATT  GGC        2790
Glu  Lys  Ser  Lys  Ser  Pro  Pro  Val  Glu  Phe  Met  Arg  Met  Ile  Gly
                    920                      925                      930

AAT  GAT  AAA  CAA  GGG  CAA  ATG  ATT  GTG  TTC  CAT  TTG  ATA  GAG  CTA        2835
Asn  Asp  Lys  Gln  Gly  Gln  Met  Ile  Val  Phe  His  Leu  Ile  Glu  Leu
                    935                      940                      945

CTG  AAG  AGC  AAC  GGA  AGA  TTG  CCA  AGG  CCA  GAA  GGA  TGC  CCA  GAT        2880
Leu  Lys  Ser  Asn  Gly  Arg  Leu  Pro  Arg  Pro  Glu  Gly  Cys  Pro  Asp
                    950                      955                      960

GAG  ATT  TAT  GTG  ATC  ATG  ACA  GAG  TGC  TGG  AAC  AAC  AAT  GTG  AGC        2925
Glu  Ile  Tyr  Val  Ile  Met  Thr  Glu  Cys  Trp  Asn  Asn  Asn  Val  Ser
                    965                      970                      975

CAG  CGT  CCC  TCC  TTC  AGG  GAC  CTT  TCC  TTC  GGG  TGG  ATC  AAA  TCC        2970
Gln  Arg  Pro  Ser  Phe  Arg  Asp  Leu  Ser  Phe  Gly  Trp  Ile  Lys  Ser
                    980                      985                      990

GGG  ACA  GTA  TAGCTGCGTG  AAAGAGATGG  CCTTACTCAG  AGACCAAGCA                    3019
Gly  Thr  Val

GACTTCCAGA  ACCAGAACAA  AGCTCTGTAG  CCTTGTGTCT  ACACATCCTT                       3069

ATCATGACGC  TAGCTAGGCA  GAAAGAAAAC  TGTGACGCCG  TCTGCTCAAA                       3119

AGCTTTGGAA  AACGCCGTGC  AGGTTTGTTT  CATCACCATC  TGTAAAAACC                       3169

ACTGCTCAAG  TCTGGCAGCA  TGCTTGTGGG  CTGATGCATG  GAGCTCACCA                       3219

CAGAGTCTCT  GCATCTCCTC  TGACAGAAGA  AGAAAAATAG  ACAATTTTCA                       3269

ACTCACTTTT  TTGAGAAATG  GAAAAAAATT  ATAATGTAAA  TTTTTCAGTG                       3319

TAGGAAATAC  ACAGAACATA  CATGTACAGT  TTTTACCACG  TGGAGTGTAT                       3369

AATACTTTGG  CCTCTTGTGT  GATTTACATG  AGGGCTGATG  TTTGTTAATG                       3419

TTTTCTAATT  TTTCCATAGG  TGATCTATAA  TAACTTCATG  ATACAAATTA                       3469

AAATGCTCAG  AAAATTAAAA  AAAAAA                                                   3495
```

( 2 ) INFORMATION FOR SEQ ID NO:3:

( i ) SEQUENCE CHARACTERISTICS:
        ( A ) LENGTH: 6 amino acid residues (B) TYPE: amino acid
(D) TOPOLOGY: linear (ix) FEATURE:
(D) OTHER INFORMATION: Xaa in positions 2, 4 and 5 is unknown.

(xi) SEQUENCE DESCRIPTION: SEQ ID NO: 3:

Gly Xaa Gly Xaa Xaa Gly
                  5

(2) INFORMATION FOR SEQ ID NO:4:

(i) SEQUENCE CHARACTERISTICS:
(A) LENGTH: 16 amino acid residues
(B) TYPE: amino acid
(D) TOPOLOGY: linear (xi) SEQUENCE DESCRIPTION: SEQ ID NO: 4:

Thr Ser Phe Gln Asn Leu Ile Glu Cys Phe Glu Ala Leu Leu Lys Cys
                  5                   10                  15

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 5:

TACACCTTTA AATATTTTTG T                                    21

(2) INFORMATION FOR SEQ ID NO:6:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 6:

CTCGAGTCGA CGAATTC                                         17

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 7:

CTTGCTTAAT ACTGACATCA                                      20

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 8:

CTTGCTTAAT ACTGACATCA                                      20

(2) INFORMATION FOR SEQ ID NO:9:

(i) SEQUENCE CHARACTERISTICS:
  (A) LENGTH: 9 base pairs
  (B) TYPE: nucleic acid
  (C) STRANDEDNESS: single
  (D) TOPOLOGY: linear (xi) SEQUENCE DESCRIPTION: SEQ ID NO: 9:

TAAATGCAG    9

(2) INFORMATION FOR SEQ ID NO:10:

(i) SEQUENCE CHARACTERISTICS:
    (A) LENGTH: 9 base pairs
    (B) TYPE: nucleic acid
    (C) STRANDEDNESS: single
    (D) TOPOLOGY: linear (xi) SEQUENCE DESCRIPTION: SEQ ID NO: 10:

GCCATGGCT    9

(2) INFORMATION FOR SEQ ID NO:11:

(i) SEQUENCE CHARACTERISTICS:
    (A) LENGTH: 8 amino acid residues
    (B) TYPE: amino acid
    (D) TOPOLOGY: linear (xi) SEQUENCE DESCRIPTION: SEQ ID NO: 11:

Gly Leu Tyr Val Leu Arg Trp Ser
                 8

(2) INFORMATION FOR SEQ ID NO:12:

(i) SEQUENCE CHARACTERISTICS:
    (A) LENGTH: 7 amino acid residues
    (B) TYPE: amino acid
    (D) TOPOLOGY: linear (xi) SEQUENCE DESCRIPTION: SEQ ID NO: 12:

Val Asp Gly Tyr Phe Arg Ile
             5

(2) INFORMATION FOR SEQ ID NO: 13:

(i) SEQUENCE CHARACTERISTICS:
    (A) LENGTH: 47 amino acids
    (B) TYPE: amino acid
    (D) TOPOLOGY: linear (xi) SEQUENCE DESCRIPTION: SEQ ID NO: 13:

Lys Ile Gly Glu Gly Thr Tyr Gly Val Val Tyr Lys Gly Arg His
                 5                  10                 15
Lys Thr Thr Gly Gln Val Val Ala Met Lys Lys Ile Arg Leu Glu
                 20                 25                 30
Ser Glu Glu Glu Gly Val Pro Ser Thr Ala Ile Arg Glu Ile Ser
                 35                 40                 45
Leu Leu (2) INFORMATION FOR SEQ ID NO: 14:

(i) SEQUENCE CHARACTERISTICS:
    (A) LENGTH: 82 amino acids
    (B) TYPE: amino acid
    (D) TOPOLOGY: linear (xi) SEQUENCE DESCRIPTION: SEQ ID NO: 14:

Val Phe Cys His Ser Arg Arg Val Leu His Arg Asp Leu Lys Pro
                 5                      10                     15

Gln Asn Leu Leu Ile Asp Asp Lys Gly Thr Ile Lys Leu Ala Asp
                 20                     25                     30

Phe Gly Leu Ala Arg Ala Phe Gly Ile Pro Ile Arg Val Tyr Thr
                 35                     40                     45

His Glu Val Val Thr Leu Trp Tyr Arg Ser Pro Glu Val Leu Leu
                 50                     55                     60

Gly Ser Ala Arg Tyr Ser Thr Pro Val Asp Ile Trp Ser Ile Gly
                 65                     70                     75

Thr Ile Phe Ala Glu Leu Ala
                 80

( 2 ) INFORMATION FOR SEQ ID NO: 15:

( i ) SEQUENCE CHARACTERISTICS:
        ( A ) LENGTH: 30 amino acids
        ( B ) TYPE: amino acid
        ( D ) TOPOLOGY: linear ( x i ) SEQUENCE DESCRIPTION: SEQ ID NO: 15:

Leu Ala Ser His His Val Lys Asn Leu Asp Glu Asn Gly Leu Asp
                 5                      10                     15

Leu Leu Ser Lys Met Leu Ile Tyr Asp Pro Ala Lys Arg Ile Ser
                 20                     25                     30

( 2 ) INFORMATION FOR SEQ ID NO: 16:

( i ) SEQUENCE CHARACTERISTICS:
        ( A ) LENGTH: 601 amino acids
        ( B ) TYPE: amino acid
        ( D ) TOPOLOGY: linear ( x i ) SEQUENCE DESCRIPTION: SEQ ID NO: 16:

Val Phe His Lys Ile Arg Asn Glu Asp Leu Ile Phe Asn Glu Ser
                 5                      10                     15

Leu Gly Gln Gly Thr Phe Thr Lys Ile Phe Lys Gly Val Arg Arg
                 20                     25                     30

Glu Val Gly Asp Tyr Gly Gln Leu His Glu Thr Glu Val Leu Leu
                 35                     40                     45

Lys Val Leu Asp Lys Ala His Arg Asn Tyr Ser Glu Ser Phe Phe
                 50                     55                     60

Glu Ala Ala Ser Met Met Ser Gln Leu Ser His Lys His Leu Val
                 65                     70                     75

Leu Asn Tyr Gly Val Cys Val Cys Gly Glu Glu Asn Ile Leu Val
                 80                     85                     90

Gln Glu Phe Val Lys Phe Gly Ser Leu Asp Thr Tyr Leu Lys Lys
                 95                     100                    105

Asn Lys Asn Ser Ile Asn Ile Leu Trp Lys Leu Gly Val Ala Lys
                 110                    115                    120

Gln Leu Ala Trp Ala Met His Phe Leu Glu Glu Lys Ser Leu Ile
                 125                    130                    135

His Gly Asn Val Cys Ala Lys Asn Ile Leu Leu Ile Arg Glu Glu
                 140                    145                    150

Asp Arg Arg Thr Gly Asn Pro Pro Phe Ile Lys Leu Ser Asp Pro
                 155                    160                    165

Gly Ile Ser Ile Thr Val Leu Pro Lys Asp Ile Ser Ser Cys Cys
                 170                    175                    180

```
Phe Gln Val Leu Gln Glu Arg Ile Pro Trp Val Pro Pro Glu Cys
            185                 190                 195

Ile Glu Asn Pro Lys Asn Leu Thr Leu Ala Thr Asp Lys Trp Ser
            200                 205                 210

Phe Gly Thr Thr Leu Trp Glu Ile Cys Ser Gly Gly Asp Lys Pro
            215                 220                 225

Leu Ser Ala Leu Asp Ser Gln Arg Lys Leu Gln Phe Tyr Glu Asp
            230                 235                 240

Lys His Gln Leu Pro Ala Pro Lys Trp Thr Glu Leu Ala Asn Leu
            245                 250                 255

Ile Asn Asn Cys Met Asp Tyr Glu Pro Asp Phe Arg Pro Ala Phe
            260                 265                 270

Arg Ala Val Ile Arg Asp Leu Asn Ser Leu Phe Thr Pro Asp Tyr
            275                 280                 285

Glu Leu Leu Thr Glu Asn Asp Met Leu Pro Asn Met Arg Ile Gly
            290                 295                 300

Ala Leu Gly Phe Ser Gly Ala Phe Glu Asp Arg Asp Pro Thr Gln
            305                 310                 315

Phe Glu Glu Arg His Leu Lys Phe Leu Gln Gln Leu Gly Lys Gly
            320                 325                 330

Asn Phe Gly Ser Val Glu Met Cys Arg Tyr Asp Pro Leu Gln Asp
            335                 340                 345

Asn Thr Gly Glu Val Val Ala Val Lys Lys Leu Gln His Ser Thr
            350                 355                 360

Glu Glu His Leu Arg Asp Phe Glu Arg Glu Ile Glu Ile Leu Lys
            365                 370                 375

Ser Leu Gln His Asp Asn Ile Val Lys Tyr Lys Gly Val Cys Tyr
            380                 385                 390

Ser Ala Gly Arg Arg Asn Leu Arg Leu Ile Met Glu Tyr Leu Pro
            395                 400                 405

Tyr Gly Ser Leu Arg Asp Tyr Leu Gln Lys His Lys Glu Arg Ile
            410                 415                 420

Asp His Lys Lys Leu Leu Gln Tyr Thr Ser Gln Ile Cys Lys Gly
            425                 430                 435

Met Glu Tyr Leu Gly Thr Lys Arg Tyr Ile His Arg Asp Leu Ala
            440                 445                 450

Thr Arg Asn Ile Leu Val Glu Asn Glu Asn Arg Val Lys Ile Gly
            455                 460                 465

Asp Phe Gly Leu Thr Lys Val Leu Pro Gln Asp Lys Glu Tyr Tyr
            470                 475                 480

Lys Val Lys Glu Pro Gly Glu Ser Pro Ile Phe Trp Tyr Ala Pro
            485                 490                 495

Glu Ser Leu Thr Glu Ser Lys Phe Ser Val Ala Ser Asp Val Trp
            500                 505                 510

Ser Phe Gly Val Val Leu Tyr Glu Leu Phe Thr Tyr Ile Glu Lys
            515                 520                 525

Ser Lys Ser Pro Pro Val Glu Phe Met Arg Met Ile Gly Asn Asp
            530                 535                 540

Lys Gln Gly Gln Met Ile Val Phe His Leu Ile Glu Leu Leu Lys
            545                 550                 555

Ser Asn Gly Arg Leu Pro Arg Pro Glu Gly Cys Pro Asp Glu Ile
            560                 565                 570

Tyr Val Ile Met Thr Glu Cys Trp Asn Asn Asn Val Ser Gln Arg
            575                 580                 585
```

Pro Ser Phe Arg Asp Leu Ser Phe Gly Trp Ile Lys Ser Gly Thr
            590                     595                     600

Val ( 2 ) INFORMATION FOR SEQ ID NO: 17:

( i ) SEQUENCE CHARACTERISTICS:
        ( A ) LENGTH: 581 amino acids
        ( B ) TYPE: amino acid
        ( D ) TOPOLOGY: linear ( x i ) SEQUENCE DESCRIPTION: SEQ ID NO: 17:

Ser Phe Asp Arg Ile Leu Lys Lys Asp Leu Val Gln Gly Glu His
              5                  10                      15

Leu Gly Arg Gly Thr Arg Thr His Ile Tyr Ser Gly Thr Leu Met
             20                  25                      30

Asp Tyr Lys Asp Asp Glu Gly Thr Ser Glu Glu Lys Lys Ile Lys
             35                  40                      45

Val Ile Leu Lys Val Leu Asp Pro Ser His Arg Asp Ile Ser Leu
             50                  55                      60

Ala Phe Phe Glu Ala Ala Ser Met Met Arg Gln Val Ser His Lys
             65                  70                      75

His Ile Val Tyr Leu Tyr Gly Val Cys Val Arg Asp Val Glu Asn
             80                  85                      90

Ile Met Val Glu Glu Phe Val Glu Gly Gly Pro Leu Asp Leu Phe
             95                  100                     105

Met His Arg Lys Ser Asp Val Leu Thr Thr Pro Trp Lys Phe Lys
             110                 115                     120

Val Ala Lys Gln Leu Ala Ser Ala Leu Ser Tyr Leu Glu Asp Lys
             125                 130                     135

Asp Leu Val His Gly Asn Val Cys Thr Lys Asn Leu Leu Leu Ala
             140                 145                     150

Arg Glu Gly Ile Asp Ser Glu Cys Gly Pro Phe Ile Lys Leu Ser
             155                 160                     165

Asp Pro Gly Ile Pro Ile Thr Val Leu Ser Arg Gln Glu Cys Ile
             170                 175                     180

Glu Arg Ile Pro Trp Ile Ala Pro Glu Cys Val Glu Asp Ser Lys
             185                 190                     195

Asn Leu Ser Val Ala Ala Asp Lys Trp Ser Phe Gly Thr Thr Leu
             200                 205                     210

Trp Glu Ile Cys Tyr Asn Gly Glu Ile Pro Leu Lys Asp Lys Thr
             215                 220                     225

Leu Ile Glu Lys Glu Arg Phe Tyr Glu Ser Arg Cys Arg Pro Val
             230                 235                     240

Thr Pro Ser Cys Lys Glu Leu Ala Asp Leu Met Thr Arg Cys Met
             245                 250                     255

Asn Tyr Asp Pro Asn Gln Arg Pro Phe Phe Arg Ala Ile Met Arg
             260                 265                     270

Asp Ile Asn Lys Leu Glu Glu Gln Asn Pro Asp Ile Val Ser Arg
             275                 280                     285

Lys Lys Asn Gln Pro Thr Glu Val Asp Pro Thr His Phe Thr Lys
             290                 295                     300

Arg Phe Leu Lys Arg Ile Arg Asp Leu Gly Glu Gly His Phe Gly
             305                 310                     315

Lys Val Glu Leu Cys Arg Tyr Asp Pro Glu Asp Asn Thr Gly Glu

|   |   |   |   |   | 320 |   |   |   |   | 325 |   |   |   |   | 330 |
|---|---|---|---|---|---|---|---|---|---|---|---|---|---|---|---|
| Gln | Val | Ala | Val | Lys | Ser | Leu | Lys | Pro | Glu | Ser | Gly | Gly | Asn | His |
|   |   |   |   | 335 |   |   |   |   | 340 |   |   |   |   | 345 |
| Ile | Ala | Asp | Leu | Lys | Lys | Glu | Ile | Glu | Ile | Leu | Arg | Asn | Leu | Tyr |
|   |   |   |   | 350 |   |   |   |   | 355 |   |   |   |   | 360 |
| His | Glu | Asn | Ile | Val | Lys | Tyr | Lys | Gly | Ile | Cys | Thr | Glu | Asp | Gly |
|   |   |   |   | 365 |   |   |   |   | 370 |   |   |   |   | 375 |
| Gly | Asn | Gly | Ile | Lys | Leu | Ile | Met | Glu | Phe | Leu | Pro | Ser | Gly | Ser |
|   |   |   |   | 380 |   |   |   |   | 385 |   |   |   |   | 390 |
| Leu | Lys | Glu | Tyr | Leu | Pro | Lys | Asn | Lys | Asn | Lys | Ile | Asn | Leu | Lys |
|   |   |   |   | 395 |   |   |   |   | 400 |   |   |   |   | 405 |
| Gln | Gln | Leu | Lys | Tyr | Ala | Val | Gln | Ile | Cys | Lys | Gly | Met | Asp | Tyr |
|   |   |   |   | 410 |   |   |   |   | 415 |   |   |   |   | 420 |
| Leu | Gly | Ser | Arg | Gln | Tyr | Val | His | Arg | Asp | Leu | Ala | Ala | Arg | Asn |
|   |   |   |   | 425 |   |   |   |   | 430 |   |   |   |   | 435 |
| Val | Leu | Val | Glu | Ser | Glu | His | Gln | Val | Lys | Ile | Gly | Asp | Phe | Gly |
|   |   |   |   | 440 |   |   |   |   | 445 |   |   |   |   | 450 |
| Leu | Thr | Lys | Ala | Ile | Glu | Thr | Asp | Lys | Glu | Tyr | Tyr | Thr | Val | Lys |
|   |   |   |   | 455 |   |   |   |   | 460 |   |   |   |   | 465 |
| Asp | Asp | Arg | Asp | Ser | Pro | Val | Phe | Trp | Tyr | Ala | Pro | Glu | Cys | Leu |
|   |   |   |   | 470 |   |   |   |   | 475 |   |   |   |   | 480 |
| Met | Gln | Ser | Lys | Phe | Tyr | Ile | Ala | Ser | Asp | Val | Trp | Ser | Phe | Gly |
|   |   |   |   | 485 |   |   |   |   | 490 |   |   |   |   | 495 |
| Val | Thr | Leu | His | Glu | Leu | Leu | Thr | Tyr | Cys | Asp | Ser | Asp | Ser | Ser |
|   |   |   |   | 500 |   |   |   |   | 505 |   |   |   |   | 510 |
| Pro | Met | Ala | Leu | Phe | Leu | Lys | Met | Ile | Gly | Pro | Thr | His | Gly | Gln |
|   |   |   |   | 515 |   |   |   |   | 520 |   |   |   |   | 525 |
| Met | Thr | Val | Thr | Arg | Leu | Val | Asn | Thr | Leu | Lys | Glu | Gly | Lys | Arg |
|   |   |   |   | 530 |   |   |   |   | 535 |   |   |   |   | 540 |
| Leu | Pro | Cys | Pro | Pro | Asn | Cys | Pro | Asp | Glu | Val | Tyr | Gln | Leu | Met |
|   |   |   |   | 545 |   |   |   |   | 550 |   |   |   |   | 555 |
| Arg | Lys | Cys | Trp | Glu | Phe | Gln | Pro | Ser | Asn | Arg | Thr | Ser | Phe | Gln |
|   |   |   |   | 560 |   |   |   |   | 565 |   |   |   |   | 570 |
| Asn | Leu | Ile | Glu | Gly | Phe | Glu | Ala | Leu | Leu | Lys |   |   |   |   |
|   |   |   |   | 575 |   |   |   |   | 580 |   |   |   |   |   |

(2) INFORMATION FOR SEQ ID NO: 18:

(i) SEQUENCE CHARACTERISTICS:
        (A) LENGTH: 1132 amino acids
        (B) TYPE: amino acid
        (D) TOPOLOGY: linear (xi) SEQUENCE DESCRIPTION: SEQ ID NO: 18:

|   |   |   |   |   |   |   |   |   |   |   |   |   |   |   |
|---|---|---|---|---|---|---|---|---|---|---|---|---|---|---|
| Met | Gln | Tyr | Leu | Asn | Ile | Lys | Glu | Asp | Cys | Asn | Ala | Met | Ala | Phe |
|   |   |   |   | 5 |   |   |   |   | 10 |   |   |   |   | 15 |
| Cys | Ala | Lys | Met | Arg | Ser | Ser | Lys | Lys | Thr | Glu | Val | Asn | Leu | Glu |
|   |   |   |   | 20 |   |   |   |   | 25 |   |   |   |   | 30 |
| Ala | Pro | Glu | Pro | Gly | Val | Glu | Val | Ile | Phe | Tyr | Leu | Ser | Asp | Arg |
|   |   |   |   | 35 |   |   |   |   | 40 |   |   |   |   | 45 |
| Glu | Pro | Leu | Arg | Leu | Gly | Ser | Gly | Glu | Tyr | Thr | Ala | Glu | Glu | Leu |
|   |   |   |   | 50 |   |   |   |   | 55 |   |   |   |   | 60 |
| Cys | Ile | Arg | Ala | Ala | Gln | Ala | Cys | Arg | Ile | Ser | Pro | Leu | Cys | His |
|   |   |   |   | 65 |   |   |   |   | 70 |   |   |   |   | 75 |
| Asn | Leu | Phe | Ala | Leu | Tyr | Asp | Glu | Asn | Thr | Lys | Leu | Trp | Tyr | Ala |
|   |   |   |   | 80 |   |   |   |   | 85 |   |   |   |   | 90 |

```
Pro Asn Arg Thr Ile Thr Val Asp Asp Lys Met Ser Leu Arg Leu
                95                 100                     105

His Tyr Arg Met Arg Phe Tyr Phe Thr Asn Trp His Gly Thr Asn
                110                 115                     120

Asp Asn Glu Gln Ser Val Trp Arg His Ser Pro Lys Lys Gln Lys
                125                 130                     135

Asn Gly Tyr Glu Lys Lys Lys Ile Pro Asp Ala Thr Pro Leu Leu
                140                 145                     150

Asp Ala Ser Ser Leu Glu Tyr Leu Phe Ala Gln Gly Gln Tyr Asp
                155                 160                     165

Leu Val Lys Cys Leu Ala Pro Ile Arg Asp Pro Lys Thr Glu Gln
                170                 175                     180

Asp Gly His Asp Ile Glu Asn Glu Cys Leu Gly Met Ala Val Leu
                185                 190                     195

Ala Ile Ser His Tyr Ala Met Met Lys Lys Met Gln Leu Pro Glu
                200                 205                     210

Leu Pro Lys Asp Ile Ser Tyr Lys Arg Tyr Ile Pro Glu Thr Leu
                215                 220                     225

Asn Lys Ser Ile Arg Gln Arg Asn Leu Leu Thr Arg Met Arg Ile
                230                 235                     240

Asn Asn Val Phe Lys Asp Phe Leu Lys Glu Phe Asn Asn Lys Thr
                245                 250                     255

Ile Cys Asp Ser Ser Val Ser Thr His Asp Leu Lys Val Lys Tyr
                260                 265                     270

Leu Ala Thr Leu Glu Thr Leu Thr Lys His Tyr Gly Ala Glu Ile
                275                 280                     285

Phe Glu Thr Ser Met Leu Leu Ile Ser Ser Glu Asn Glu Met Asn
                290                 295                     300

Trp Phe His Ser Asn Asp Gly Gly Asn Val Leu Tyr Tyr Glu Val
                305                 310                     315

Met Val Thr Gly Asn Leu Gly Ile Gln Trp Arg His Lys Pro Asn
                320                 325                     330

Val Val Ser Val Glu Lys Glu Lys Asn Lys Leu Lys Arg Lys Lys
                335                 340                     345

Leu Glu Asn Lys Asp Lys Lys Asp Glu Lys Asn Lys Ile Arg
                350                 355                     360

Glu Glu Trp Asn Asn Phe Ser Phe Phe Pro Glu Ile Thr His Ile
                365                 370                     375

Val Ile Lys Glu Ser Val Val Ser Ile Asn Lys Gln Asp Asn Lys
                380                 385                     390

Lys Met Glu Leu Lys Leu Ser Ser His Glu Glu Ala Leu Ser Phe
                395                 400                     405

Val Ser Leu Val Asp Gly Tyr Phe Arg Leu Thr Ala Asp Ala His
                410                 415                     420

His Tyr Leu Cys Thr Asp Val Ala Pro Pro Leu Ile Val His Asn
                425                 430                     435

Ile Gln Asn Gly Cys His Gly Pro Ile Cys Glu Tyr Ala Ile Asn
                440                 445                     450

Lys Leu Arg Gln Glu Gly Ser Glu Glu Gly Met Tyr Val Leu Arg
                455                 460                     465

Trp Ser Cys Thr Asp Phe Asp Asn Ile Leu Met Thr Val Thr Cys
                470                 475                     480

Phe Glu Lys Ser Glu Gln Val Gln Gly Ala Gln Lys Gln Phe Lys
```

-continued

```
                    485                      490                      495
Asn  Phe  Gln  Ile  Glu  Val  Gln  Lys  Gly  Arg  Tyr  Ser  Leu  His  Gly
                    500                      505                      510

Ser  Asp  Arg  Ser  Phe  Pro  Ser  Leu  Gly  Asp  Leu  Met  Ser  His  Leu
                    515                      520                      525

Lys  Lys  Gln  Ile  Leu  Arg  Thr  Asp  Asn  Ile  Ser  Phe  Met  Leu  Lys
                    530                      535                      540

Arg  Cys  Cys  Gln  Pro  Lys  Pro  Arg  Glu  Ile  Ser  Asn  Leu  Leu  Val
                    545                      550                      555

Ala  Thr  Lys  Lys  Ala  Gln  Glu  Trp  Gln  Pro  Val  Tyr  Pro  Met  Ser
                    560                      565                      570

Gln  Leu  Ser  Phe  Asp  Arg  Ile  Leu  Lys  Lys  Asp  Leu  Val  Gln  Gly
                    575                      580                      585

Glu  His  Leu  Gly  Arg  Gly  Thr  Arg  Thr  His  Ile  Tyr  Ser  Gly  Thr
                    590                      595                      600

Leu  Met  Asp  Tyr  Lys  Asp  Asp  Glu  Gly  Thr  Ser  Glu  Glu  Lys  Lys
                    605                      610                      615

Ile  Lys  Val  Ile  Leu  Lys  Val  Leu  Asp  Pro  Ser  His  Arg  Asp  Ile
                    620                      625                      630

Ser  Leu  Ala  Phe  Phe  Glu  Ala  Ala  Ser  Met  Met  Arg  Gln  Val  Ser
                    635                      640                      645

His  Lys  His  Ile  Val  Tyr  Leu  Tyr  Gly  Val  Cys  Val  Arg  Asp  Val
                    650                      655                      660

Glu  Asn  Ile  Met  Val  Glu  Glu  Phe  Val  Glu  Gly  Gly  Pro  Leu  Asp
                    665                      670                      675

Leu  Phe  Met  His  Arg  Lys  Ser  Asp  Val  Leu  Thr  Thr  Pro  Trp  Lys
                    680                      685                      690

Phe  Lys  Val  Ala  Lys  Gln  Leu  Ala  Ser  Ala  Leu  Ser  Tyr  Leu  Glu
                    695                      700                      705

Asp  Lys  Asp  Leu  Val  His  Gly  Asn  Val  Cys  Thr  Lys  Asn  Leu  Leu
                    710                      715                      720

Leu  Ala  Arg  Glu  Gly  Ile  Asp  Ser  Glu  Cys  Gly  Pro  Phe  Ile  Lys
                    725                      730                      735

Leu  Ser  Asp  Pro  Gly  Ile  Pro  Ile  Thr  Val  Leu  Ser  Arg  Gln  Glu
                    740                      745                      750

Cys  Ile  Glu  Arg  Ile  Pro  Trp  Ile  Ala  Pro  Glu  Cys  Val  Glu  Asp
                    755                      760                      765

Ser  Lys  Asn  Leu  Ser  Val  Ala  Ala  Asp  Lys  Trp  Ser  Phe  Gly  Thr
                    770                      775                      780

Thr  Leu  Trp  Glu  Ile  Cys  Tyr  Asn  Gly  Glu  Ile  Pro  Leu  Lys  Asp
                    785                      790                      795

Lys  Thr  Leu  Ile  Glu  Lys  Glu  Arg  Phe  Tyr  Glu  Ser  Arg  Cys  Arg
                    800                      805                      810

Pro  Val  Thr  Pro  Ser  Cys  Lys  Glu  Leu  Ala  Asp  Leu  Met  Thr  Arg
                    815                      820                      825

Cys  Met  Asn  Tyr  Asp  Pro  Asn  Gln  Arg  Pro  Phe  Phe  Arg  Ala  Ile
                    830                      835                      840

Met  Arg  Asp  Ile  Asn  Lys  Leu  Glu  Glu  Gln  Asn  Pro  Asp  Ile  Val
                    845                      850                      855

Ser  Arg  Lys  Lys  Asn  Gln  Pro  Thr  Glu  Val  Asp  Pro  Thr  His  Phe
                    860                      865                      870

Lys  Arg  Phe  Leu  Lys  Arg  Ile  Arg  Asp  Leu  Gly  Glu  Gly  His  Phe
                    875                      880                      885
```

| Gly | Lys | Val | Glu | Leu | Cys | Arg | Tyr | Asp | Pro | Glu | Asp | Asn | Thr | Gly |
|---|---|---|---|---|---|---|---|---|---|---|---|---|---|---|
| | | | | 890 | | | | 895 | | | | | | 900 |
| Glu | Gln | Val | Ala | Val | Lys | Ser | Leu | Lys | Pro | Glu | Ser | Gly | Gly | Asn |
| | | | | 905 | | | | 910 | | | | | | 915 |
| His | Ile | Ala | Asp | Leu | Lys | Lys | Glu | Ile | Glu | Ile | Leu | Arg | Asn | Leu |
| | | | | 920 | | | | 925 | | | | | | 930 |
| Tyr | His | Glu | Asn | Ile | Val | Lys | Tyr | Lys | Gly | Ile | Cys | Thr | Glu | Asp |
| | | | | 935 | | | | 940 | | | | | | 945 |
| Gly | Gly | Asn | Gly | Ile | Lys | Leu | Ile | Met | Glu | Phe | Leu | Pro | Ser | Gly |
| | | | | 950 | | | | 955 | | | | | | 960 |
| Ser | Leu | Lys | Glu | Tyr | Leu | Pro | Lys | Asn | Lys | Asn | Lys | Ile | Asn | Leu |
| | | | | 965 | | | | 970 | | | | | | 975 |
| Lys | Gln | Gln | Leu | Lys | Tyr | Ala | Val | Gln | Ile | Cys | Lys | Gly | Met | Asp |
| | | | | 980 | | | | 985 | | | | | | 990 |
| Tyr | Leu | Gly | Ser | Arg | Gln | Tyr | Val | His | Arg | Asp | Leu | Ala | Ala | Arg |
| | | | | 995 | | | | 1000 | | | | | | 1005 |
| Asn | Val | Leu | Val | Glu | Ser | Glu | His | Gln | Val | Lys | Ile | Gly | Asp | Phe |
| | | | | 1010 | | | | 1015 | | | | | | 1020 |
| Gly | Leu | Thr | Lys | Ala | Ile | Glu | Thr | Asp | Lys | Glu | Tyr | Tyr | Thr | Val |
| | | | | 1025 | | | | 1030 | | | | | | 1035 |
| Lys | Asp | Asp | Arg | Asp | Ser | Pro | Val | Phe | Trp | Tyr | Ala | Pro | Glu | Cys |
| | | | | 1040 | | | | 1045 | | | | | | 1050 |
| Leu | Met | Gln | Ser | Lys | Phe | Tyr | Ile | Ala | Ser | Asp | Val | Trp | Ser | Phe |
| | | | | 1055 | | | | 1060 | | | | | | 1065 |
| Gly | Val | Thr | Leu | His | Glu | Leu | Leu | Thr | Tyr | Cys | Asp | Ser | Asp | Ser |
| | | | | 1070 | | | | 1075 | | | | | | 1080 |
| Ser | Pro | Met | Ala | Leu | Phe | Leu | Lys | Met | Ile | Gly | Pro | Thr | His | Gly |
| | | | | 1085 | | | | 1090 | | | | | | 1095 |
| Gln | Met | Thr | Val | Thr | Arg | Leu | Val | Asn | Thr | Leu | Lys | Glu | Gly | Lys |
| | | | | 1100 | | | | 1105 | | | | | | 1110 |
| Arg | Leu | Pro | Cys | Pro | Pro | Asn | Cys | Pro | Asp | Glu | Val | Tyr | Gln | Leu |
| | | | | 1115 | | | | 1120 | | | | | | 1125 |
| Met | Arg | Lys | Cys | Trp | Glu | Phe | | | | | | | | |
| | | | | 1130 | | | | | | | | | | |

(2) INFORMATION FOR SEQ ID NO: 19:

(i) SEQUENCE CHARACTERISTICS:
        (A) LENGTH: 971 amino acids
        (B) TYPE: amino acid
        (D) TOPOLOGY: linear (xi) SEQUENCE DESCRIPTION: SEQ ID NO: 19:

| Leu | Leu | Asp | Asp | Phe | Val | Met | Ser | Tyr | Leu | Ser | Pro | Gln | Trp | Arg |
|---|---|---|---|---|---|---|---|---|---|---|---|---|---|---|
| | | | | 5 | | | | 10 | | | | | | 15 |
| His | Asp | Phe | Val | His | Gly | Trp | Ile | Lys | Val | Pro | Val | Thr | His | Glu |
| | | | | 20 | | | | 25 | | | | | | 30 |
| Thr | Gln | Glu | Glu | Cys | Leu | Gly | Met | Ala | Val | Leu | Asp | Met | Met | Arg |
| | | | | 35 | | | | 40 | | | | | | 45 |
| Ile | Ala | Lys | Glu | Lys | Asp | Gln | Thr | Pro | Leu | Ala | Val | Tyr | Asn | Ser |
| | | | | 50 | | | | 55 | | | | | | 60 |
| Val | Ser | Tyr | Lys | Thr | Phe | Leu | Pro | Lys | Cys | Val | Arg | Ala | Lys | Ile |
| | | | | 65 | | | | 70 | | | | | | 75 |
| Gln | Asp | Tyr | His | Ile | Leu | Thr | Arg | Lys | Arg | Ile | Arg | Tyr | Arg | Phe |
| | | | | 80 | | | | 85 | | | | | | 90 |
| Arg | Arg | Phe | Ile | Gln | Gln | Phe | Ser | Gln | Cys | Lys | Ala | Thr | Ala | Arg |

-continued

|     |     |     |     | 95  |     |     |     |     | 100 |     |     |     |     | 105 |
|-----|-----|-----|-----|-----|-----|-----|-----|-----|-----|-----|-----|-----|-----|-----|
| Asn | Leu | Lys | Leu | Lys | Tyr | Leu | Ile | Asn | Leu | Glu | Thr | Leu | Gln | Ser |
|     |     |     |     | 110 |     |     |     |     | 115 |     |     |     |     | 120 |
| Ala | Phe | Tyr | Thr | Glu | Gln | Phe | Glu | Val | Lys | Glu | Ser | Ala | Arg | Gly |
|     |     |     |     | 125 |     |     |     |     | 130 |     |     |     |     | 135 |
| Pro | Ser | Gly | Glu | Glu | Ile | Phe | Ala | Thr | Ile | Ile | Ile | Thr | Gly | Asn |
|     |     |     |     | 140 |     |     |     |     | 145 |     |     |     |     | 150 |
| Gly | Gly | Ile | Gln | Trp | Ser | Arg | Gly | Lys | His | Lys | Glu | Ser | Glu | Thr |
|     |     |     |     | 155 |     |     |     |     | 160 |     |     |     |     | 165 |
| Leu | Thr | Glu | Gln | Asp | Leu | Gln | Leu | Tyr | Cys | Asp | Phe | Pro | Asp | Ile |
|     |     |     |     | 170 |     |     |     |     | 175 |     |     |     |     | 180 |
| Ile | Asp | Val | Ser | Ile | Lys | Gln | Ala | Asn | Gln | Glu | Cys | Ser | Thr | Glu |
|     |     |     |     | 185 |     |     |     |     | 190 |     |     |     |     | 195 |
| Ser | Arg | Ile | Val | Thr | Val | His | Lys | Gln | Asp | Gly | Glu | Val | Leu | Glu |
|     |     |     |     | 200 |     |     |     |     | 205 |     |     |     |     | 210 |
| Ile | Glu | Leu | Ser | Ser | Leu | Lys | Glu | Ala | Leu | Ser | Phe | Val | Ser | Leu |
|     |     |     |     | 215 |     |     |     |     | 220 |     |     |     |     | 225 |
| Ile | Asp | Gly | Tyr | Tyr | Arg | Leu | Thr | Ala | Asp | Ala | His | His | Tyr | Leu |
|     |     |     |     | 230 |     |     |     |     | 235 |     |     |     |     | 240 |
| Cys | Lys | Glu | Val | Ala | Pro | Pro | Ala | Val | Leu | Glu | Asn | Ile | His | Ser |
|     |     |     |     | 245 |     |     |     |     | 250 |     |     |     |     | 255 |
| Asn | Cys | His | Gly | Pro | Ile | Ser | Met | Asp | Phe | Ala | Ile | Ser | Lys | Leu |
|     |     |     |     | 260 |     |     |     |     | 265 |     |     |     |     | 270 |
| Lys | Lys | Ala | Gly | Asn | Gln | Thr | Gly | Leu | Tyr | Val | Leu | Arg | Cys | Ser |
|     |     |     |     | 275 |     |     |     |     | 280 |     |     |     |     | 285 |
| Pro | Lys | Asp | Phe | Asn | Lys | Tyr | Phe | Leu | Thr | Phe | Ala | Val | Glu | Arg |
|     |     |     |     | 290 |     |     |     |     | 295 |     |     |     |     | 300 |
| Glu | Asn | Val | Ile | Glu | Tyr | Lys | His | Cys | Leu | Ile | Thr | Lys | Asn | Glu |
|     |     |     |     | 305 |     |     |     |     | 310 |     |     |     |     | 315 |
| Asn | Gly | Glu | Tyr | Asn | Leu | Ser | Gly | Thr | Lys | Arg | Asn | Phe | Ser | Ser |
|     |     |     |     | 320 |     |     |     |     | 325 |     |     |     |     | 330 |
| Leu | Lys | Asp | Leu | Leu | Asn | Cys | Tyr | Gln | Met | Glu | Thr | Val | Arg | Ser |
|     |     |     |     | 335 |     |     |     |     | 340 |     |     |     |     | 345 |
| Asp | Ser | Ile | Ile | Phe | Gln | Phe | Thr | Lys | Cys | Cys | Pro | Pro | Lys | Pro |
|     |     |     |     | 350 |     |     |     |     | 355 |     |     |     |     | 360 |
| Lys | Asp | Lys | Ser | Asn | Leu | Leu | Val | Phe | Arg | Thr | Asn | Gly | Val | Ser |
|     |     |     |     | 365 |     |     |     |     | 370 |     |     |     |     | 375 |
| Asp | Val | Gln | Leu | Ser | Pro | Thr | Leu | Gln | Arg | His | Asn | Asn | Val | Asn |
|     |     |     |     | 380 |     |     |     |     | 385 |     |     |     |     | 390 |
| Gln | Met | Val | Phe | His | Lys | Ile | Arg | Asn | Glu | Asp | Leu | Ile | Phe | Asn |
|     |     |     |     | 395 |     |     |     |     | 400 |     |     |     |     | 405 |
| Glu | Ser | Leu | Gly | Gln | Gly | Thr | Phe | Thr | Lys | Ile | Phe | Lys | Gly | Val |
|     |     |     |     | 410 |     |     |     |     | 415 |     |     |     |     | 420 |
| Arg | Arg | Glu | Val | Gly | Asp | Tyr | Gly | Gln | Leu | His | Glu | Thr | Glu | Val |
|     |     |     |     | 425 |     |     |     |     | 430 |     |     |     |     | 435 |
| Leu | Leu | Lys | Val | Leu | Asp | Lys | Ala | His | Arg | Asn | Tyr | Ser | Glu | Ser |
|     |     |     |     | 440 |     |     |     |     | 445 |     |     |     |     | 450 |
| Phe | Phe | Glu | Ala | Ala | Ser | Met | Met | Ser | Gln | Leu | Ser | His | Lys | His |
|     |     |     |     | 455 |     |     |     |     | 460 |     |     |     |     | 465 |
| Leu | Val | Leu | Asn | Tyr | Gly | Val | Cys | Val | Cys | Gly | Glu | Glu | Asn | Ile |
|     |     |     |     | 470 |     |     |     |     | 475 |     |     |     |     | 480 |
| Leu | Val | Gln | Glu | Phe | Val | Lys | Phe | Gly | Ser | Leu | Asp | Thr | Tyr | Leu |
|     |     |     |     | 485 |     |     |     |     | 490 |     |     |     |     | 495 |

```
Lys  Lys  Asn  Lys  Asn  Ser  Ile  Asn  Ile  Leu  Trp  Lys  Leu  Gly  Val
               500                 505                           510

Ala  Lys  Gln  Leu  Ala  Trp  Ala  Met  His  Phe  Leu  Glu  Glu  Lys  Ser
               515                 520                           525

Leu  Ile  His  Gly  Asn  Val  Cys  Ala  Lys  Asn  Ile  Leu  Leu  Ile  Arg
               530                 535                           540

Glu  Glu  Asp  Arg  Arg  Thr  Gly  Asn  Pro  Phe  Ile  Lys  Leu  Ser  Asp
               545                 550                           555

Pro  Gly  Ile  Ser  Ile  Thr  Val  Leu  Pro  Lys  Asp  Ile  Ser  Ser  Cys
               560                 565                           570

Cys  Phe  Gln  Val  Leu  Gln  Glu  Arg  Ile  Pro  Trp  Val  Pro  Pro  Glu
               575                 580                           585

Cys  Ile  Glu  Asn  Pro  Lys  Asn  Leu  Thr  Leu  Ala  Thr  Asp  Lys  Trp
               590                 595                           600

Ser  Phe  Gly  Thr  Thr  Leu  Trp  Glu  Ile  Cys  Ser  Gly  Gly  Asp  Lys
               605                 610                           615

Pro  Leu  Ser  Ala  Leu  Asp  Ser  Gln  Arg  Lys  Leu  Gln  Phe  Tyr  Glu
               620                 625                           630

Asp  Lys  His  Gln  Leu  Pro  Ala  Pro  Lys  Trp  Thr  Glu  Leu  Ala  Asn
               635                 640                           645

Leu  Ile  Asn  Asn  Cys  Met  Asp  Tyr  Glu  Pro  Asp  Phe  Arg  Pro  Ala
               650                 655                           660

Phe  Arg  Ala  Val  Ile  Arg  Asp  Leu  Asn  Ser  Leu  Phe  Thr  Pro  Asp
               665                 670                           675

Tyr  Glu  Leu  Leu  Thr  Glu  Asn  Asp  Met  Leu  Pro  Asn  Met  Arg  Ile
               680                 685                           690

Gly  Ala  Leu  Gly  Phe  Ser  Gly  Ala  Phe  Glu  Asp  Arg  Asp  Pro  Thr
               695                 700                           705

Gln  Phe  Glu  Glu  Arg  His  Leu  Lys  Phe  Leu  Gln  Gln  Leu  Gly  Lys
               710                 715                           720

Gly  Asn  Phe  Gly  Ser  Val  Glu  Met  Cys  Arg  Tyr  Asp  Pro  Leu  Gln
               725                 730                           735

Asp  Asn  Thr  Gly  Glu  Val  Val  Ala  Val  Lys  Lys  Leu  Gln  His  Ser
               740                 745                           750

Thr  Glu  Glu  His  Leu  Arg  Asp  Phe  Glu  Arg  Glu  Ile  Glu  Ile  Leu
               755                 760                           765

Lys  Ser  Leu  Gln  His  Asp  Asn  Ile  Val  Lys  Tyr  Lys  Gly  Val  Cys
               770                 775                           780

Tyr  Ser  Ala  Gly  Arg  Arg  Asn  Leu  Arg  Leu  Ile  Met  Glu  Tyr  Leu
               785                 790                           795

Pro  Tyr  Gly  Ser  Leu  Arg  Asp  Tyr  Leu  Gln  Lys  His  Lys  Glu  Arg
               800                 805                           810

Ile  Asp  His  Lys  Lys  Leu  Leu  Gln  Tyr  Thr  Ser  Gln  Ile  Cys  Lys
               815                 820                           825

Gly  Met  Glu  Tyr  Leu  Gly  Thr  Lys  Arg  Tyr  Ile  His  Arg  Asp  Leu
               830                 835                           840

Ala  Thr  Arg  Asn  Ile  Leu  Val  Glu  Asn  Glu  Asn  Arg  Val  Lys  Ile
               845                 850                           855

Gly  Asp  Phe  Gly  Leu  Thr  Lys  Val  Leu  Pro  Gln  Asp  Lys  Glu  Tyr
               860                 865                           870

Tyr  Lys  Val  Lys  Glu  Pro  Gly  Glu  Ser  Pro  Ile  Phe  Trp  Tyr  Ala
               875                 880                           885

Pro  Glu  Ser  Leu  Thr  Glu  Ser  Lys  Phe  Ser  Val  Ala  Ser  Asp  Val
               890                 895                           900
```

| Trp | Ser | Phe | Gly | Val<br>905 | Val | Leu | Tyr | Glu | Leu<br>910 | Phe | Thr | Tyr | Ile | Glu<br>915 |

| Lys | Ser | Lys | Ser | Pro<br>920 | Pro | Val | Glu | Phe | Met<br>925 | Arg | Met | Ile | Gly | Asn<br>930 |

| Asp | Lys | Gln | Gly | Gln<br>935 | Met | Ile | Val | Phe | His<br>940 | Leu | Ile | Glu | Leu | Leu<br>945 |

| Lys | Ser | Asn | Gly | Arg<br>950 | Leu | Pro | Arg | Pro | Glu<br>955 | Gly | Cys | Pro | Asp | Glu<br>960 |

| Ile | Tyr | Val | Ile | Met<br>965 | Thr | Glu | Cys | Trp | Asn<br>970 | Asn | | | | |

(2) INFORMATION FOR SEQ ID NO:20:

(i) SEQUENCE CHARACTERISTICS:
        (A) LENGTH: 1184 amino acids
        (B) TYPE: amino acid
        (D) TOPOLOGY: linear (xi) SEQUENCE DESCRIPTION: SEQ ID NO:20:

| Met | Pro | Leu | Arg | His<br>5 | Trp | Gly | Met | Ala | Arg<br>10 | Gly | Ser | Lys | Pro | Val<br>15 |

| Gly | Asp | Gly | Ala | Gln<br>20 | Pro | Met | Ala | Ala | Met<br>25 | Gly | Gly | Leu | Lys | Val<br>30 |

| Leu | Leu | His | Trp | Ala<br>35 | Gly | Pro | Gly | Gly | Glu<br>40 | Pro | Trp | Val | Thr<br>45 | |

| Phe | Ser | Glu | Ser | Ser<br>50 | Leu | Ile | Ala | Glu | Val<br>55 | Cys | Ile | His | Ile<br>60 | |

| Ala | His | Lys | Val | Gly<br>65 | Ile | Thr | Pro | Pro | Cys<br>70 | Phe | Asn | Leu | Phe | Ala<br>75 |

| Leu | Phe | Asp | Ala | Gln<br>80 | Ala | Gln | Val | Trp | Leu<br>85 | Pro | Pro | Asn | His | Ile<br>90 |

| Leu | Glu | Ile | Pro | Arg<br>95 | Asp | Ala | Ser | Leu | Met<br>100 | Leu | Tyr | Phe | Arg | Ile<br>105 |

| Arg | Phe | Tyr | Phe | Arg<br>110 | Asn | Trp | His | Gly | Met<br>115 | Asn | Pro | Arg | Glu | Pro<br>120 |

| Ala | Gly | Tyr | Arg | Cys<br>125 | Gly | Pro | Pro | Gly | Thr<br>130 | Glu | Ala | Ser | Ser | Asp<br>135 |

| Gln | Thr | Ala | Gln | Gly<br>140 | Met | Gln | Leu | Leu | Asp<br>145 | Pro | Ala | Ser | Phe | Glu<br>150 |

| Tyr | Leu | Phe | Glu | Gln<br>155 | Gly | Lys | His | Glu | Phe<br>160 | Glu | Asn | Asp | Val | Ala<br>165 |

| Ser | Leu | Trp | Glu | Leu<br>170 | Ser | Thr | Glu | Glu | Glu<br>175 | Ile | His | His | Phe | Lys<br>180 |

| Asn | Glu | Ser | Leu | Gly<br>185 | Met | Ala | Phe | Leu | His<br>190 | Leu | Cys | His | Leu | Ala<br>195 |

| Leu | Arg | His | Gly | Ile<br>200 | Pro | Leu | Glu | Glu | Val<br>205 | Ala | Lys | Lys | Thr | Ser<br>210 |

| Phe | Lys | Asp | Cys | Ile<br>215 | Pro | Arg | Ser | Phe | Arg<br>220 | Arg | His | Ile | Arg | Gln<br>225 |

| His | Ser | Ala | Leu | Thr<br>230 | Arg | Leu | Arg | Leu | Arg<br>235 | Asn | Val | Phe | Arg | Arg<br>240 |

| Phe | Leu | Arg | Asp | Phe<br>245 | Gln | Pro | Gly | Arg | Leu<br>250 | Ser | Gln | Gln | Met | Val<br>255 |

| Met | Val | Lys | Tyr | Leu<br>260 | Ala | Thr | Leu | Glu | Arg<br>265 | Leu | Ala | Pro | Arg | Phe<br>270 |

-continued

| | | | | | | | | | | | | | | |
|---|---|---|---|---|---|---|---|---|---|---|---|---|---|---|
|Gly|Thr|Glu|Arg|Val 275|Pro|Val|Cys|His|Leu 280|Arg|Leu|Leu|Ala|Gln 285|
|Ala|Glu|Gly|Glu|Pro 290|Cys|Tyr|Ile|Arg|Asp 295|Ser|Gly|Val|Ala|Pro 300|
|Thr|Asp|Pro|Gly|Pro 305|Glu|Ser|Ala|Ala|Gly 310|Pro|Pro|Thr|His|Glu 315|
|Val|Leu|Val|Thr|Gly 320|Thr|Gly|Gly|Ile|Gln 325|Trp|Trp|Pro|Val|Glu 330|
|Glu|Glu|Val|Asn|Lys 335|Glu|Glu|Gly|Ser|Ser 340|Gly|Ser|Ser|Ala|Arg 345|
|Asn|Pro|Gln|Ala|Ser 350|Leu|Phe|Gly|Lys|Lys 355|Ala|Lys|Ala|His|Lys 360|
|Ala|Phe|Gly|Gln|Pro 365|Ala|Asp|Arg|Pro|Arg 370|Glu|Pro|Leu|Trp|Ala 375|
|Tyr|Phe|Cys|Asp|Ile 380|Thr|His|Val|Val|Leu 385|Lys|Glu|His|Cys|Val 390|
|Ser|Ile|His|Arg|Gln 395|Asp|Asn|Lys|Cys|Leu 400|Glu|Leu|Ser|Leu|Pro 405|
|Ser|Arg|Ala|Ala|Ala 410|Leu|Ser|Phe|Glu|Ser 415|Leu|Val|Asp|Gly|Tyr 420|
|Phe|Arg|Leu|Thr|Ala 425|Asp|Ser|Ser|His|Tyr 430|Leu|Cys|His|Glu|Val 435|
|Ala|Pro|Pro|Arg|Leu 440|Val|Met|Ser|Ile|Arg 445|Asp|Gly|Ile|His|Gly 450|
|Pro|Leu|Leu|Glu|Pro 455|Phe|Val|Gln|Gln|Ala 460|Lys|Leu|Arg|Pro|Leu 465|
|Glu|Asp|Gly|Leu|Tyr 470|Leu|Ile|His|Trp|Ser 475|Thr|Ser|His|Pro|Tyr 480|
|Arg|Leu|Ile|Leu|Thr 485|Val|Ala|Gln|Arg|Ser 490|Gln|Ala|Pro|Asp|Gly 495|
|Met|Gln|Ser|Leu|Arg 500|Leu|Arg|Lys|Phe|Pro 505|Ile|Glu|Gln|Gln|Asp 510|
|Gly|Ala|Phe|Val|Leu 515|Glu|Gly|Trp|Gly|Arg 520|Ser|Phe|Pro|Ser|Val 525|
|Arg|Glu|Leu|Gly|Ala 530|Ala|Leu|Gln|Gly|Cys 535|Leu|Leu|Arg|Ala|Gly 540|
|Asp|Asp|Cys|Phe|Ser 545|Leu|Arg|Arg|Cys|Cys 550|Leu|Pro|Gln|Pro|Gly 555|
|Glu|Thr|Ser|Asn|Leu 560|Ile|Ile|Met|Arg|Gly 565|Ala|Arg|Ala|Ser|Pro 570|
|Arg|Thr|Leu|Asn|Leu 575|Ser|Gln|Leu|Ser|Phe 580|His|Arg|Val|Asp|Gln 585|
|Lys|Glu|Ile|Thr|Gln 590|Leu|Ser|His|Leu|Gly 595|Gln|Gly|Thr|Arg|Thr 600|
|Asn|Val|Tyr|Glu|Gly 605|Arg|Leu|Arg|Val|Glu 610|Gly|Ser|Gly|Asp|Pro 615|
|Glu|Glu|Gly|Lys|Met 620|Asp|Asp|Glu|Asp|Pro 625|Leu|Val|Pro|Gly|Arg 630|
|Asp|Arg|Gly|Gln|Glu 635|Leu|Arg|Val|Val|Leu 640|Lys|Val|Leu|Asp|Pro 645|
|Ser|His|His|Asp|Ile 650|Ala|Leu|Ala|Phe|Tyr 655|Glu|Thr|Ala|Ser|Leu 660|
|Met|Ser|Gln|Val|Ser 665|His|Thr|His|Leu|Ala 670|Phe|Val|His|Gly|Val 675|

-continued

```
Cys  Val  Arg  Gly  Pro  Glu  Asn  Ser  Met  Val  Thr  Glu  Tyr  Val  Glu
                    680                 685                 690

His  Gly  Pro  Leu  Asp  Val  Trp  Leu  Arg  Arg  Glu  Arg  Gly  His  Val
                    695                 700                 705

Pro  Met  Ala  Trp  Lys  Met  Val  Val  Ala  Gln  Gln  Leu  Ala  Ser  Ala
                    710                 715                 720

Leu  Ser  Tyr  Leu  Glu  Asn  Lys  Asn  Leu  Val  His  Gly  Asn  Val  Cys
                    725                 730                 735

Gly  Arg  Asn  Ile  Leu  Leu  Ala  Arg  Leu  Gly  Leu  Ala  Glu  Gly  Thr
                    740                 745                 750

Ser  Pro  Phe  Ile  Lys  Leu  Ser  Asp  Pro  Gly  Cys  Gly  Leu  Gly  Ala
                    755                 760                 765

Leu  Ser  Arg  Glu  Glu  Arg  Val  Glu  Arg  Ile  Pro  Trp  Leu  Ala  Pro
                    770                 775                 780

Glu  Cys  Leu  Pro  Gly  Gly  Ala  Asn  Ser  Leu  Ser  Thr  Ala  Met  Asp
                    785                 790                 795

Lys  Trp  Gly  Phe  Gly  Ala  Thr  Leu  Leu  Glu  Ile  Cys  Phe  Asp  Gly
                    800                 805                 810

Glu  Ala  Pro  Leu  Gln  Ser  Arg  Ser  Pro  Ser  Glu  Lys  Glu  His  Phe
                    815                 820                 825

Tyr  Gln  Arg  Gln  His  Arg  Leu  Pro  Glu  Pro  Ser  Cys  Pro  Gln  Leu
                    830                 835                 840

Ala  Thr  Leu  Thr  Ser  Gln  Cys  Leu  Thr  Tyr  Glu  Pro  Thr  Gln  Arg
                    845                 850                 855

Pro  Ser  Phe  Ala  Thr  Ile  Leu  Arg  Asp  Leu  Thr  Arg  Val  Gln  Pro
                    860                 865                 870

His  Asn  Leu  Ala  Asp  Val  Leu  Thr  Val  Asn  Arg  Asp  Ser  Pro  Ala
                    875                 880                 885

Val  Gly  Pro  Thr  Thr  Phe  His  Lys  Arg  Tyr  Leu  Lys  Lys  Ile  Arg
                    890                 895                 900

Asp  Leu  Gly  Glu  Gly  His  Phe  Gly  Lys  Val  Ser  Leu  Tyr  Cys  Tyr
                    905                 910                 915

Asp  Pro  Thr  Asn  Asp  Gly  Thr  Gly  Glu  Met  Val  Ala  Val  Lys  Ala
                    920                 925                 930

Leu  Lys  Ala  Asp  Cys  Gly  Pro  Gln  His  Arg  Ser  Gly  Trp  Lys  Gln
                    935                 940                 945

Glu  Ile  Asp  Ile  Leu  Arg  Thr  Leu  Tyr  His  Glu  His  Ile  Ile  Lys
                    950                 955                 960

Tyr  Lys  Gly  Cys  Cys  Glu  Asp  Gln  Gly  Glu  Lys  Ser  Leu  Val  Met
                    965                 970                 975

Glu  Tyr  Val  Pro  Leu  Gly  Ser  Leu  Arg  Asp  Tyr  Leu  Pro  Arg  His
                    980                 985                 990

Ser  Ile  Gly  Leu  Ala  Gln  Leu  Leu  Leu  Phe  Ala  Gln  Gln  Ile  Cys
                    995                1000                1005

Glu  Gly  Met  Ala  Tyr  Leu  His  Ala  His  Asp  Tyr  Ile  His  Arg  Asp
                   1010                1015                1020

Leu  Ala  Ala  Arg  Asn  Val  Leu  Leu  Asp  Asn  Asp  Arg  Leu  Val  Lys
                   1025                1030                1035

Ile  Gly  Asp  Phe  Gly  Leu  Ala  Lys  Ala  Val  Pro  Glu  Gly  His  Glu
                   1040                1045                1050

Tyr  Tyr  Arg  Val  Arg  Glu  Asp  Gly  Asp  Ser  Pro  Val  Phe  Trp  Tyr
                   1055                1060                1065

Ala  Pro  Glu  Cys  Leu  Lys  Glu  Tyr  Asn  Phe  Tyr  Tyr  Ala  Ser  Asp
```

|      |      |      |      |      |      |      |      | 1070 |      |      |      | 1075 |      |      |      | 1080 |      |
|---|---|---|---|---|---|---|---|---|---|---|---|---|---|---|---|---|---|

Val Trp Ser Phe Gly Val Thr Leu Tyr Glu Leu Leu Thr His Cys
                    1085                1090                    1095

Asp Ser Ser Gln Ser Pro Pro Thr Lys Phe Leu Glu Leu Ile Gly
                    1100                1105                    1110

Ile Ala Gln Gly Gln Met Thr Val Leu Arg Leu Thr Glu Leu Leu
                    1115                1120                    1125

Glu Arg Gly Glu Arg Leu Pro Arg Pro Asp Lys Cys Pro Cys Glu
                    1130                1135                    1140

Val Tyr His Leu Met Lys Asn Cys Trp Glu Thr Glu Ala Ser Phe
                    1145                1150                    1155

Arg Pro Thr Phe Glu Asn Ser Ile Pro Ile Leu Lys Thr Val His
                    1160                1165                    1170

Glu Lys Tyr Gln Gly Gln Ala Pro Ser Val Ser Ser Val Cys
                    1175                1180

(2) INFORMATION FOR SEQ ID NO:21:

(i) SEQUENCE CHARACTERISTICS:
  (A) LENGTH: 92 amino acids
  (B) TYPE: amino acid
  (D) TOPOLOGY: linear (xi) SEQUENCE DESCRIPTION: SEQ ID NO:21:

Trp Tyr His Gly Lys Leu Asp Arg Thr Ile Ala Glu Glu Arg Leu
                    5                   10                      15

Arg Gln Ala Gly Lys Ser Gly Ser Tyr Leu Ile Arg Glu Ser Asp
                    20                  25                      30

Arg Arg Pro Gly Ser Phe Val Leu Ser Phe Leu Ser Gln Thr Asn
                    35                  40                      45

Val Val Asn His Phe Arg Ile Ile Ala Met Cys Gly Asp Tyr Tyr
                    50                  55                      60

Ile Gly Gly Arg Arg Phe Ser Ser Leu Ser Asp Leu Ile Gly Tyr
                    65                  70                      75

Tyr Ser His Val Ser Cys Leu Leu Lys Gly Glu Lys Leu Leu Tyr
                    80                  85                      90

Pro Val (2) INFORMATION FOR SEQ ID NO:22:

(i) SEQUENCE CHARACTERISTICS:
  (A) LENGTH: 91 amino acids
  (B) TYPE: amino acid
  (D) TOPOLOGY: linear (xi) SEQUENCE DESCRIPTION: SEQ ID NO:22:

Trp Phe His Gly Lys Ile Ser Lys Gln Glu Ala Tyr Asn Leu Leu
                    5                   10                      15

Met Thr Val Gly Gln Ala Cys Ser Phe Leu Val Arg Pro Ser Asp
                    20                  25                      30

Asn Thr Pro Gly Asp Tyr Ser Leu Tyr Phe Arg Thr Ser Glu Asn
                    35                  40                      45

Ile Gln Arg Phe Lys Ile Cys Pro Thr Pro Asn Asn Gln Phe Met
                    50                  55                      60

Met Gly Gly Arg Tyr Tyr Asn Ser Ile Gly Asp Ile Ile Asp His
                    65                  70                      75

Tyr Arg Lys Glu Gln Ile Val Glu Gly Tyr Tyr Leu Lys Glu Pro
                    80                  85                      90

Val (2) INFORMATION FOR SEQ ID NO: 23:

(i) SEQUENCE CHARACTERISTICS:
        (A) LENGTH: 89 amino acids
        (B) TYPE: amino acid
        (D) TOPOLOGY: linear (xi) SEQUENCE DESCRIPTION: SEQ ID NO: 23:

```
Trp Tyr Trp Gly Arg Leu Ser Arg Gly Asp Ala Val Ser Leu Leu
                  5                   10                  15

Gln Gly Gln Arg His Gly Thr Phe Leu Val Arg Asp Ser Gly Ser
                 20                   25                  30

Ile Pro Gly Asp Phe Val Leu Ser Val Ser Glu Ser Ser Arg Val
                 35                   40                  45

Ser His Tyr Ile Val Asn Ser Leu Gly Pro Ala Gly Gly Arg Arg
                 50                   55                  60

Ala Gly Gly Glu Phe Asp Ser Leu Pro Ser Leu Leu Glu Phe Tyr
                 65                   70                  75

Lys Ile His Tyr Leu Asp Thr Thr Thr Leu Ile Glu Pro Val
                 80                   85
```